(12) United States Patent
Remmers et al.

(10) Patent No.: US 10,709,599 B2
(45) Date of Patent: Jul. 14, 2020

(54) SYSTEMS AND METHODS FOR PROVIDING AN AUTOMATED TITRATION FOR ORAL APPLIANCE THERAPY

(71) Applicant: ZST HOLDINGS, INC., Calgary (CA)

(72) Inventors: John Remmers, Sedona, AZ (US); Seyed Abdolali Zareian Jahromi, Calgary (CA); Joshua Grosse, Calgary (CA); Zbigniew Ludwik Topor, Calgary (CA); Paul Cataford, Calgary (CA)

(73) Assignee: ZST Holdings, Inc., Calgary, AB (CA)

( * ) Notice: Subject to any disclaimer, the term of this patent is extended or adjusted under 35 U.S.C. 154(b) by 104 days.

(21) Appl. No.: 15/560,786

(22) PCT Filed: Mar. 31, 2016

(86) PCT No.: PCT/IB2016/051857
§ 371 (c)(1),
(2) Date: Sep. 22, 2017

(87) PCT Pub. No.: WO2016/157129
PCT Pub. Date: Oct. 6, 2016

(65) Prior Publication Data
US 2018/0078403 A1 Mar. 22, 2018

Related U.S. Application Data

(60) Provisional application No. 62/140,637, filed on Mar. 31, 2015.

(51) Int. Cl.
*A61F 5/56* (2006.01)
*A61C 19/04* (2006.01)
(Continued)

(52) U.S. Cl.
CPC .............. *A61F 5/566* (2013.01); *A61C 7/08* (2013.01); *A61C 19/04* (2013.01); *A61F 5/56* (2013.01);
(Continued)

(58) Field of Classification Search
CPC ... A61B 5/4836; A61B 5/4557; A61B 5/4818; A61B 5/4848; A61B 5/486;
(Continued)

(56) References Cited

U.S. PATENT DOCUMENTS 2,171,695 A 9/1939 Harper
4,376,628 A 3/1983 Aardse
(Continued)

FOREIGN PATENT DOCUMENTS

CN 1602970 4/2005
CN 101917924 12/2010
(Continued)

OTHER PUBLICATIONS

Almeida, F.R., et al., "Effect of a Titration Polysomnogram on Treatment Success with a Mandibular Repositioning Appliance," Journal of Clinical Sleep Medicine, vol. 5, No. 3, 2009, pp. 198-204.
(Continued)

*Primary Examiner* — Tammie K Marlen
(74) *Attorney, Agent, or Firm* — Meunier Carlin & Curfman LLC

(57) ABSTRACT

Systems and methods for setting one or more parameters for a multi-test-period titration for oral appliance therapy are described herein. A method can include performing a titration for oral appliance therapy during a first test period, identifying a variable associated with the titration performed during the first test period, and setting a parameter for a titration for oral appliance therapy to be performed during a second test period. The parameter can be dependent on the
(Continued)

variable associated with the titration performed during the first test period. The method can also include performing the titration for oral appliance therapy during the second test period, and establishing an outcome of oral appliance therapy based on the titrations performed during the first and second test periods.

26 Claims, 32 Drawing Sheets

(51) Int. Cl.
*G01N 33/48* (2006.01)
*A61C 7/08* (2006.01)
*A61B 5/08* (2006.01)
*A61B 5/11* (2006.01)
*A61B 5/00* (2006.01)

(52) U.S. Cl.
CPC ............ *G01N 33/48* (2013.01); *A61B 5/0816* (2013.01); *A61B 5/1116* (2013.01); *A61B 5/4542* (2013.01); *A61B 5/4812* (2013.01); *A61B 5/4818* (2013.01); *A61B 5/7264* (2013.01); *A61B 5/746* (2013.01); *G01N 2800/52* (2013.01)

(58) Field of Classification Search
CPC ... A61B 5/7246; A61B 5/7275; A61B 5/7282; A61B 5/7264; A61B 5/4542; A61B 5/682; A61F 5/56; A61F 5/566
See application file for complete search history.

(56) References Cited

U.S. PATENT DOCUMENTS

| | | |
|---|---|---|
| 4,602,905 A | 7/1986 | O'Keefe |
| 4,901,737 A | 2/1990 | Toone |
| 5,030,098 A | 7/1991 | Branford |
| 5,154,609 A | 10/1992 | George |
| 5,313,960 A | 5/1994 | Tomasi |
| 5,365,945 A | 11/1994 | Halstrom |
| 5,409,017 A | 4/1995 | Lowe |
| 5,427,117 A | 6/1995 | Thornton |
| 5,513,986 A | 5/1996 | Feltham et al. |
| 5,537,994 A | 7/1996 | Thornton |
| 5,566,683 A | 10/1996 | Thornton |
| 5,570,704 A | 11/1996 | Buzzard et al. |
| 5,611,355 A | 3/1997 | Nilsen |
| 5,642,737 A | 7/1997 | Parks |
| 5,666,960 A | 9/1997 | Fredberg et al. |
| 5,671,733 A | 9/1997 | Raviv et al. |
| 5,678,567 A | 10/1997 | Thornton et al. |
| 5,755,219 A | 5/1998 | Thornton |
| 5,782,240 A | 7/1998 | Raviv et al. |
| 5,794,627 A | 8/1998 | Frantz et al. |
| 5,816,799 A | 10/1998 | Parker |
| 5,823,193 A | 10/1998 | Singer et al. |
| 5,826,579 A | 10/1998 | Remmers et al. |
| 5,829,441 A | 11/1998 | Kidd |
| 5,846,212 A | 12/1998 | Beeuwkes et al. |
| 5,868,138 A | 2/1999 | Halstrom |
| 5,884,628 A | 3/1999 | Nilsen |
| 5,921,942 A | 7/1999 | Remmers et al. |
| 5,941,247 A | 8/1999 | Keane |
| 5,953,713 A | 9/1999 | Behbehani |
| 5,954,048 A | 9/1999 | Thornton |
| 5,961,447 A | 10/1999 | Raviv et al. |
| 5,983,892 A | 11/1999 | Thornton |
| 6,012,920 A | 1/2000 | Woo |
| 6,041,784 A | 3/2000 | Halstrom |
| 6,055,986 A | 5/2000 | Meade |
| 6,109,265 A | 8/2000 | Frantz et al. |
| 6,155,262 A | 12/2000 | Thornton et al. |
| 6,161,542 A | 12/2000 | Halstrom |
| 6,273,859 B1 | 8/2001 | Remmers et al. |
| 6,290,654 B1 | 9/2001 | Karakasoglu |
| 6,305,376 B1 | 10/2001 | Thornton |
| 6,325,064 B1 | 12/2001 | Thornton |
| 6,374,824 B1 | 4/2002 | Thornton |
| 6,450,167 B1 | 9/2002 | David et al. |
| 6,516,805 B1 | 2/2003 | Thornton |
| 6,634,353 B1 | 10/2003 | Knebelman et al. |
| 6,729,335 B1 | 5/2004 | Halstrom |
| 6,769,910 B1 | 8/2004 | Pantino |
| 6,877,513 B2 | 4/2005 | Scarberry et al. |
| 7,146,982 B2 | 12/2006 | Mousselon et al. |
| 7,174,895 B2 | 2/2007 | Thornton et al. |
| 7,282,027 B2 | 10/2007 | Sotos et al. |
| 7,328,698 B2 | 2/2008 | Scarberry et al. |
| 7,331,349 B2 | 2/2008 | Brady et al. |
| 7,357,635 B2 | 4/2008 | Belfor et al. |
| 7,396,333 B2 | 7/2008 | Stahmann et al. |
| 7,328,705 B2 | 12/2008 | Abramson |
| 7,637,262 B2 | 12/2009 | Bailey |
| 7,712,468 B2 | 5/2010 | Hargadon |
| 7,832,403 B2 | 11/2010 | Halstrom et al. |
| 7,841,987 B2 | 11/2010 | Sotos et al. |
| 8,001,973 B2 | 8/2011 | Sotos et al. |
| 8,025,063 B2 | 9/2011 | Sotos et al. |
| 8,037,886 B2 | 10/2011 | Sotos et al. |
| 8,226,407 B2 | 7/2012 | Hanewinkel et al. |
| 8,550,816 B2 | 10/2013 | Hanewinkel et al. |
| 8,646,447 B2 | 2/2014 | Martin et al. |
| 2002/0165462 A1 | 11/2002 | Westbrook et al. |
| 2003/0224313 A1 | 12/2003 | Bergersen |
| 2004/0030224 A1 | 2/2004 | Sotos et al. |
| 2005/0028827 A1 | 2/2005 | Halstrom |
| 2005/0081859 A1 | 4/2005 | Scarberry et al. |
| 2005/0175709 A1 | 8/2005 | Baty et al. |
| 2005/0175954 A1 | 8/2005 | Zacher |
| 2005/0241646 A1 | 11/2005 | Sotos et al. |
| 2006/0003292 A1 | 1/2006 | Lauren et al. |
| 2006/0020178 A1 | 1/2006 | Sotos et al. |
| 2006/0063981 A1 | 3/2006 | Sotos et al. |
| 2006/0155205 A1 | 7/2006 | Sotos et al. |
| 2006/0266356 A1 | 11/2006 | Sotos et al. |
| 2007/0068534 A1 | 3/2007 | Bailey et al. |
| 2007/0183572 A1 | 8/2007 | Drummond et al. |
| 2007/0239056 A1 | 10/2007 | Moore |
| 2007/0283967 A1 | 12/2007 | Bailey |
| 2007/0283973 A1 | 12/2007 | Longley |
| 2008/0053461 A1 | 3/2008 | Hirotsuka et al. |
| 2008/0064008 A1 | 3/2008 | Schmitt |
| 2008/0076094 A1 | 3/2008 | Hindin |
| 2008/0236597 A1 | 10/2008 | Bergersen |
| 2009/0078257 A1 | 3/2009 | Bhat et al. |
| 2009/0078274 A1 | 3/2009 | Bhat et al. |
| 2009/0241969 A1 | 10/2009 | Walker |
| 2010/0018538 A1 | 1/2010 | Sotos et al. |
| 2010/0101583 A1 | 4/2010 | Chen et al. |
| 2010/0154802 A1 | 6/2010 | Fuselier |
| 2010/0163043 A1 | 7/2010 | Hart et al. |
| 2010/0204614 A1 | 8/2010 | Lindquist et al. |
| 2010/0217426 A1 | 8/2010 | Sotos et al. |
| 2010/0240982 A1 | 9/2010 | Westbrook et al. |
| 2010/0300457 A1 | 12/2010 | Horchover |
| 2010/0316973 A1 | 12/2010 | Remmers et al. |
| 2011/0005299 A1 | 1/2011 | Rouse |
| 2011/0005526 A1 | 1/2011 | Garabadian et al. |
| 2011/0168186 A1 | 7/2011 | Halstrom |
| 2011/0217674 A1 | 9/2011 | Hanewinkel et al. |
| 2011/0232652 A1 | 9/2011 | Levendowski et al. |
| 2011/0295083 A1 | 12/2011 | Doelling et al. |
| 2013/0023797 A1 | 1/2013 | Hanewinkel et al. |
| 2014/0114146 A1 | 4/2014 | Hanewinkel et al. |
| 2014/0180036 A1 | 6/2014 | Bukkapatnam et al. |
| 2015/0007830 A1 | 1/2015 | Remmers et al. |
| 2015/0039045 A1 | 2/2015 | Ni et al. |

(56) References Cited

U.S. PATENT DOCUMENTS

| | | |
|---|---|---|
| 2015/0164682 A1 | 6/2015 | Remmers et al. |
| 2016/0022205 A1 | 1/2016 | Remmers et al. |

FOREIGN PATENT DOCUMENTS

| | | |
|---|---|---|
| CN | 102481181 | 5/2012 |
| CN | 103841888 A | 6/2014 |
| CN | 104066400 A | 9/2014 |
| EP | 1832306 | 9/2007 |
| JP | 2001-524852 | 12/2001 |
| WO | 1998/046177 | 10/1998 |
| WO | 2005025417 A1 | 3/2005 |
| WO | 2005/107590 | 11/2005 |
| WO | 2005/115266 | 12/2005 |
| WO | 2008/151374 | 12/2008 |
| WO | 2010/072387 | 7/2010 |
| WO | 2010/087824 | 8/2010 |
| WO | 2010/141868 | 12/2010 |
| WO | 2010/141957 | 12/2010 |
| WO | 2011/005299 | 1/2011 |
| WO | 2011/082346 | 7/2011 |
| WO | 2011/147985 | 12/2011 |
| WO | 2013/102095 | 7/2013 |
| WO | 2013/188660 | 12/2013 |
| WO | 2014/159236 | 10/2014 |
| WO | 2014/170855 | 10/2014 |

OTHER PUBLICATIONS

Cartwright, R.D., "Predicting Response to the Tongue Retaining Device for Sleep Apnea Syndrome," Arch. Otolaryngol., vol. 111, 1985, pp. 385-388.

Chan, A.S.L., et al., "Nasopharyngoscopic evaluation of oral appliance therapy for obstructive sleep apnoea," European Respiratory Journal, vol. 35, No. 4, 2010, pp. 836-842.

Clark, S.A., et al., "Assessment of Inspiratory Flow Limitation Invasively and Noninvasively during Sleep," American Journal of Respiratory and Critical Care Medicine, vol. 158, 1998, pp. 713-722.

Dort, L.C., et al., "Mandibular advancement and obstructive sleep apnoea: a method for determining effective mandibular protrusion," European Respiratory Journal, vol. 27, No. 5, 2006, pp. 1003-1009.

Friedman, M., et al., "Compliance and Efficacy of Titratable Thermoplastic versus Custom Mandibular Advancement Devices," Otolaryngology-Head and Neck Surgery, vol. 147, No. 2, 2012, pp. 379-386.

Kim, Y.-K., et al., "The influence of the amount of mandibular advancement in the application of mandibular advancement device for obstructive sleep apnea patients," Sleep Medicine and Psychophysiology, vol. 18, No. 6, 2011, pp. 29-34. (English Abstract).

Levendowski, D.J., et al., "Initial Evaluation of a Titration Appliance for Temporary Treatment of Obstructive Sleep Apnea," J. Sleep Disord. Ther., vol. 1, Issue 1, 2011, 8 pages.

Liu, Y., et al., "Cephalometric and physiologic predictors of the efficacy of an adjustable oral appliance for treating obstructive sleep apnea," American Journal of Orthodontics and Dentofacial Orthopedics, vol. 120, No. 6, 2001, pp. 639-647.

Marklund, M., et al., "Treatment Success with a Mandibular Advancement Device is Related to Supine-Dependent Sleep Apnea," Chest, vol. 114, No. 6, 1998, pp. 1630-1635.

Morgenstern, C., et al., "Assessment of Changes in Upper Airway Obstruction by Automatic Identification of Inspiratory Flow Limitation During Sleep," IEEE Transactions on Biomedical Engineering, vol. 56, No. 8, 2009, pp. 2006-2015.

Otsuka, R., et al., "A comparison of responders and nonresponders to oral appliance therapy for the treatment of obstructive sleep apnea," American Journal of Orthodontics and Dentofacial Orthopedics, vol. 129, No. 2, 2006, pp. 222-229.

Pételle, B., et al., "One-Night Mandibular Advancement Titration for Obstructive Sleep Apnea Syndrome," American Journal of Respiratory and Critical Care Medicine, vol. 165, 2002, pp. 1150-1153.

Remmers, J., et al., "Remotely Controlled Mandibular Protrusion during Sleep Predicts Therapeutic Success with Oral Appliances in Patients with Obstructive Sleep Apnea," Sleep, vol. 36, No. 10, 2013, pp. 1517-1525A.

Tsai, W.H., et al., "Remotely Controlled Mandibular Positioner Predicts Efficacy of Oral Appliances in Sleep Apnea," American Journal of Respiratory and Critical Care Medicine, vol. 170, No. 4, 2004, pp. 366-370.

Tsuiki, S., et al., "Optimal positive airway pressure predicts oral appliance response to sleep apnoea," European Respiratory Journal, vol. 35, No. 5, 2010, pp. 1098-1105.

Vázquez, J.-C., et al., "Automated analysis of digital oximetry in the diagnosis of obstructive sleep apnoea," Thorax., vol. 55, 2000, pp. 302-307.

De Backer, et al., "Functional imaging using computational fluid dynamics to predict treatment success of mandibular advancement devices in sleep-disordered breathing", Journal of Biomechanics, 2007, vol. 40, pp. 3708-3714.

Kuna et al., "Evaluation of an oral mandibular advancement titration appliance," Oral Surg Oral Med Oral Pathol Oral Radiol Endod, 2006, vol. 101, No. 5, pp. 593-603.

Extended European Search Report issued for European Application No. 16771509.3, dated Oct. 8, 2018, 5 pages.

International Search Report and Written Opinion issued for Application No. PCT/IB2016/051857, dated Jul. 11, 2016, 11 pages.

International Preliminary Report on Patentability Opinion issued for Application No. PCT/IB2016/051857, dated Oct. 12, 2017, 8 pages.

International Search Report and Written Opinion of the International Searching Authority from the International Application No. PCT/US2014/022638 dated Feb. 6, 2015.

Supplementatry Search Report issued in European Application No. 14776224.7, dated Oct. 7, 2016.

Communication Pursuant to Article 94(3) EPC, issued in European Application No. 14776224.7, dated Oct. 26, 2016.

Communication Pursuant to Article 94(3) EPC, issued in European Application No. 14776224.7, dated Aug. 29, 2017.

Summons to Attend Oral Proceedings Pursuant to Rule 115(1) EPC, issued in European Application No. 14776224.7, dated Oct. 12, 2018.

Office Action issued in Chinese Application No. 201480013459.3, dated Jun. 14, 2018 (with English-language translation).

Office Action issued in Chinese Application No. 201480013459.3, dated Nov. 3, 2017(with English-language translation).

Office Action issued in Chinese Application No. 201480013459.3, dated Dec. 30, 2016(with English-language translation).

Office Action issued in Japanese Application No. 2016-501023, dated Apr. 2, 2018 (with English-language translation).

Office Action issued in Japanese Application No. 2016-501023, dated Mar. 4, 2019 (with English-language translation).

Examination report issued in Australian Application No. 2014241067, dated Apr. 9, 2018.

Examination report No. 1 issued for Australian Application No. 2016241595, dated Aug. 20, 2019.

Office Action issued for Chinese Application No. 201680026859.7, dated Jan. 21, 2020.

Office Action issued for Japanese Application No. 2017-551260, dated Feb. 17, 2020.

Measure of Respiratory Events (e.g., apneas, hypopneas, or any other respiratory event)
A frequency of respiratory events during a given period of time
A count of respiratory events during a given period of time
Residual RDI, AHI, Residual AHI, etc. over "X" period of time
Residual RDI, AHI, Residual AHI, etc. at a given protrusion level or range of protrusion levels
High, low, average, etc. of Residual RDI, AHI, Residual AHI
Analysis of a plot of the measure of respiratory events (e.g., AHI), e.g., a slope of the AHI plot over a given period of time

Measure of Protrusion Level
Percentage of test period spent above or below "X" protrusion level
Percentage of test period spent above or below "X" protrusion level for "Y" amount of time
Protrusion level where "X" percentage of time was spent above or below
Protrusion level associated with "X" measure of respiratory events (e.g., AHI)

Attractor Behavior
Count of attractors in a given period of time
Frequency of attractors in a given period of time
High, low, average, etc. of attractors in a given time period

*FIG. 12* ary identify candidates suitable for oral appliance therapy, as well as identify target effective protrusion levels.

According to some conventional OA therapy techniques, a patient's mandible is incrementally displaced in response to evidence of obstruction. For example, U.S. Pat. No. 6,273,859 describes a process of monitoring for evidence of obstruction (i.e., as opposed to respiratory events as described herein) and incrementally displacing the patient's mandible until in response thereto until the evidence of obstruction is reduced/eliminated. In U.S. Pat. No. 6,273,859, the position of the patient's mandible is continuously monitored and adjusted to an optimal position to reduce/eliminate evidence of obstruction. In other words, when providing OA therapy, the level of protrusion can be held at the level of protrusion that reduces/eliminates evidence of obstruction (i.e., an optimal level of protrusion), or it can be automatically adjusted in response to evidence of obstruction (i.e., to another optimal level of protrusion). Thus, the current position is considered the optimal position or the treatment position since it reduces/eliminates evidence of obstruction. U.S. Patent Application Publication No. 2014/0114146, filed Oct. 22, 2013 and entitled "Diagnostic devices, mandibular manipulators with tongue and nasal sensors, automated mandibular manipulators and related methods," describes another automatically-controlled mandibular positioner adapted to incrementally adjust the patient's mandible to an optimal position to reduce/eliminate evidence of obstruction.

SYSTEMS AND METHODS FOR PROVIDING AN AUTOMATED TITRATION FOR ORAL APPLIANCE THERAPY

CROSS-REFERENCE TO RELATED APPLICATIONS

This application is a national stage application filed under 35 U.S.C. § 371 of PCT/IB2016/051857 filed Mar. 31, 2016, which claims the benefit of U.S. Provisional Patent Application No. 62/140,637, filed on Mar. 31, 2015, entitled "SYSTEMS AND METHODS FOR PROVIDING AN AUTOMATED TITRATION FOR ORAL APPLIANCE THERAPY," the disclosures of which are expressly incorporated herein by reference in their entireties.

BACKGROUND

Obstructive sleep apnea (OSA) is a common disease that is largely under-diagnosed and untreated. Nasal continuous positive airway pressure (CPAP) is the standard treatment for OSA. CPAP entails use of a nose mask to deliver positive pressure, which dilates a subject's pharynx and eliminates obstruction. This therapy is highly efficacious and benign but is associated with low adherence in many subjects, particularly those with disease of mild and moderate severity. The principal alternative to CPAP therapy is oral appliance (OA) therapy in which a custom made mandibular repositioner (MR) is used to protrude the subject's mandible during sleep, thereby opening the subject's pharyngeal airway. OA therapy, while preferred and well accepted by most subjects, is not uniformly effective in eliminating sleep apnea.

The effectiveness of OA therapy can be improved by screening OSA subjects and prospectively identifying those suitable for this therapy. Studies of the passive pharynx indicate that the response of the pharynx to mandibular protrusion is dose dependent. In other words, incremental mandibular protrusion produces corresponding pharyngeal enlargement. However, clinical experience shows that excessive mandibular protrusion is undesirable, producing side effects, such as, pain and tooth movement that lead to discontinuation of therapy. In some cases, over-protrusion can worsen OSA. According to current practice, a treatment provider such as a dentist progressively protrudes the subject's mandible until a symptomatic response occurs. The subject is then reassessed to determine if OSA has resolved.

Prospective identification of suitable candidates, as well as target effective protrusion levels, can greatly facilitate treatment of OSA with OA therapy. U.S. Pat. No. 5,826,579 to Remmers et al., filed Oct. 25, 1996 and entitled "Remote-Controlled Mandibular Positioning Device and Method of Using the Device," which is incorporated herein in its entirety by reference, describes a remotely-controlled mandibular positioner (RCMP). Additionally, U.S. Pat. No. 6,273,859 to Remmers et al., filed Jun. 8, 1999 and entitled "Adaptively Controlled Mandibular Positioning Device and Method of Using the Device," which is incorporated herein in its entirety by reference, describes an OA therapy which is an automatically-controlled mandibular positioner (ACMP). Additionally, U.S. 2016/0022205, filed Mar. 10, 2014 and entitled "SYSTEMS AND METHODS FOR PROVIDING AN AUTOMATED TITRATION FOR ORAL APPLIANCE THERAPY," which is incorporated herein in its entirety by reference, describes methods by which an automatically-controlled mandibular positioner can pro- Additionally, the conventional approach to the titration for OA therapy is to evaluate the physiological response (e.g., classic respiratory events such as apneas, hypopneas, snoring, etc. and/or evidence of obstructions) at discrete levels mandibular protrusion. This is as opposed to the adaptive OA therapy described in U.S. Pat. No. 6,273,859 as described above. For example, U.S. Pat. No. 8,001,973 to Sotos et al., filed Jul. 20, 2009 and entitled "SYSTEM AND METHOD FOR TREATMENT OF UPPER AIRWAY DISORDERS," describes a conventional process of providing the patient with a plurality of sets of appliances, where each set of appliances is adapted to displace the patient's mandible with a fixed level of protrusion. A first fixed level of protrusion is maintained constant all night using a first set of appliances and therapeutic effectiveness is assessed offline at the end of the night (e.g., using conventional home monitors). The outcome from the analysis during the night at the first fixed level of protrusion is used to decide whether to proceed with a next night at a different fixed level of protrusion using a second set of appliances, for example, in order to achieve therapeutic success. Alternatively, therapeutic effectiveness is assessed offline by evaluating the physiologic response at various levels of protrusion that are collected during a polysomnographic study during which a technician either manually (e.g., at the MR) or remotely (e.g., using the RCMP) adjusts an MR.

SUMMARY

An example method for setting one or more parameters for a multi-test-period titration for oral appliance therapy is described herein. The method can include performing a titration for oral appliance therapy during a first test period, identifying a variable associated with the titration performed during the first test period, and setting a parameter for a titration for oral appliance therapy to be performed during a second test period. The parameter can be dependent on the variable associated with the titration performed during the first test period. The method can also include performing the titration for oral appliance therapy during the second test period, and establishing an outcome of oral appliance therapy based on the titrations performed during the first and second test periods.

Optionally, the variable can be a predicted outcome of oral appliance therapy, a predicted effective protrusion level for oral appliance therapy, a predicted optimal protrusion level for oral appliance therapy, a measure of respiratory events, a measure of respiratory events at or above a specific protrusion level, a percentage of time spent at or above a specific protrusion level, a sleep stage, an occurrence of arousal and/or other variables measured from the data set (such as the example variables illustrated in FIG. 12). For example, in one implementation described below, the variable is the predicted outcome of oral appliance therapy.

Alternatively or additionally, the parameter can optionally be a beginning protrusion level, a protrusion level adjustment rate, a protrusion level range, a criterion for adjusting the protrusion level, a width and position of a correlation window, a type of protocol, criteria defining a respiratory event, a sleep study qualifying condition, or a length of time before adjusting/re-adjusting protrusion level. For example, in one implementation described below, the parameter is the beginning protrusion level. Optionally, the beginning protrusion level can be a predicted effective protrusion level for oral appliance therapy or a percentage of a maximum protrusion level tolerated by the subject.

Alternatively or additionally, the outcome of oral appliance therapy can optionally be a prediction of success or failure of oral appliance therapy, a predicted effective protrusion level for oral appliance therapy, or a predicted optimal protrusion level for oral appliance therapy. For example, the outcome of oral appliance therapy can be the predicted effective protrusion level for oral appliance therapy determined during at least one of the test periods (e.g., the first test period, the second test period, etc.) and can also be dependent on the variable associated with the titration performed during the at least one of the test periods.

Alternatively or additionally, the method can optionally include receiving diagnostic information concerning the subject. The diagnostic information can be used to establish the outcome of oral appliance therapy or to set the parameter for a titration. The diagnostic information can optionally also be used to set a test plan. Optionally, the diagnostic information can be any information about the subject, including but not limited to a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms. For example, the diagnostic information can be obtained before (e.g., as a result of a diagnostic study) or during a titration performed during one or more of the test periods. For example, in one implementation described below, the diagnostic information is a frequency of respiratory events (e.g., a baseline measure of respiratory events such as an apnea-hypopnea index (AHI), an oxygen desaturation index (ODI) or a respiratory disturbance index (RDI)). Additionally, the baseline measure can optionally be a measure of respiratory events experienced by the subject in the absence of oral appliance therapy.

Alternatively or additionally, the method can optionally include identifying a variable associated with the titration performed during the second test period, and determining whether to perform a titration for oral appliance therapy during a third test period based on the variable associated with the titration performed during the first and/or second test period. When the titration for oral appliance therapy is performed during the third test period, the method can optionally include setting a parameter for the titration for oral appliance therapy to be performed during the third test period, and performing the titration for oral appliance therapy during the third test period. Similar to above, the parameter can be dependent on the variable associated with the titration performed during the first and/or second test period. In addition, the outcome of oral appliance therapy can be established based on the titrations performed during at least two of the first, second, and third test periods.

Alternatively or additionally, the method can further include determining whether to perform a titration for oral appliance therapy during one or more additional test periods based on diagnostic information concerning the subject, a desired outcome of oral appliance therapy, a desired level of accuracy for the outcome of oral appliance therapy, a desired total number of test periods, a sensitivity or tolerance of the subject, or a constraint of an adjustable mandibular displacement device.

Alternatively or additionally, each respective test period can be sleep during a different sleep session. The different sleep sessions can be on the same night. Alternatively, the different sleep sessions can be on different nights.

Alternatively or additionally, a titration for oral appliance therapy can include positioning an adjustable mandibular displacement device in an oral cavity of a subject, monitoring physiological information from the subject, and adjusting a protrusion level of the adjustable mandibular displacement device.

Alternatively or additionally, the method can optionally include developing a test plan for the multi-test-period titration, and performing the titrations during the first and second test periods according to the test plan. Optionally, the test plan is developed before performing at least one of the titration during the first or second test period. Optionally, the test plan is developed before performing any of the titrations. Optionally, the test plan is developed based on at least one of a desired outcome of oral appliance therapy, a desired level of accuracy of the outcome of oral appliance therapy, diagnostic information concerning the subject, or a limitation of the subject or a mandibular displacement device.

Alternatively or additionally, in some implementations, the outcome of oral appliance therapy is established using a machine learning algorithm such as neural network, support vector machine, decision tree, random forest, etc.

An example system for setting one or more parameters for a multi-test-period titration for oral appliance therapy is also described herein. The system can include a mandibular displacement device configured to be positioned in an oral cavity of a subject, a monitoring unit configured to sense one or more physiological inputs from the subject, and a control unit. The control unit can include a processing unit and a memory operatively coupled to the processing unit. In addition, the memory can have computer-executable instructions stored thereon that, when executed by the processing unit, cause the system to perform the operations for developing a test plan for a multi-test-period titration for oral appliance therapy. This disclosure contemplates that the system can be configured to perform any of the operations described herein, including operations for developing a test plan for a multi-test-period titration for oral appliance therapy.

An example method for evaluating an outcome of oral appliance therapy in a subject using a multi-test-period titration is also described herein. The method can include receiving diagnostic information concerning the subject, performing a titration for oral appliance therapy during each of first and second test periods, respectively, analyzing at least one variable associated with the titrations performed during the first and second test periods, and establishing the outcome of oral appliance therapy based on the at least one variable. The diagnostic information can influence selection of the at least one variable.

Optionally, the diagnostic information can be any information about the subject, including but not limited to a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms. For example, the diagnostic information can be obtained before (e.g., as a result of a diagnostic study) or during a titration performed during one or more of the test periods. For example, the diagnostic information is a frequency of respiratory events such as an apnea-hypopnea index (AHI), oxygen desaturation index (ODI), or respiratory disturbance index (RDI) (e.g., a baseline measure of respiratory events). Additionally, the baseline measure can optionally be a measure of respiratory events experienced by the subject in the absence of oral appliance therapy.

For example, in one implementation described below, the diagnostic information is a baseline measure of respiratory events experienced by the subject. Additionally, the at least one variable is a first variable when the diagnostic information is greater than a threshold value, and the at least one variable is a second variable when the diagnostic information is less than a threshold value. The threshold value can optionally be between 15 and 40 respiratory events per hour. In an example implementation, the threshold value can optionally be approximately 20 respiratory events per hour, for example, approximately 16 respiratory events per hour.

Alternatively or additionally, the at least one variable can be a measure of respiratory events, for example, a frequency of respiratory events occurring during the titration performed during the first or second test period.

Alternatively or additionally, the outcome of oral appliance therapy can be established based on a value of the at least one variable. Optionally, the method can include, based on a value of the at least one variable, performing a titration for oral appliance therapy during a third test period. The outcome of oral appliance therapy can be established based on a value of a variable associated with the titration performed during the third test period.

Alternatively or additionally, the outcome of oral appliance therapy can optionally be a prediction of success or failure of oral appliance therapy, a predicted effective protrusion level for oral appliance therapy, or a predicted optimal protrusion level for oral appliance therapy.

Alternatively or additionally, each respective test period can be sleep during a different sleep session. The different sleep sessions can be on the same night. Alternatively, the different sleep sessions can be on different nights.

Alternatively or additionally, a titration for oral appliance therapy can include positioning an adjustable mandibular displacement device in an oral cavity of a subject, monitoring physiological information from the subject, and adjusting a protrusion level of the adjustable mandibular displacement device.

An example system for evaluating an outcome of oral appliance therapy in a subject using a multi-test-period titration is also described herein. The system can include a mandibular displacement device configured to be positioned in an oral cavity of a subject, a monitoring unit configured to sense one or more physiological inputs from the subject, and a control unit. The control unit can include a processing unit and a memory operatively coupled to the processing unit. In addition, the memory can have computer-executable instructions stored thereon that, when executed by the processing unit, cause the system to perform the operations for evaluating an outcome of oral appliance therapy in a subject using a multi-test-period titration. This disclosure contemplates that the system can be configured to perform any of the operations described herein, including operations for evaluating an outcome of oral appliance therapy in a subject using a multi-test-period titration.

An example method for qualifying conditions of a sleep study is also described herein. The method can include performing the sleep study on a subject, analyzing data collected during the sleep study to determine an amount of time of the sleep study meeting a predetermined condition, and determining whether the amount of time is greater than or equal to a predetermined threshold.

Optionally, if the amount of time is greater than or equal to the predetermined threshold, the method can include concluding the sleep study, or continuing with a next sleep session. Alternatively, if the amount of time is less than the predetermined threshold, the method can include continuing the sleep study. For example, continuing the sleep study can include performing another test period of the sleep study. Optionally, the another test period of the sleep study can be a repeat of a previous test period or a test period under conditions tailored to meeting the predetermined condition.

Alternatively or additionally, the amount of time can occur during a continuous period of sleep. Alternatively, the amount of time occurs during a plurality of non-continuous periods of sleep. Optionally, the non-continuous periods of sleep can be sleep during a plurality of test periods of the sleep study.

Alternatively or additionally, the predetermined condition can be sleep in a particular position, for example, sleep in a supine position or a lateral position. Optionally, the predetermined condition can be REM or non-REM sleep in the particular position.

Alternatively or additionally, the predetermined condition can be sleep with a mandibular displacement device fixed to the subject's teeth. Optionally, the method can include sensing when the mandibular displacement device is fixed to the subject's teeth. For example, the sensing can be performed with a force sensor for detecting force applied to the subject's teeth or by measuring energy supplied to the mandibular displacement device.

Alternatively or additionally, the method can include providing an alarm to the subject, when the subject is not sleeping in the particular position or with the mandibular displacement device fixed to the subject's teeth. Alternatively or additionally, the method can include providing a notation in a data file associated with the subject.

Alternatively or additionally, the predetermined threshold can be approximately 4 hours.

Alternatively or additionally, the sleep study can be a diagnostic sleep test that includes monitoring physiological information from the subject, and analyzing the physiological information to diagnose the subject with a sleep disordered breathing condition. The sleep disordered breathing condition can be obstructive sleep apnea (OSA), central sleep apnea (CSA), inspiratory flow limitation (IFL), high upper airway resistance (HUAR), upper airway resistance syndrome (UARS), or snoring.

Alternatively or additionally, the sleep study can be a titration for oral appliance therapy that includes positioning an adjustable mandibular displacement device in an oral cavity of the subject, monitoring physiological information from the subject, adjusting a protrusion level of the adjustable mandibular displacement device, and analyzing the physiological information to evaluate an outcome of oral appliance therapy. The outcome of oral appliance therapy can be a prediction of success or failure of oral appliance therapy, a predicted effective protrusion level for oral appliance therapy, or a predicted optimal protrusion level for oral appliance therapy.

An example system for qualifying conditions of a sleep study is also described herein. The system can include a monitoring unit configured to sense one or more physiological inputs from a subject, and a control unit. The control unit can include a processing unit and a memory operatively coupled to the processing unit. In addition, the memory can have computer-executable instructions stored thereon that, when executed by the processing unit, cause the system to perform the operations for qualifying conditions of a sleep study. This disclosure contemplates that the system can be configured to perform any of the operations described herein, including operations for qualifying conditions of a sleep study.

Optionally, the sleep study can be a diagnostic sleep test, and the system can be configured to analyze the physiological inputs to diagnose the subject with a sleep disordered breathing condition. The sleep disordered breathing condition can be obstructive sleep apnea (OSA), central sleep apnea (CSA), inspiratory flow limitation (IFL), high upper airway resistance (HUAR), upper airway resistance syndrome (UARS), or snoring.

Optionally, the sleep study can be a titration for oral appliance therapy, and the system can include a mandibular displacement device configured to be positioned in an oral cavity of a subject. The system can also be configured to perform the titration for oral appliance therapy. An outcome of oral appliance therapy can be a prediction of success or failure of oral appliance therapy, a predicted effective protrusion level for oral appliance therapy, or a predicted optimal protrusion level for oral appliance therapy.

An example method for performing a multi-purpose sleep test protocol is also described herein. The method can include providing a sleep test kit including a mandibular displacement device and one or more sensors for measuring physiological information from a subject. The sleep test kit can be configured to perform a diagnostic sleep test protocol and a titration for oral appliance therapy protocol. The method can also include providing instructions to the subject for configuring the sleep test kit during the diagnostic sleep test protocol, performing the diagnostic sleep test protocol, providing instructions to the subject for configuring the sleep test kit during the titration for oral appliance therapy protocol, and performing the titration for oral appliance therapy protocol. Additionally, the titration for oral appliance therapy protocol can be performed in dependence on an outcome of the diagnostic sleep test protocol.

Optionally, the diagnostic sleep test protocol and the titration for oral appliance therapy protocol can be performed automatically in succession. Alternatively or additionally, the diagnostic sleep test protocol and the titration for oral appliance therapy protocol can optionally be performed in a non-clinical setting such as in the subject's home.

Alternatively or additionally, the outcome of the diagnostic sleep test protocol can optionally be a measure of respiratory events. For example, the measure of respiratory events can be a number, duration, frequency, severity, or ratio of apneas or hypopneas.

Alternatively or additionally, the diagnostic sleep test protocol and the titration for oral appliance therapy protocol can be performed during a single sleep session. Alternatively, the diagnostic sleep test protocol and the titration for oral appliance therapy protocol can be performed during different sleep sessions. The different sleep sessions can be on the same night. The different sleep sessions can be on different nights.

Alternatively or additionally, the diagnostic sleep test protocol can include monitoring physiological information from the subject, and analyzing the physiological information to diagnose the subject with a sleep disordered breathing condition. The sleep disordered breathing condition can be obstructive sleep apnea (OSA), central sleep apnea (CSA), inspiratory flow limitation (IFL), high upper airway resistance (HUAR), upper airway resistance syndrome (UARS), or snoring.

Alternatively or additionally, the titration for oral appliance therapy protocol can include positioning an adjustable mandibular displacement device in an oral cavity of the subject, monitoring physiological information from the subject, adjusting a protrusion level of the adjustable mandibular displacement device, and analyzing the physiological information to evaluate an outcome of oral appliance therapy. The outcome of oral appliance therapy can be a prediction of success or failure of oral appliance therapy, a predicted effective protrusion level for oral appliance therapy, or a predicted optimal protrusion level for oral appliance therapy.

Alternatively or additionally, the method can include receiving diagnostic information concerning the subject. The diagnostic information can be used to establish an outcome of oral appliance therapy or to set a parameter for the titration for oral appliance therapy protocol. Optionally, the diagnostic information can be any information about the subject, including but not limited to a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms.

An example system for performing a multi-purpose sleep test protocol is also described herein. The system can include a mandibular displacement device configured to be positioned in an oral cavity of a subject, a monitoring unit configured to sense one or more physiological inputs from the subject, and a control unit. The control unit can include a processing unit and a memory operatively coupled to the processing unit. In addition, the memory can have computer-executable instructions stored thereon that, when executed by the processing unit, cause the system to perform the operations for performing a multi-purpose sleep test protocol. This disclosure contemplates that the system can be configured to perform any of the operations described herein, including operations for performing a multi-purpose sleep test protocol.

Another example method for evaluating an outcome of oral appliance therapy is described herein. The method can include receiving a desired outcome criteria of oral appliance therapy; performing a titration for oral appliance therapy; selecting a prediction protocol for establishing an outcome of oral appliance therapy based on the desired outcome criteria; and establishing the outcome of oral appliance therapy in accordance with the selected prediction protocol. Optionally, the method can include selecting a test protocol based on the desired outcome criteria, and the titration for oral appliance therapy can be performed according to the selected test protocol.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 12 is a table illustrating example variables associated with a test period;

DETAILED DESCRIPTION

Figure 1A:
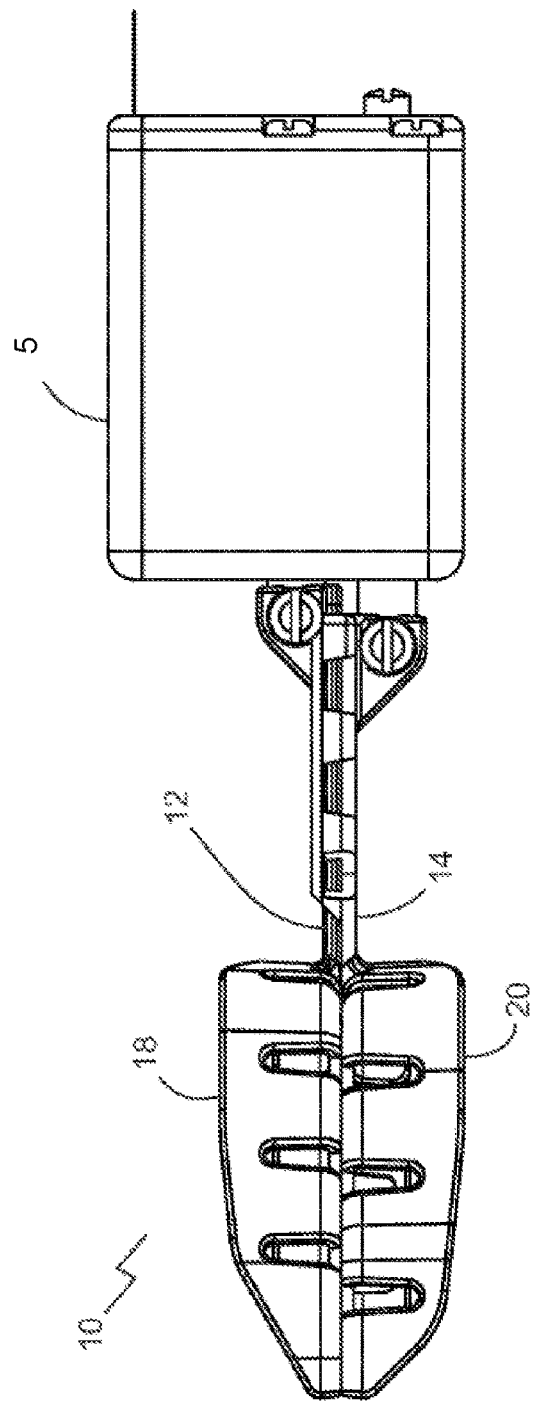
FIG. 1A illustrates an adjustable mandibular displacement device according to implementations discussed herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms. While implementations will be described for performing titrations for oral appliance therapy, it will become evident to those skilled in the art that the implementations are not limited thereto.

Provided herein are methods, systems and devices for titrating or for performing one or more titrations for oral appliance therapy. A titration can be used for evaluating the effect of repositioning the subject's mandible. Optionally, a titration can be used for an evaluation of outcome of oral appliance therapy. Optionally, a titration can provide a prediction of therapeutic outcome with oral appliance therapy. A titration can be an analysis performed prior to prescribing or providing oral appliance therapy. Alternatively or additionally, a titration can be performed periodically to assess, reassess or optimize the therapeutic effectiveness of oral appliance therapy. A titration can optionally be used to identify candidates suitable for oral appliance therapy, for instance, candidates for whom the number of respiratory disturbances is below a predetermined threshold, or for whom obstructions have been reduced or eliminated to a level deemed to provide a suitable therapeutic effect. A titration can also optionally be used to identify a clinically-beneficial orientation of the mandible or a target positioning of the mandible that is deemed to provide the suitable therapeutic effect for oral appliance therapy. For example, the target positioning of the mandible can be an effective protrusion level that reduces or eliminates respiratory disturbances and obstructions to an acceptable level. A titration can also optionally be used to identify an optimal target positioning of the mandible for oral appliance therapy. A titration optionally includes evaluating the position and/or orientation of the mandible relative to the maxilla of a subject. A titration can optionally include, or be used in conjunction with, monitoring feedback signals (e.g., respiratory airflow, oxygen saturation, sound, etc.) from the subject. A titration can optionally be performed at one or more positions and/or orientations of the mandible relative to the maxilla. Titrations can optionally be used to compare target positioning of the mandible obtained during two or more titrations performed under different conditions, such as titrations performed with the use of oral appliances having varying occlusal separations, titrations performed with the subject sleeping in varying body positions, etc.

A position and/or orientation of the subject's mandible can be adjusted during a titration (e.g., automatically during the titration) or at the start of each distinct titration or distinct test period of the same titration. A target positioning of the mandible, such as one that reduces or eliminates one or more symptoms or manifestations of a sleep disorder or condition, can be provided as a specific position (e.g., a specific protrusion level) that provides a therapeutic effect for the subject. Alternatively, the target positioning can be provided as a therapeutic zone, or range of positions, within which the subject will be provided with a therapeutic treatment. The therapeutic zone can also be provided as a map that describes the effect of position other than to the optimal reposition on the subject's airway.

The clinically-beneficial orientation or effective target positioning can optionally be predetermined in a sleep test by use of a titration system. The system is used to obtain a data set representing the clinically-beneficial orientation. For example, the system is used to obtain the data set by fitting a temporary oral appliance to the subject's teeth, incrementally and reversibly advancing the subject's mandible in the anterior-posterior direction with respect to the maxilla while the subject is sleeping and collecting physiological data. The system can include an adjustable mandibular displacement device (e.g., a titration device) such as the RCMP device discussed above. The titration device can be used to titrate the optimal position of the mandible for removal of the obstruction. The titration device can be used in the clinical setting by a technician to advance the mandible until the feedback signals (e.g., respiratory airflow, $O_2$ saturation, sound, etc.) indicate removal of the obstruction. Alternatively, the titration device can be automatically adjusted (e.g., without action by a technician) using automated algorithms to adjust the position automatically based on feedback signals. Optionally, the technician can be completely absent such as when the titration is performed in a non-clinical setting, for example, in the subject's home. Optionally, the technician can be present and optionally observing the subject during the titration while the remote-controlled mandibular displacement device is adjusted without action from the technician. Optionally, the technician can operate the titration device in a clinical setting that utilizes the automated algorithms to guide or control the titration with some level of participation or monitoring from the technician. These data can be used to establish a data set from when the mandible is in a clinically-beneficial orientation relative to the maxilla.

As discussed herein, the test period can be while the subject is sleeping. There are advantages to performing a titration for oral appliance therapy while the subject is sleeping. When the test period is while the subject is sleeping, it is possible to collect data during a plurality of conditions (e.g., sleep in lateral or supine positions, REM or non-REM sleep, periods of obstruction, etc.), which can change during the night. These conditions can include a subject's worst case of obstruction. Additionally, if the test period is while the subject is sleeping, the anatomy and function of the subject's airway during the titration is the same as the anatomy and function of the subject's airway when the oral therapy is applied. For example, during sleep the muscles are in various states of relaxation which affects the configuration and response of the subject's airway. The test period can be a single sleep session. As used herein, a sleep session can be defined by a measured duration of sleep (e.g., about 4 hours), the receipt of a sufficient amount and/or quality of data (e.g., exploration of the full range of motion of the patient's mandible), a voluntary action of the patient (e.g. the patient wakes up and concludes the study) or combinations thereof. Optionally, the test period can include multiple sleep sessions. Alternatively or additionally, the test period and/or one or more of the sleep sessions can be at least 4 hours. It should be understood that 4 hours is provided as an example and that the sleep session(s) can have a duration more or less than 4 hours. Optionally, the four hours can be either continuous (e.g., without interruption) or can be composed of several fragmented periods that together equate to a minimum of four hours. The test period can optionally have a duration less than one night or can optionally have a duration of an entire night. A titration can also optionally include multiple test periods. The type and conditions during each of the test periods can be optionally determined as a multi-test-period plan. The multi-test-period plan can be optionally determined prior to the initiation of the test, based on a desired outcome and/or patient inputs (e.g., diagnostic information concerning a subject). The multi-test-period plan, including the protocol type and conditions of the test, can optionally be determined and/or adjusted during execution of the plan by the analysis of variables during the test. The final evaluation for the titration in a multi-test-period plan can be determined by an analysis of variables from one or more of the tests during the multi-test plan, or from patient inputs (e.g., diagnostic information concerning a subject) determined outside of the test. The multi-test-period plan can also optionally be affected by a study qualification decision at the end of the test period. The titration test can optionally be associated with a different test type, using at least part of the same device. For example, the different test type can be a diagnostic test that can be used to decide if the subject should receive the oral appliance titration test. The diagnostic test can optionally be performed in the absence of oral appliance therapy (e.g., without position a mandibular displacement device in the subject's oral cavity). Alternatively or additionally, the diagnostic test can be used to measure one or more patient inputs (e.g., diagnostic information concerning a subject) for the titration test.

This disclosure contemplates that the techniques described herein can optionally employ 1) a real-time analysis for controlling the adjustable mandibular displacement device and 2) a separate analysis for predicting an outcome for oral appliance therapy. Optionally, the separate analysis can be performed offline, or at the conclusion of the sleep session or sleep study. In other words, the adjustable mandibular displacement device can be controlled in real-time in response to the data being collected (e.g., physiological responses) during a test period. Example real-time adjustable mandibular displacement device control techniques are described herein, which include but are not limited to increasing/decreasing protrusion level, optimizing respiratory airflow, the static, dynamic or refinement protocols, and/or the operations described with regard to FIG. 3 (e.g., where protrusion level is controlled in response to detected respiratory events). Optionally, adjustable mandibular displacement device control techniques can be selected to collect certain types of information. For example, the dynamic control protocol can be selected to collect data at multiple protrusion levels to identify an optimal protrusion level, while the static control protocol can be selected to confirm the predicted optimal protrusion level. Alternatively, two different control protocols can be selected to collect two different types of data sets. Optionally, the different data sets can include different types of variables. It should be understood that different adjustable mandibular displacement device control techniques can be used during different test periods.

Additionally, the outcome of oral appliance therapy (e.g., the final analysis or final evaluation) can be predicted based on the data collected during one or more test periods. The collected data can include but is not limited to one or more of the variables associated with one or more test periods (e.g., as illustrated by FIG. 12). In other words, the collected data can include data collected during a plurality of different test periods, each of which optionally employs a different adjustable mandibular displacement device control technique, and the final analysis can be predicted based on the entire set of collected data. Optionally, this analysis can be performed offline after the conclusion of the one or more test periods. Additionally, as described herein, the final analysis can employ one or more techniques for predicting the outcome of oral appliance therapy. For example, the final analysis can optionally employ a machine learning technique. Examples of machine learning techniques are neural network, support vector machine, decision tree, AdaBoost, random forest, etc. A machine learning technique can be trained to predict the outcome of oral appliance therapy. This disclosure contemplates that a neural network, support vector machine, decision tree, AdaBoost, random forest, etc. can be trained using a data set to one or more particular outcomes (e.g., AHI<10, ODI<10, or ODI<10 with a 50% reduction from baseline). The trained machine learning module(s) (e.g., neural network, support vector machine, decision tree, AdaBoost, random forest) can be executed by a computing device (e.g., computing device 50 of FIG. 1B). As described herein, it is possible to select from a plurality of trained machine learning modules (e.g., prediction protocols) based on the desired outcome. Thereafter, one or more of the variables associated with one or more test periods can be input into the trained machine learning module(s), and the machine learning module(s) can output the predicted outcome of oral appliance therapy. Example decision trees and/or random forest designed to make predictions of the outcome of oral appliance therapy are described below.

Example Titration System

Referring now to FIG. 1A, an adjustable mandibular displacement device 10 (e.g., a titration device) according to implementations discussed herein is shown. Remotely controlled adjustable mandibular displacement devices are known in the art. For example, U.S. Pat. No. 5,826,579 describes a remotely-controlled mandibular repositioner that is controlled by a technician, and U.S. Pat. No. 6,273,859 describes a remotely-controlled mandibular repositioner that is adaptively controlled by a computer. In addition, WO 2014-159236 describes an automatically-controlled mandibular positioner that is capable of performing a titration for oral appliance therapy unattended, for example, in a non-clinical environment such as the subject's home, for example. Although implementations are discussed herein with regard to the adjustable mandibular displacement device 10 shown in FIG. 1A, it should be understood that other titration devices are contemplated. For example, a titration device may be any device that has capability to reposition the mandible.

As shown in FIG. 1A, the adjustable mandibular displacement device 10 includes an upper tray 18 and a lower tray 20. The upper and lower trays 18 and 20 are attachable to an upper bracket 12 and a lower bracket 14, respectively. Additionally, the adjustable mandibular displacement device 10 includes a motor and linear actuator such as a brushless DC motor and linear actuator, which are provided in a housing 5. The specifications of the motor and linear actuator can be selected to limit a maximum travel distance (e.g., to provide a maximum of 12 mm of mandibular protrusion) and/or a maximum amount of force applied to a subject's teeth (e.g., 2.5 kg), for example. The motor and linear actuator are configured to precisely adjust the relative position of the upper and lower brackets 12 and 14. In addition, the upper and lower brackets 12 and 14 can be manually mechanically adjusted to position the upper and lower trays 18 and 20 to closely approximate a fully-retruded position of a subject's mandible. The fully-retruded position can be determined by investigation during a clinical visit prior to the titration. Thus, at the beginning of the titration, the linear actuator can be set at the fully withdrawn position when the mandible is fully-retruded. By actuating the DC motor and linear actuator, it is possible to adjust the relative position of the upper and lower brackets 12 and 14, and therefore, the relative position of the upper and lower trays 18 and 20. This exerts a force on a subject's lower jaw (mandible) to either protrude or retrude it relative to the subject's upper jaw (maxilla).

The upper and lower trays 18 and 20 can be fabricated for the subject's upper and lower teeth. This allows a close fitting of the upper and lower trays 18 and 20 to the subject's teeth so that a minimum amount of material occupies the inner surface of the teeth, which minimizes encroachment on the lingual space. This facilitates obtaining a high predictive accuracy of the titration because encroachment on the lingual space modifies the tongue position so that the oral mechanics during the titration do not mimic that which occurs when the therapeutic, custom-fitted oral appliance is used.

Figure 1B:
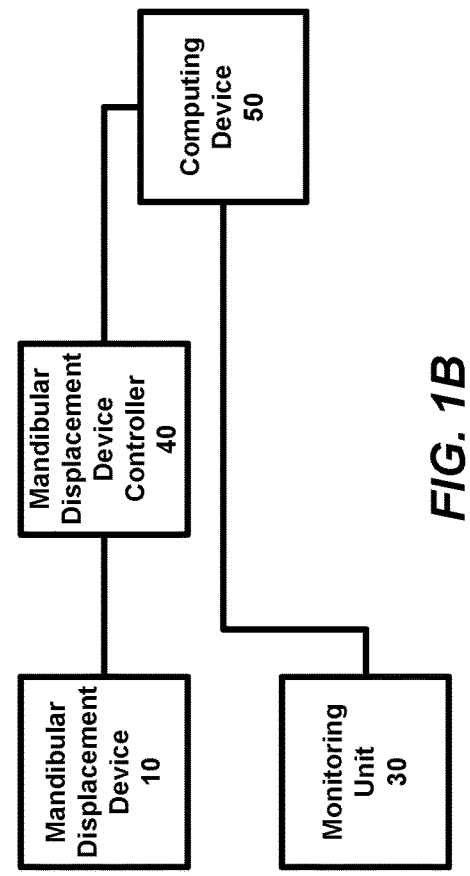
FIG. 1B is a block diagram of a titration system according to implementations discussed herein.

Referring now to FIG. 1B, a block diagram of a titration system is shown. The system can include the adjustable mandibular displacement device 10 (shown also in FIG. 1A), a monitoring unit 30, a mandibular displacement device controller 40 and a computing device 50. It should be understood that the system shown in FIG. 1B is only one example system and that a system including additional or fewer features can be provided. For example, the titration system can be implemented in a cloud computing environment to provide remote access to the components of the system. Cloud computing is a model for enabling network access to a shared pool of configurable computing resources (e.g., networks, servers, storage, applications, and services) that can be provisioned and released with minimal interaction. The cloud computing model promotes high availability, on-demand self-services, broad network access, resource pooling and rapid elasticity. It should also be understood that the communication links connecting the adjustable mandibular displacement device 10, the monitoring unit 30, the mandibular displacement device controller 40 and the computing device 50 can be any type of communication link that facilitates data communication, including, but not limited to, wired, wireless and optical communication links. For example, the adjustable mandibular displacement device 10 can be communicatively connected to the mandibular displacement device controller 40, for example, through a highly flexible, thin wire over which data including control signals are communicated between the motor and linear actuator of the adjustable mandibular displacement device 10 and the mandibular displacement device controller 40. During a titration, the mandibular displacement device controller 40 can be placed on a bedside table, for example.

In addition, the mandibular displacement device controller 40 can be communicatively connected with the computing device 50. The computing device 50 can optionally be integrated with the mandibular displacement device controller 40 as a single unit. The computing device 50 can optionally be any type of computing device such as a laptop computer, desktop computer, tablet device, or any other type of portable computing device. For example, the mandibular displacement device controller 40 can be configured to communicate data including a position of the adjustable mandibular displacement device 10 to the computing device 50. The computing device 50 can be located near the subject, as in either bedside or elsewhere within the subject's home or the treatment facility, or can be located remotely, as at the site of the manufacturer, and accessed via a network (e.g., the Internet). Optionally, aspects of the computing device 50 and/or the mandibular displacement device controller 40, such as those that control the positioning of the mandibular displacement device can be located locally, while other aspects of the computing device 50 and/or the mandibular displacement device controller 40, such as those that make decisions on which protocol to run in the next test period, can be located remotely. The computing device 50 can be configured to store and process the data as discussed in detail below. The computing device 50 can also be configured to communicate data including control signals to the mandibular displacement device controller 40.

Additionally, the monitoring unit 30 can be communicatively connected with the computing device 50. Alternatively, the monitoring unit 30 can be part of the same unit as the mandibular displacement device controller 40 and/or the computing device 50. The monitoring unit 30 can collect one or more physiological inputs, and the monitoring unit 30 can communicate the received physiological inputs to the computing device 50 for storage and/or processing. The physiological inputs can include, but are not limited to, respiratory airflow, oxygen saturation, a force on a subject's teeth, abdominal effort, brain signals, sleep stage, sleep position, acoustic energy or vibration generated by the subject, etc. These can be received directly from the subject through instrumentation such as would be applied in a standard polysomnograph recording or a portable sleep monitor. Alternatively, the physiological inputs can be received from sensors placed on a titration device (e.g., a 3D accelerometer for detecting head position, a force sensor for detecting the force applied to the teeth, accelerometers for detecting vibration of the jaw, and a microphone for detecting snoring). The computing device 50 can also be configured to communicate data including control signals to the monitoring unit 30.

Monitoring a Subject's Physiological Data

As discussed above, it is possible to monitor (or collect, measure, detect, etc.) physiological information from a subject. For example, the subject's physiological information can be monitored during a titration for oral appliance therapy. During a titration, a number of physiological inputs or data can be received from a subject. For example, as discussed above with regard to FIG. 1B, the monitoring unit 30 can collect one or more physiological inputs, and the monitoring unit 30 can communicate the received physiological inputs to the computing device 50 for storage and/or processing. The physiological inputs can include, but are not limited to, respiratory airflow, oxygen saturation, abdominal movement, brain signaling (EEG), a force on a subject's teeth, sleep stage, sleep position, acoustic energy or vibration generated by the subject, etc. These can be received directly from the subject through instrumentation such as would be applied in a standard polysomnograph recording or a portable sleep monitor. For example, the physiological inputs can include an index of respiratory airflow as recorded with nasal prongs that record pressure in the nasal airstream, electroencephalogram (EEG), electro-oculogram (EOG), submental electromyogram (EMG), electrocardiogram (ECG), arterial oxygen saturation (oxygen saturation), volume excursion of the rib cage and abdomen, snoring sound, vibrations, force measurements and body position. The physiological inputs such as airflow may be recorded with uniquely designed nasal prongs, such as those that measure the airflow separately from each nares. In addition, the physiological inputs can include supraglottic pressure through a water-filled catheter positioned in the supraglottic space. The physiological input signals can be recorded on a polygraph (and/or magnetic recording media) and displayed to a sleep technician. Alternatively or additionally, the physiological input signals can be recorded and stored directly to the titration device. Additionally, the physiological input signals can be displayed to a sleep technician and/or used by the titration system during the titration.

Detecting Respiratory Events

As discussed above, systems and devices for titrating or for performing one or more titrations for oral appliance therapy are provided. During a titration for oral appliance therapy, a subject can experience one or more respiratory events. Optionally, one or more respiratory events can be detected, for example, in real-time as opposed to in an offline quantitative analysis of historical data (e.g., data collected during a polysomnographic or home study). Optionally, one or more respiratory events can be detected automatically with or without input from a technician. Optionally, the protrusion level of the adjustable mandibular displacement device can be controlled in response to detecting a respiratory event. A respiratory event is a transient reduction or disturbance in breathing. A respiratory event is time-limited, e.g., it has a beginning and an end. During a respiratory event, the subject's physiological system is not in steady state. For example, one or more physiological inputs from the subject (e.g., respiratory airflow, oxygen saturation, etc.) change during a respiratory event. The physiological inputs can change without any intervention. The subject can experience arousal during a respiratory event, which can cause the respiratory event to end. In contrast, during steady state breathing, a normal amount of respiratory resistance can occur, which can be altered by intervention, for instance by manipulation of the mandible. A respiratory event can be defined and measured according to predetermined criteria (discussed below). Alternatively or additionally, a respiratory event can be a classical respiratory event (discussed below). For example, during a titration for oral appliance therapy, a respiratory event can be detected by comparing one or more physiological inputs from the subject against predetermined criteria. Optionally, the predetermined criteria can be the same or different than the criteria defining classical respiratory events. Optionally, the predetermined criteria used during the titration for oral appliance therapy can be the same or different than the predetermined criteria used in the evaluation of the data from the test period.

Optionally, a respiratory event can be more than mere evidence of obstruction such as changes in respiratory airflow, oxygen saturation, snoring sound, vibration, etc. A respiratory event can be defined and measured according to predetermined criteria. A respiratory event includes any disruption in breathing that is measured against predetermined criteria. Optionally, a respiratory event is detected by calculating the difference between a physiological input signal (e.g., airflow, oxygen saturation, snoring sound, vibration, etc.) and a reference value and comparing the difference to a threshold (e.g., at least one of the predetermined criteria). The physiological information discussed below can include one or more of the physiological input signals. The reference value can optionally be a calculated baseline value or a real-time value, for example. For example, a respiratory event can optionally be defined and measured according guidelines established by the American Academy of Sleep Physicians. Alternatively or additionally, the predetermined criteria can be established by clinical organizations and published as acceptable clinical standards or can be determined independently for a group of subjects or an individual subject. For example, the predetermined criteria can be established from data obtained during a previous sleep test and customized for an individual subject and/or groups of subjects. Alternatively or additionally, the predetermined criteria can be established by determined by experimental methods, for example by training a neural network using a gold standard. The sleep test can optionally be a titration test or a polysomnographic study or study with a portable sleep monitor used in the diagnosis and assessment of sleep disordered breathing. The predetermined criteria can optionally be programmed into the titration system.

Commonly known respiratory events (i.e., classical respiratory events) include apneas (e.g., obstructive apneas, central apneas, mixed apneas), hypopneas, Respiratory Effort-Related Arousals (RERA) and flow limited breathing, cheyne stokes respiration, hypoventilation, snoring, oxygen desaturation events and flow-limited breathing. The determination of respiratory events can require a change from a baseline or reference value. The baseline or reference values can be calculated in real time. The duration of a respiratory event can vary from seconds (e.g., 5-120 seconds, for example apneas or hypopneas) to minutes (e.g., 2-30 minutes or more, for example RERAs). Classical respiratory event definitions are discussed below. For example, an apnea may be defined as a reduction in respiratory airflow greater than 90% from baseline that has a duration greater than or equal to 10 seconds, with the aforementioned airflow reduction present for at least 90% of the event. A central apnea event may also have an absence of respiratory effort. A hypopnea may be a reduction in airflow greater than 30% from baseline that has a duration greater than or equal to 10 seconds, with the aforementioned airflow reduction present for at least 90% of the event in conjunction with at least a 4% reduction in blood oxygen from baseline. Alternatively, a hypopnea may be as described above with the exception of the reduction in blood oxygen being 3% from baseline.

Respiratory events as discussed herein are not limited to classical respiratory events. For example, as discussed above, oral appliance therapy can be used reduce and/or eliminate the occurrence of respiratory events, including classical respiratory events. In other words, effective oral appliance therapy reduces and/or eliminates the occurrence of classical respiratory events. During a titration for oral appliance therapy, respiratory events, including but not limited to classical respiratory events, can be detected and actions can be taken in response to detecting respiratory events. For example, respiratory events can be defined and measured according to predetermined criteria. As discussed above, the predetermined criteria can be established by clinical organization or by clinical evidence, as well as established for individual subjects and/or groups of subjects.

Figure 2A:
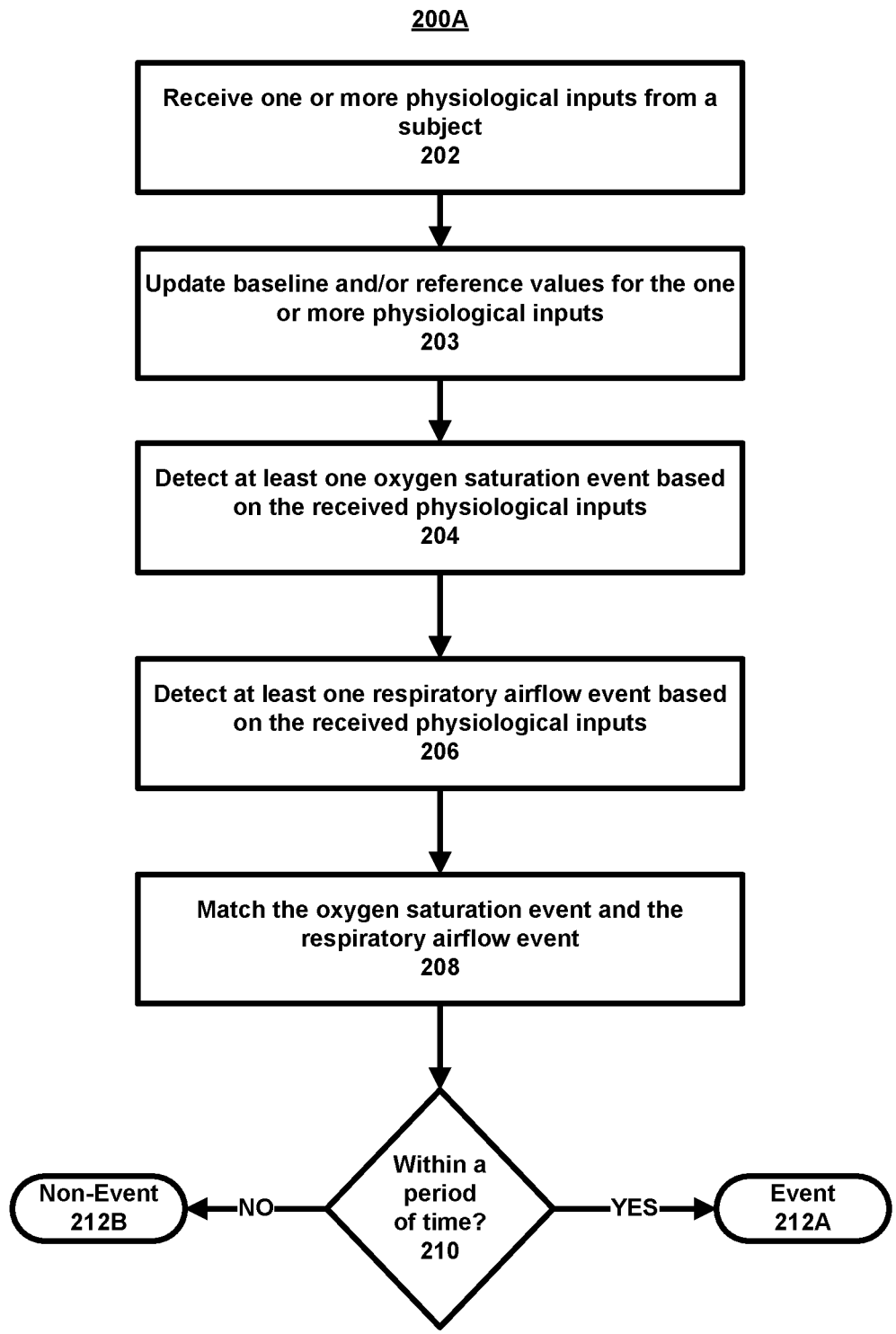
FIGS. 2A and 2B are flow diagrams illustrating example operations for detecting respiratory events.

Referring now to FIG. 2A, a flow diagram illustrating example operations 200A for detecting respiratory events is shown. Specifically, FIG. 2A illustrates example operations 200A for defining and measuring a respiratory event using predetermined criteria including a combination of oxygen saturation and respiratory airflow. Optionally, respiratory events can be defined and measured in real-time during the test period. For example, at 202, one or more physiological inputs can be received from a subject. The physiological inputs can include respiratory airflow and oxygen saturation. At 203, the reference for respiratory airflow and the baseline for oxygen saturation can optionally be updated with the inputs received at 202. Example methods for calculating baseline and reference respiratory airflow and baseline oxygen saturation are discussed below. At 204, at least one oxygen saturation event can be detected based on the received physiological inputs. For example, oxygen saturation events can be detected based on the deviation from the baseline oxygen saturation updated at 203. Additionally, at 206, at least one respiratory airflow event can be detected based on the received physiological inputs. For example, respiratory airflow events can be detected based on the deviation from the reference airflow updated at 203. Then, at 208, the oxygen saturation event and the respiratory airflow event can be matched. At 210, a determination is made as to whether the oxygen saturation event and the respiratory airflow event are detected within a period of time (e.g., the events occur within a predetermined time lag). For example, a determination can be made as to whether the oxygen saturation event is detected within a predetermined period of time after the respiratory airflow event is detected. If YES, at 212A, the matched oxygen saturation event and respiratory airflow event are classified as a respiratory event. If NO, at 212B, the matched oxygen saturation event and respiratory airflow event are not classified as a respiratory event. After matching the oxygen saturation event and respiratory airflow event, a respiratory event can be classified in terms of severity, which can also occur in real-time. In other words, the physiological inputs can be collected from the subject concurrently with the steps of detecting and matching oxygen saturation and respiratory airflow events and classifying respiratory events. According to the implementations discussed herein it is possible to continue to receive one or more physiological inputs from the subject, which is used to identify subsequent respiratory events and to update the baseline and/or reference values.

Optionally, the matched oxygen saturation event and respiratory airflow event can be classified as a respiratory event after a test period. For example, the oxygen saturation event and respiratory airflow event can be detected as a difference from a baseline or reference values calculated from the data from the whole test period.

An oxygen saturation event can be a decrease in oxygen saturation of at least a minimum amount from baseline oxygen saturation. For example, the minimum amount can be approximately 1.5%. Thus, an oxygen saturation event is detected if oxygen saturation decreases by an amount greater than 1.5% from baseline oxygen saturation. Example methods for calculating baseline oxygen saturation are provided below. This disclosure contemplates that one of ordinary skill in the art can calculate baseline oxygen saturation by another method. Optionally, baseline oxygen saturation can be calculated as a moving average. Baseline oxygen saturation can therefore optionally be calculated for an individual subject in real-time during a titration. For example, calculating the moving average can include receiving a plurality of oxygen saturation samples during a moving average time period. Oxygen saturation can optionally be sampled at 1 Hz (e.g., 1 sample per second). The moving average time period can be any time period such as 10 seconds, for example. The moving average time period can optionally be more or less than 10 seconds. Then, one or more of the plurality of oxygen saturation samples having oxygen saturation within in an Xth percentile among the plurality of oxygen saturation samples can be averaged. The Xth percentile can be the top 25th percentile (e.g., within the 75th percentile) among all of the oxygen saturation samples. It should be understood that one or more of the oxygen saturation samples can be excluded from the moving average (e.g., the oxygen saturation samples having oxygen saturation outside of the Xth percentile, for example).

Alternatively or additionally, detecting an oxygen saturation event can include detecting a decrease in the real-time value of oxygen saturation of at least a minimum amount. In other words, a decrease that is not calculated from baseline oxygen saturation can be used. For example, the minimum amount can be 1.5%. Alternatively or additionally, an oxygen saturation event can be a decrease of a threshold magnitude that is achieved by a plurality of consecutive decreases in oxygen saturation followed by an increase in oxygen saturation. As discussed above, oxygen saturation can optionally be sampled at 1 Hz (e.g., 1 sample per second). For example, the plurality of consecutive decreases in oxygen saturation can include at least 3 consecutive decreases each decrease a minimum of 0.5%. Accordingly, an oxygen saturation event can be three oxygen saturation samples with consecutively decreasing oxygen saturation followed by a sample with increasing oxygen saturation.

Respiratory airflow can be detected using nasal prongs that detect pressure in the subject's nasal airstream. The detected pressure can be an absolute pressure (e.g., pressure minus ambient pressure) in the subject's nasal airstream, for example. Optionally, the pressure in each of the subject's nares can be collected separately, and respiratory airflow can be a transformation of the pressure separately collected for each of the subject's nares. For example, the transformation can be a sum of a square root of a pressure signal (e.g., absolute pressure) separately collected for each of the subject's nares.

Baseline respiratory airflow is used to characterize the breath. For example, the baseline respiratory airflow is used to determine limits and measurements of inspiration. The baseline respiratory airflow is the average airflow calculated over a relatively long period of time such as, for example, a 20 minute period. Optionally, baseline respiratory airflow can be the average pressure detected by nasal prongs in the subject's nares as discussed below. Baseline respiratory airflow can be used to identify the "zero" point of the pressure signal from which the onset and end of each breath is identified.

Baseline respiratory airflow can be used to identify the onset and end of each breath. The onset and end of inspiration are needed to calculate breath-by-breath minute ventilation and/or peak airflow. Example methods for calculating baseline respiratory airflow are provided below. This disclosure contemplates that one of ordinary skill in the art can calculate baseline respiratory airflow by another method. For example, baseline respiratory airflow can be calculated as a moving average. The baseline respiratory airflow can therefore optionally be calculated for an individual subject in real-time during a titration. Calculating the moving average can include receiving a plurality of respiratory airflow samples during a moving average time period. Respiratory airflow can optionally be sampled at 25 Hz (e.g., 25 samples per second). The moving average time period can be any time period such as 20 minutes, for example, when calculating baseline respiratory airflow. The moving average time period can optionally be more or less than 20 minutes. Then, the moving average can be calculated as a moving mode (e.g., most-common value) based on the plurality of respiratory airflow samples. Alternatively or additionally, calculating the moving average can include receiving a plurality of respiratory airflow samples during a moving average time period, and calculating the moving average as a moving median based on the plurality of respiratory airflow samples.

Real-time calculation of the baseline respiratory airflow can then be used to detect respiratory events in real time, by providing a means of detecting the onset and the end of the inspiratory interval for each detected breath. The detection of the onset and the end of the inspiratory interval are used to measure changes in the peak airflow. The change in peak airflow can be calculated for a single breath or for a plurality of breaths. The plurality of breaths can optionally be a plurality of consecutive breaths. Alternatively, the detection of the onset and the end of the inspiratory interval by real time calculation of a baseline respiratory airflow can be used to detect a change in the breath-by-breath minute ventilation. The breath-by-breath minute ventilation may be detected as a moving average value for a time period. The respiratory airflow event can optionally be detected as monotonic decrease in calculated averaged breath-by-breath minute ventilation measured from a reference respiratory airflow followed by an increase in breath-by-breath minute ventilation. The reference respiratory airflow can be, for example, calculated as a smaller from two values with the first value being the last value of averaged breath-by-breath minute ventilation before the beginning of the monotonic decrease and the second value being the value at which the rebound is completed. Alternatively, the respiratory airflow event can optionally be detected as a change in peak to peak flow.

Optionally, reference respiratory airflow can be a moving average of respiratory airflow over a period of time such as 10 seconds, for example. Optionally, reference respiratory airflow can be an average breath-by-breath ventilation of one or more breaths. Optionally, reference respiratory airflow can be the average peak respiratory airflow of one or more breaths. For instance, respiratory airflow can be averaged during a moving time period (e.g., 10 seconds). Optionally, reference respiratory airflow can be based on the pressure detected by nasal prongs in the subject's nares. Reference respiratory airflow can be used to detect a change in respiratory airflow and/or a respiratory airflow event.

A respiratory airflow event can be a monotonic decrease followed by an increase in respiratory airflow relative to a reference respiratory airflow. For example, a respiratory airflow event can be a monotonic decrease followed by an increase in breath-by-breath minute ventilation relative to a reference breath-by-breath minute ventilation. In cases where the decrease and increase in respiratory airflow are not quite monotonic, a portion of the initial decrease can be "carried over" when calculating reference respiratory airflow.

Detection of a respiratory event by changes in minute by minute ventilation are more sensitive, as it utilizes changes in both the frequency and amplitude of the breath. Similarly, there are advantages in the method of calculating a baseline respiratory airflow by a moving median as compared to calculating a moving mode. For example, differences in breathing patterns may have more effect on a moving mode. The use of airflow in determining respiratory events is not common, as typically it is not a reliable and accurate signal. According to the methods provided herein, the accuracy and reliability are increased by the calculation of a reliable baseline airflow from which the onset and end of breath can be determined. Additionally, respiratory airflow detected separately from each of the subject's nares can be more accurate as it takes into account naris-specific changes in airflow that are known to occur throughout the night. Additionally, the use of airflow in the detection of respiratory events during an oral appliance titration can be more complete and reliable because the titration device impedes respiratory airflow through the mouth. Accordingly, air taken in through the subject's nose has difficulty escaping through the subject's mouth, which makes the detected respiratory airflow more complete and reliable.

As discussed above, a respiratory event is classified if the oxygen saturation event is detected within the predetermined time lag (e.g., a fixed or customized time lag) after the respiratory airflow event is detected. Optionally, the predetermined time lag can be fixed for all subjects. For example, the predetermined time lag can be between approximately 10-40 seconds (e.g., 25±15 seconds). Optionally, the predetermined time lag, or the period of time between matched oxygen saturation and respiratory airflow events, can be subject-specific. The time lag can optionally be customized in terms of its range (e.g., the width of the correlation period) and the value of its midpoint (e.g., the position of the correlation window). The value of the midpoint determines the interval of time between the oxygen saturation event and the preceding respiratory airflow event and the range, evenly distributed on both sides of the midpoint, determines the time window in which the preceding respiratory airflow event must be located (i.e., occur) in order to be correlated with the subsequent oxygen saturation event. For example, the customized time lag can be a time lag that provides the greatest number of matched respiratory events between oxygen saturation events and airflow events collected during a time period. For example, the customized time lag can be identified by summing the number of respiratory events detected during each fixed time interval for varying midpoint values of lag time. For example, calculating the number of events with a 30 second range on either side (e.g., ±15 seconds) of starting value and comparing it with the number of events during the same 30 second window at successive positions (e.g., starting time interval plus 1 second, 2 second, 3 seconds, etc.), identifying the position of time with the greatest number of respiratory events and accepting a range on either side of the identified interval of time (e.g., ±15 seconds, for example). For example, a time interval of 30 seconds may be initially selected. The number of events detected with a matching time interval from 5 seconds to 35 seconds would be compared with the number of events detected with a matching time interval from 6 to 36 seconds, 7 to 37 seconds, etc. and the interval with the greatest number of respiratory events would be accepted. Determination of the customized time lag could also involve changing the width of the correlation window. It should be understood that the customized time lag can be used in real-time analysis of the respiratory events or offline when re-scoring the respiratory events in the data collected with a fixed time lag for use in the prediction algorithms discussed herein. Additionally, the fixed time lag can optionally be used in a first phase of data collection and then the customized time lag can be used in a second phase of data collection. For example, the customized time lag can be determined in a first night and then utilized in a second night, or the customized time lag can be determined in a first portion of the test period and then utilized in the second portion of the same test period. The customized time lag can optionally be calculated off line or in real time. Alternatively, the predetermined time lag can be customized for an individual subject by collecting data using a fixed time lag and then analyzing the respiratory response to determine the customized time lag. The analysis can be performed before conducting a titration for oral appliance therapy on the subject. Alternatively or additionally, the analysis can be performed while conducting a titration for oral appliance therapy on the subject.

Figure 2B:
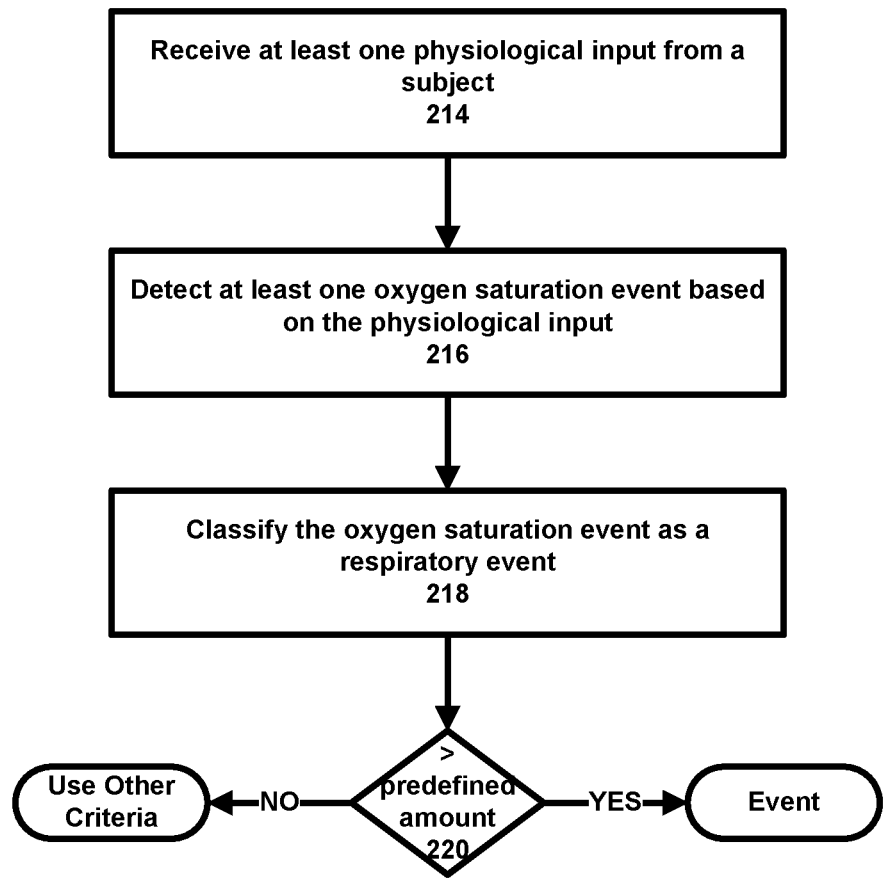

Referring now to FIG. 2B, a flow diagram illustrating example operations 200B for detecting respiratory events is shown. Specifically, FIG. 2B illustrates example operations 200B for defining and measuring a respiratory event using oxygen saturation. For example, a respiratory event can optionally be classified based only on a large decrease in oxygen saturation from real-time or baseline oxygen saturation. At 214, at least one physiological input can be received from a subject. The physiological input can be oxygen saturation, for example. At 216, at least one oxygen saturation event is detected based on the received physiological input. Then, at 218, the oxygen saturation event is classified as a respiratory event. In particular, at 220, a determination as to whether a decrease in oxygen saturation exceeds at least a predefined amount from real-time or baseline oxygen saturation. For example, the predefined amount can be approximately 6%. If YES, the oxygen saturation event is classified as a respiratory event. If NO, it is not possible to detect a respiratory event using only oxygen saturation. Optionally, respiratory events can be detected using other predetermined criteria. For example, respiratory events can be define and measured using predetermined criteria including a combination of oxygen saturation and respiratory airflow as discussed above with regard to FIG. 2A.

Figure 2C:
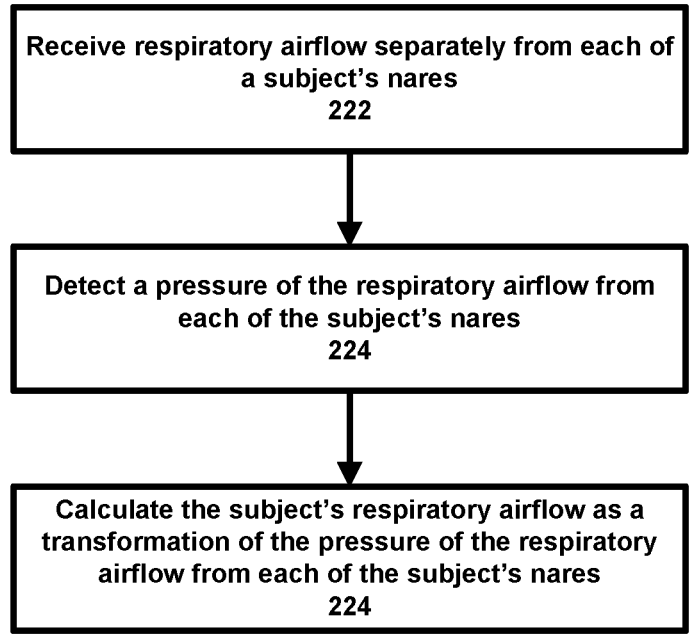
FIG. 2C is a flow diagram illustrating example operations for assessing respiratory airflow in a subject.

Referring now to FIG. 2C, a flow diagram illustrating example operations 200C for assessing respiratory airflow in a subject is shown. As discussed above, respiratory airflow can be detected using nasal prongs that detect pressure in the subject's nasal airstream. For example, a cannula having separate tubes for each of the subject's nares can be used to collect respiratory airflow separately from each of the subject's nares. The recorded pressure can be an absolute pressure (e.g., pressure minus baseline pressure) in the subject's nasal airstream, for example. At 222, respiratory airflow can be separately collected from each of the subject's nares. At 224, a pressure signal from each of the subject's nares can be detected. Then, at 226, the subject's respiratory airflow can be calculated as a transformation of the pressure signals received separately from each of the subject's nares. For example, the transformation can be a sum of a square root of a pressure signal (e.g., absolute pressure) separately collected from each of the subject's nares. The calculated respiratory airflow can be used to estimate peak respiratory airflow, breath-by-breath minute ventilation or any other useful measure. The respiratory airflow can be used to detect a respiratory airflow event, used in the detection of a respiratory event, or may be used to assess the effect of repositioning the mandible.

Alternatively or additionally, detecting a respiratory event can include detecting an occurrence of inspiratory flow limitation. This occurrence can be determined by comparison to parameters established using a neural network trained against a gold standard. The inputs can include at least one of oxygen saturation, respiratory airflow, acoustic energy (sound) and vibration energy or combinations thereof.

Controlling a Protrusion Level of the Titration Device

As discussed herein, controlling a protrusion level includes repositioning a subject's mandible relative to the maxilla in at least one degree of freedom. For example, the subject's mandible can be moved in the anterior-posterior direction relative to the maxilla. Additionally, controlling a protrusion level includes repositioning the subject's mandible relative to the maxilla in two, three, four, five or six degrees of freedom. For example, the subject's mandible can be moved relative to the maxilla by adjusting the amount of bite opening (e.g., rotation of the mandible around the condyle) and/or separation of the teeth (e.g., parallel separation of the condyle). For multidimensional titration, a titration device can be used to adjust the position of the mandible in a plurality of degrees of freedom. For example, in addition to adjusting the protrusion level of the mandible in the anterior-posterior direction, the position can be adjusted for separation between the occlusal surfaces of the teeth and can also be adjusted for the amount of bite opening. In these instances the therapeutic position, or clinically-beneficial orientation, is optionally described in multiple variables, and the therapeutic zone, including the clinically-beneficial orientation, is optionally provided as a three dimensional map.

As discussed above, it is possible to alter the protrusive distance of the mandible relative to the maxilla in the anterior-posterior direction (e.g., translation of the mandible relative to the maxilla in the anterior-posterior direction). Protrusion of the mandible relative to the maxilla in the anterior-posterior direction lengthens anterior pharyngeal muscles and tends to open the pharynx.

It is also possible to alter and maintain the bite opening of the subject, which is a rotational movement of the mandible around the condyle. This rotation opens the bite and displaces the mandible posteriorly and caudally, which has implications for the treatment of sleep apnea as a number of pharyngeal muscles (e.g., genioglossus, geniohyoid, stylosglossus, etc.) either directly or indirectly attach to an anterior region of the mandible. The effects of the mandible's rotation on the mechanics of the passive pharynx demonstrate that rotation increases closing pressure and reduces maximum cross-sectional area of the airway.

While the temporomandibular (T-M) joint has two primary movements (e.g., translation (or protrusion) and rotation), a smaller form of vertical adjustment is also optionally used. Parallel separation (e.g., caudal movement of the condyle in the absence of translation) is limited (e.g., 1 to 3 mm, for example) and a small separation of the T-M joint surface represents the normal, unloaded condition of the joint. Thus, in the mandibular protruded situation, the joint surfaces should be separated. This is particularly important during long term position or bruxism, when loading of the T-M joint by apposition of the surfaces may cause pain and produce joint deterioration. This movement provides additional space for the tongue.

Therefore, repositioning in any of these three dimensions (e.g., protrusion, bite opening or parallel separation) has therapeutic effect. It should be understood that each of these three dimensions can be independently considered in determining the predetermined clinically-beneficial orientation.

Systems and methods are provided herein for automatically controlling a titration device such as the adjustable mandibular displacement device 10 discussed with regard to FIG. 1A. Example implementations are provided with respect to the adjustable mandibular displacement device 10. It should be understood that this disclosure contemplates that the protrusion level of other titration devices can also be controlled. For example, the adjustable mandibular displacement device 10 can be an automatically-controlled mandibular protruder. An automatically-controlled mandibular protruder can be dynamically adjusted without having a technician manually adjust the mandibular displacement device locally (e.g., at or adjacent to the subject's oral cavity) and can be dynamically adjusted without technician control or can be dynamically adjusted by a technician with automatically generated prompts that help the technician guide the titration.

Figure 3:
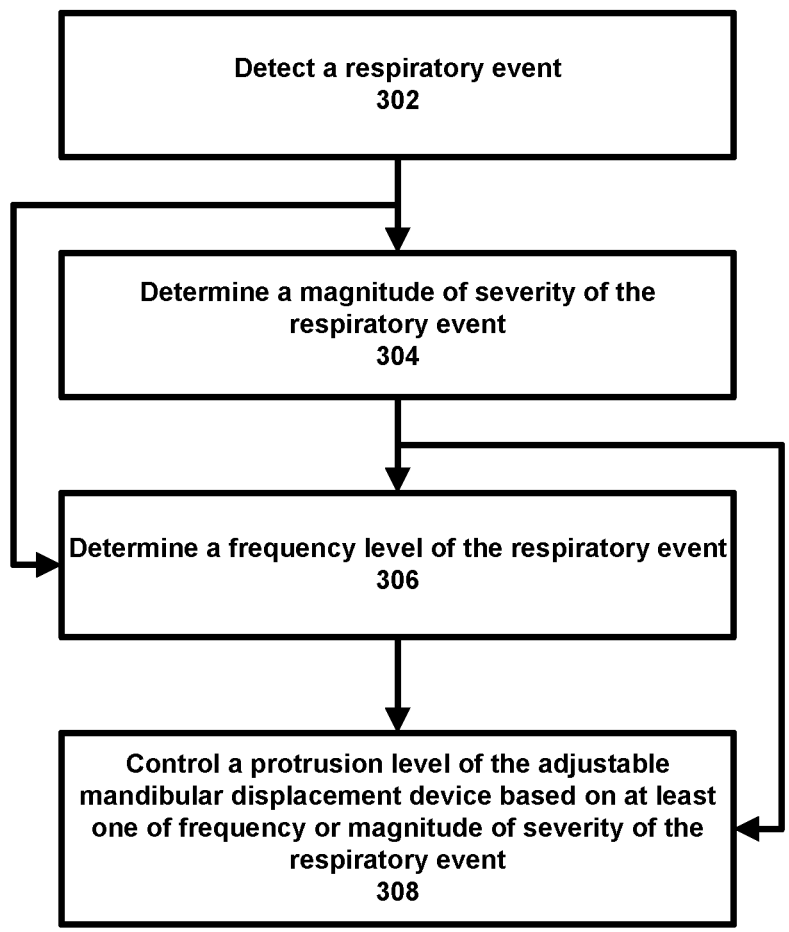
FIG. 3 is a flow diagram illustrating example operations for controlling a protrusion level of the adjustable mandibular displacement device based on frequency or severity of respiratory events.

Optionally, controlling a protrusion level of the adjustable mandibular displacement device can include adjusting the protrusion level of the adjustable mandibular displacement device based on at least one of frequency or severity of one or more respiratory events. For example, the protrusion level can be dynamically and automatically controlled (e.g., in real-time) during a titration based on the frequency or severity of the respiratory events. Alternatively or additionally, a protrusion level of the adjustable mandibular displacement device can be controlled to induce one or more respiratory events or to induce a change in respiratory airflow. Alternatively or additionally, a protrusion level of the adjustable mandibular displacement device can be controlled to optimize a protrusion level. Referring now to FIG. 3, a flow diagram illustrating example operations 300 for controlling a protrusion level of the adjustable mandibular displacement device based on frequency or severity of respiratory events is shown. It should be understood that controlling a protrusion level of the adjustable mandibular displacement device can include at least one of increasing or decreasing the protrusion level of the adjustable mandibular displacement device. For example, at 302, a respiratory event can be detected. Detection of respiratory events is discussed in detail above. For example, detecting a respiratory event can include defining and measuring physiological information from a subject against predetermined criteria. At 304, a magnitude of severity of the respiratory event can be determined. The magnitude of severity can be calculated by assessing the severity of one or both of airflow event and an oxygen event. Alternatively or additionally, a frequency of respiratory events (e.g., respiratory events/unit time) can be calculated. Optionally, a frequency of respiratory events of each magnitude of severity can be determined. And, at 306, a frequency level of the respiratory event can be determined. At 308, the protrusion level of the adjustable mandibular displacement device can be controlled based on at least one of the magnitude of severity or frequency of the respiratory event. For example, at least one of a magnitude and rate of adjustment can be related to at least one of frequency or magnitude of severity of the respiratory event. Alternatively or additionally, both the magnitude and rate of adjustment can be related to at least one of a frequency or magnitude of severity of the respiratory event. The magnitude of adjustment is the amount (e.g., number of millimeters) the protrusion level of the adjustable mandibular displacement device is adjusted. For example, the protrusion level can be adjusted by 5 mm in response respiratory events of a given severity and/or frequency level. The rate of adjustment defines how fast (or slow) the protrusion level of the adjustable mandibular displacement device is adjusted. For example, the protrusion level can be adjusted by 5 mm after a period of delay, for instance a 1 minute delay, or alternatively without a period of delay in response respiratory events of the given severity and/or frequency level. In particular, a higher magnitude or rate of adjustment can correspond to a more frequent or severe respiratory event, and a lower magnitude or rate of adjustment can correspond to a less frequent or severe respiratory event. Accordingly, it is possible to adjust the protrusion level rapidly through protrusion levels at which more severe or frequent respiratory events are occurring and settle at a larger protrusion level range where less severe or frequent respiratory events occur. Then, it is optionally possible to optimize the protrusion level within the protrusion level range where less severe or frequent respiratory events occur. The optimization may be done by monitoring and adjusting for the magnitude of airflow.

The magnitude of the severity of the one or more respiratory events can optionally be determined as discussed below. The magnitude of severity can optionally be classified into one of a plurality of predetermined categories. For example, when the physiological inputs from the subject include oxygen saturation and respiratory airflow, oxygen saturation events and respiratory airflow events can be identified, and oxygen saturation events can be matched with corresponding respiratory airflow events to identify respiratory airflow events. The categories therefore can include a plurality of categories related to a severity of the oxygen saturation event and a plurality of categories related to a severity of the respiratory airflow event. For example, a decrease in oxygen saturation associated with the respiratory event can be classified into one of n categories, and a decrease in respiratory airflow associated with the respiratory event can be classified into one of m categories. The magnitude of the severity of a respiratory event can be determined using an n×m matrix based on the severities of the decrease in oxygen saturation and the decrease in respiratory airflow associated with the respiratory event, where n and m are integers >1. At least one of a magnitude and a rate of adjustment of the protrusion level can be controlled based on the magnitude of the severity determined using the n×m matrix.

For example, there can be three categories for a severity level of the respiratory airflow event (e.g., m=3). A first category can correspond to approximately an 80-100% decrease in respiratory airflow. A second category can correspond to approximately a 45-79% decrease in respiratory airflow. A third category can correspond to approximately a 30-44% decrease in respiratory airflow. A decrease in respiratory airflow that does not fall within one of the categories above, for example a decrease of less than approximately 30%, is not registered as a respiratory airflow event and is considered a normal fluctuation in breathing. Alternatively or additionally, there can be three categories for a magnitude of severity of the oxygen saturation event (e.g., n=3). A first category can correspond to an approximately 6% or greater decrease in oxygen saturation from real-time or baseline oxygen saturation. A second category can correspond to an approximately 3-6% decrease in oxygen saturation from real-time or baseline oxygen saturation. A third category can correspond to an approximately less than 3% decrease in oxygen saturation from real-time or baseline oxygen saturation. It should be understood that the values of m and n, as well as the values for each of the categories, are provided only as examples, and that other values can be used.

Additionally, the frequency level of the one or more respiratory events can optionally be determined. The frequency level of the one or more respiratory events can be used to determine at least one of the magnitude and rate of adjustment of the adjustable mandibular displacement device. For example, a magnitude of the severity of the respiratory event can be determined as discussed above (e.g., using the n×m matrix). Optionally, a frequency at which the respiratory event occurs is calculated. The frequency at which the respiratory event occurs can be multiplied by the magnitude of the severity level of the respiratory event to obtain a frequency-severity index. The protrusion level of the adjustable mandibular displacement device can be controlled based on the frequency-severity index. Optionally, the frequency of respiratory events having substantially the same magnitude of severity are determined and then multiplied by the magnitude of severity to obtain a frequency-severity index. A global frequency-severity index can be calculated by summing the frequency-severity indexes for a plurality of respiratory events. The protrusion level of the adjustable mandibular displacement device can be controlled during the test period based on the global frequency-severity index.

Alternatively or additionally, a frequency level of the respiratory event can be classified into one of q categories and a frequency-severity index can be obtained using an n×m×q matrix based on the severity and frequency levels associated with the respiratory event, where n and m and q are integers >1. The protrusion level of the adjustable mandibular displacement device can be controlled based on the frequency-severity index.

Automated Titration for Oral Appliance Therapy

Figure 4:
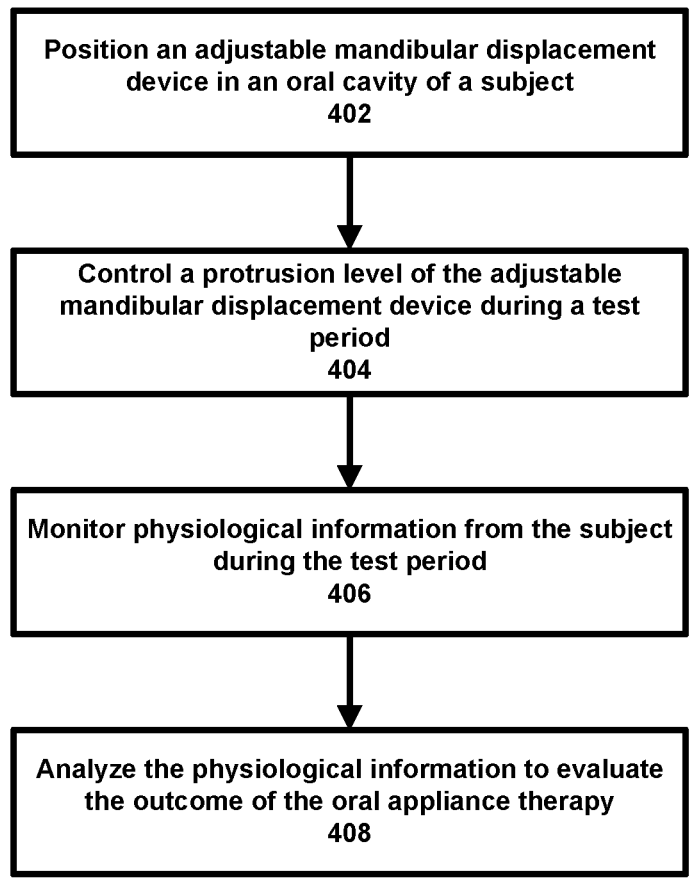
FIG. 4 is a flow diagram example operations for evaluating an outcome of oral appliance therapy is shown.

Referring now to FIG. 4, a flow diagram 400 illustrating example operations for evaluating an outcome of oral appliance therapy in a subject is shown. At 402, an adjustable mandibular displacement device can be positioned in an oral cavity of the subject. After placing the adjustable mandibular displacement device, an automatic titration protocol can be implemented. At 404, a protrusion level of the adjustable mandibular displacement device can be controlled during a test period. At 406, physiological information from the subject is monitored during the test period. The monitored physiological information can be recorded in the memory of a computing device, for example, to facilitate the analysis described below. For example, the physiological information can include respiratory airflow and oxygen saturation. The physiological information can also include other information related to a subject including, but not limited to acoustic energy or vibration generated by the subject, sleep position, sleep stage or force applied to a subject's teeth, including combinations thereof. Then at 408, the physiological information is analyzed to evaluate the outcome of oral appliance therapy.

Optionally, the evaluation can be a prediction of whether the subject is a favorable candidate for oral appliance therapy. Alternatively or additionally, the evaluation can optionally be an indication of an effective protrusion level of the adjustable mandibular displacement device. Alternatively or additionally, the evaluation can optionally be an indication of an optimal effective protrusion level of the adjustable mandibular displacement device.

The protrusion level of the adjustable mandibular displacement device can optionally be controlled during the test period based on analyzing the physiological information. Additionally, analyzing the physiological information can include processing the physiological information using a computing device. Optionally, the physiological information is analyzed to detect one or more respiratory events. For example, the relationship between one or more of components of the physiological information can be analyzed to detect (identify, classify, etc.) a respiratory event using predetermined criteria, for example, according to any of the methods discussed herein. Detection of respiratory events is discussed in detail above. For example, detecting a respiratory event includes defining and measuring physiological information from a subject against predetermined criteria. A respiratory event is more than mere evidence of obstruction (e.g., a change in respiratory airflow, oxygen saturation, snoring sound, etc.).

For example, a frequency of occurrence of the one or more respiratory events can be calculated. If the frequency of occurrence is greater than a predetermined threshold, a protrusion level of the adjustable mandibular displacement device can be controlled by increasing the protrusion level of the adjustable mandibular displacement device. The protrusion level can be increased until the frequency of occurrence of the one or more respiratory events is less than the predetermined threshold. The protrusion level can therefore be increased to minimize and/or eliminate occurrence of respiratory events to an acceptable level. Optionally, at least one of a magnitude and rate of adjustment of the protrusion level can be controlled based on frequency or severity of the respiratory events as discussed herein. Accordingly, the predetermined threshold can be selected such that the adjustable mandibular displacement device is controlled to minimize and/or eliminate respiratory events to an acceptable level when the frequency of occurrence exceeds the predetermined threshold.

Alternatively or additionally, if the frequency of occurrence of the one or more respiratory events is less than a predetermined threshold, a protrusion level of the adjustable mandibular displacement device can be controlled to optimize respiratory airflow or another physiologic input (e.g., snoring) as discussed herein. For example, a first protrusion level beyond which a decrease in the protrusion level results in a decrease respiratory airflow can be identified. For example, the first protrusion level can be a minimum protrusion level ($P_{crit}$), where a further decrease in protrusion level results in a decrease in respiratory airflow. Optionally, the average breath-by-breath minute ventilation for one or more breaths before a change in protrusion level can be compared to the average breath-by-breath minute ventilation for one or more breaths after the change in protrusion level to determine how the change in protrusion level effected respiratory airflow. Optionally, a similar comparison can be performed using peak respiratory airflow. Additionally, a second protrusion level beyond which an increase in the protrusion level does not result in an increase in respiratory airflow can also be identified. For example, the second protrusion level can be an optimal protrusion level ($P_{opt}$), where a further increase in protrusion level does not result in an increase in respiratory airflow. Optionally, the average breath-by-breath minute ventilation for one or more breaths before a change in protrusion level can be compared to the average breath-by-breath minute ventilation for one or more breaths after the change in protrusion level to determine how the change in protrusion level effected respiratory airflow. Optionally, a similar comparison can be performed using peak respiratory airflow. An effective protrusion level for oral appliance therapy can be approximately between the first protrusion level and the second protrusion level. Alternatively or additionally, a third protrusion level where a small increase in the protrusion level results in an insignificant change in respiratory airflow and a small decrease in the protrusion level results in a signification change in respiratory airflow can be identified. This response is known as attractor behavior, which is discussed in detail below. Optionally, an effective protrusion level for oral appliance therapy can be approximately the third protrusion level. Optionally, a protrusion level of the adjustable mandibular displacement device during the test period can be controlled in response to not detecting a respiratory event during a fixed period of time in order to induce a respiratory event or to induce a change in respiratory airflow.

Titrating Based on a Comprehensive Data Set

Figure 5A:
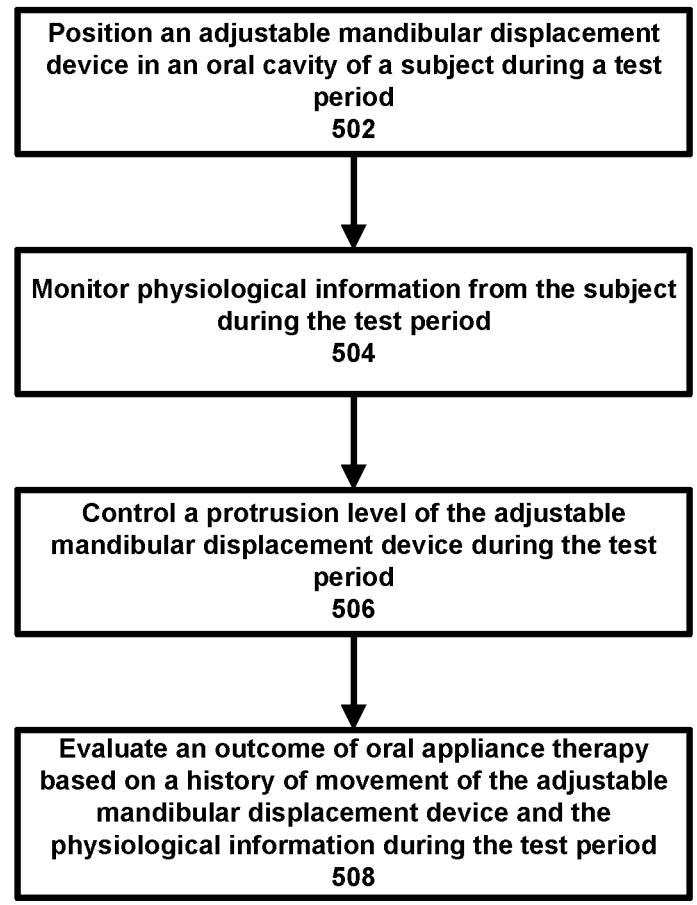
FIG. 5A is a flow diagram illustrating example operations for performing a titration for oral appliance therapy using a comprehensive data set.

Referring now to FIG. 5A, a flow diagram illustrating example operations 500A for performing a titration for oral appliance therapy using a comprehensive data set is shown. By performing a titration for oral appliance therapy using a comprehensive data set, the overall response at various protrusion levels during a test period is examined in order to evaluate therapeutic outcome. For example, as discussed below, respiratory events are detected, and in some cases even induced, and classified. Then, the protrusion level of the titration device is dynamically controlled in response to the respiratory events. The protrusion level can be controlled using a graded dynamic adjustment (e.g., magnitude and rate) according to the classified respiratory events. Therapeutic outcome can then be evaluated based on the overall data set, which includes, but is not limited to, the physiological response of the subject and information regarding the dynamic response of the titration device (e.g., how fast and how far the titration device moves during the test period).

For example, at 502, an adjustable mandibular displacement device can be positioned in an oral cavity of a subject during a test period. At 504, physiological information from the subject is monitored and recorded during the test period. For example, the physiological information can include respiratory airflow and oxygen saturation. The physiological information can also include other information related to a subject including, but not limited to, acoustic energy or vibration generated by the subject, sleep position, sleep stage or force applied to a subject's teeth, including combinations thereof. Additionally, at 506, a protrusion level of the adjustable mandibular displacement device can be controlled and recorded during the test period. The protrusion level of the adjustable mandibular displacement device can be controlled according to any of the methods discussed herein. For example, the adjustable mandibular displacement device can be controlled to reduce the frequency of respiratory events to an acceptable level. Alternatively or additionally, the adjustable mandibular displacement device can be controlled based on severity or frequency of the respiratory events. Optionally, the adjustable mandibular displacement device can be controlled to optimize airflow. The physiological information from 504 is recorded in relation to the protrusive level at which it was detected, as recorded in 506. Temporal data for each of 504 and 506 is similarly recorded. At 508, the outcome of oral appliance therapy is evaluated based on a history of movement of the adjustable mandibular displacement device and the physiological information during the test period. For example, as discussed herein, the evaluation can be a prediction of whether the subject is a favorable candidate for oral appliance therapy. Alternatively or additionally, the evaluation can optionally be an indication of an effective protrusion level of the adjustable mandibular displacement device. An effective protrusion level of the adjustable mandibular displacement device can be a protrusion level that reduces the severity or frequency of respiratory events to an acceptable level. Alternatively or additionally, the evaluation can optionally be an indication of an optimal effective protrusion level of the adjustable mandibular displacement device.

As discussed above, the monitored physiological information can include, but is not limited to, acoustic energy or vibration generated by the subject, sleep position, sleep stage or force applied to a subject's teeth, including combinations thereof. For example, monitoring physiological information from the subject can include receiving one or more physiological inputs from the subject during the test period and detecting one or more respiratory events during the test period using the one or more physiological inputs. Detection of respiratory events is discussed in detail above. For example, detecting a respiratory event includes defining and measuring physiological information from a subject against predetermined criteria. A respiratory event is more than mere evidence of obstruction (e.g., a change in respiratory airflow, oxygen saturation, snoring sound, etc.). The one or more respiratory events discussed herein can be an apnea, a hypopnea, a flow limited breath, a snoring event, etc.

As discussed herein, a history of movement includes information associated with a position and/or orientation of a titration device during a titration. The titration device can be the adjustable mandibular displacement device 10 discussed above with regard to FIG. 1A, for example. In other words, the history of movement includes information associated with a position and/or orientation (including a plurality of positions and/or orientations) at one or more discrete times during the titration. Time can optionally be measured in seconds, minutes, hours, or any fraction thereof. The position and/or orientation of the mandibular displacement device can be measured as an amount of protrusion in the anterior-posterior direction, an amount of occlusal separation in the cranial-caudal direction and/or an amount of bite opening. Thus, the information can include position and/or orientation of the titration device as a function of time during the titration. The information can also include a total amount of time the titration device spends at, greater than or less than each of a plurality of positions and/or orientations. Further, the information can include a rate of movement of the titration device between positions and/orientations.

Additionally, when evaluating an outcome of oral appliance therapy based on a comprehensive data set, changes in a protrusion level of the adjustable mandibular displacement device can be monitored during the test period. For example, changes in the protrusion level can be monitored and/or stored using the mandibular displacement device controller 40 and/or the computing device 50 discussed above with regard to FIG. 1B. The changes in the protrusion level of the adjustable mandibular displacement device can define the history of movement of the adjustable mandibular displacement device. Optionally, the history of movement of the adjustable mandibular displacement device can include movement between at least two protrusion levels. Additionally, the history of movement can include an amount of time the adjustable mandibular displacement device spends at each of the at least two protrusion levels.

Optionally, a frequency of respiratory events (e.g., respiratory events/unit time) can be calculated. Detection of respiratory events is discussed in detail above. For example, detecting a respiratory event includes defining and measuring physiological information from a subject against predetermined criteria. It should be understood that during a titration (e.g., in real-time), the frequency of respiratory events can be calculated as the number of respiratory events occurring per unit time. Additionally, it should also be understood that it is possible to calculate a frequency of respiratory events that occurred at a plurality of protrusion levels at a later time using a data set collected during the titration. For example, a number of respiratory events at or above (i.e., at or greater than) each of the plurality of protrusion levels can be determined. Each of the number of respiratory events can then be divided by an amount of time at or above each of the plurality of protrusion levels. This frequency can define a Residual Respiratory Disturbance Index ("Residual RDI"). The Residual RDI is shown below in Eqn. (1).

$$\text{Residual } RDI(i) = \frac{\text{\# Respiratory Events at or above Protrusion Level}(i)}{\text{Amount of Time at or above Protrusion Level}(i)}, \quad (1)$$

where i is a discrete protrusion level of the adjustable mandibular displacement device. Optionally, the Residual RDI can be calculated at a plurality of protrusion levels where an amount of time at or above each of the plurality of protrusion levels is at least 5 minutes. In other words, the Residual RDI may optionally not be calculated at protrusion levels where the adjustable mandibular displacement device does not spend a significant amount of time at or above the protrusion level.

Optionally, the history of movement can be analyzed to determine a percentage of time the adjustable mandibular displacement device spends at or below (i.e., at or less than) each of the at least two protrusion levels. For example, the percentage of time at or below each of the protrusion levels can be an amount of time spent at or below each of the plurality of protrusion levels divided by a total amount of time in the test period, which is shown below in Eqn. (2).

$$\% \text{ of Time}(i) = \frac{\text{Amount of Time at or below Protrusion Level}(i)}{\text{Total Amount of Time in the Test Period}}, \quad (2)$$

where i is a discrete protrusion level of the adjustable mandibular displacement device.

Additionally, evaluating an outcome of oral appliance based on a comprehensive data set can include identifying at least one effective protrusion level. For example, evaluating an outcome of oral appliance therapy can include identifying one or more of the plurality of protrusion levels where the frequency of respiratory events is less than the predefined value. Optionally, the frequency of respiratory events can be the Residual RDI discussed above, for example. The predefined value can represent an acceptable frequency of respiratory events per unit time. For example, the predefined value can be an acceptable number of events per hour such as 10 events per hour. The predefined value can be a clinically-acceptable number of events per hour or a subject-specific-acceptable number of events per hour. Thus, it should be understood that the acceptable number of events per hour can be more or less than 10. Optionally, the predefined value can be determined based on physiological measurements made before or during the test period. For example, the predefined value can be an acceptable number of events per hour in addition to a percentage reduction from a baseline number determined when the subject is not receiving therapy, such as a 50% reduction from baseline number of respiratory events. In other words, therapeutic success can optionally be defined as requiring: (i) an acceptable number of events per hour and (ii) a percentage reduction from the baseline number of events per hour. A protrusion level where the frequency of respiratory events is less than the predefined value can be considered an effective protrusion level for oral appliance therapy because the frequency of respiratory events are reduced to an acceptable level. It should also be understood that a value or range representing a nearly-acceptable number of events per unit time can be established such as 15 or 20 events per hour, for example. Accordingly, a subject can be considered a favorable candidate for oral appliance therapy when the frequency of respiratory events is less than the predefined value. Alternatively, the predefined value can be subject specific. For example, an acceptable number of events per hour can be less than half of the number of events per hour displayed by a subject without therapy, such as would be measured in a baseline study. Additionally, the protrusion level where the frequency of respiratory events is less than the predefined value can be considered the effective protrusion level for oral appliance therapy. On the other hand, a subject can be considered an unfavorable candidate for oral appliance therapy when the frequency of respiratory events is greater than the predefined value for every level of protrusion. The subject can therefore be labeled as a predicted failure when there is no protrusion level where the frequency of respiratory events is less than the predefined value. In addition, a subject can be considered a nearly-favorable candidate for oral appliance therapy when the frequency of respiratory events is less than the value representing a nearly-acceptable frequency of respiratory events. Optionally, a subject can be considered inconclusive when the test period is too short to collect sufficient data and/or the titration device does not spend sufficient time near its upper limit.

Additionally, evaluating an outcome of oral appliance based on a comprehensive data set can include determining whether a percentage of time at or below the at least one effective protrusion level is greater than or equal to a predefined percentage of time. A similar determination can include determining whether a percentage of time at or above the at least one effective protrusion level is less than or equal to a predefined percentage of time. It should be understood that the predefined percentages of time in the cases above would be different but the outcome of the determination would be the same. As discussed above, the history of movement can be analyzed to determine a percentage of time the adjustable mandibular displacement device spends at or below each of a plurality of protrusion levels. A determination can then be made as to whether the percentage of time at or below each of the one or more protrusion levels is greater than or equal to a predefined percentage of the test period. For example, the predefined percentage of the test period can be a majority of the test period. The predefined percentage can be between 75% and 100% such as 85% of the test period, which represents more than a majority of the test period. Accordingly, a subject can optionally be considered a favorable candidate for oral appliance therapy when there is at least one protrusion level for which the frequency of respiratory events is less than the predefined value and the percentage of time is greater than the predefined percentage of time. Additionally, the protrusion level where the frequency of respiratory events is less than the predefined value and the percentage of time is greater than the predefined percentage of time can be considered the effective protrusion level for oral appliance therapy. On the other hand, a subject can optionally be considered an unfavorable candidate for oral appliance therapy when the frequency of respiratory events is greater than the predefined value and/or and the percentage of time is less than the predefined percentage of time.

In addition, it should be understood that there may be more than one protrusion level where the frequency of respiratory events is less than the predefined value. In other words, there can be more than one protrusion level where the frequency of respiratory events are reduced to an acceptable level. In this case, an effective protrusion level for oral appliance therapy can be a smallest protrusion level (e.g., a minimum protrusion level) where the frequency of respiratory events is less than the predefined value and the percentage of time is greater than or equal to the predefined percentage of the test period. Accordingly, the effective protrusion level for oral appliance therapy can be the minimum protrusion level where the frequency of respiratory events are reduced to an acceptable level and where the adjustable mandibular displacement device spends a majority of the test period.

Figure 6A:
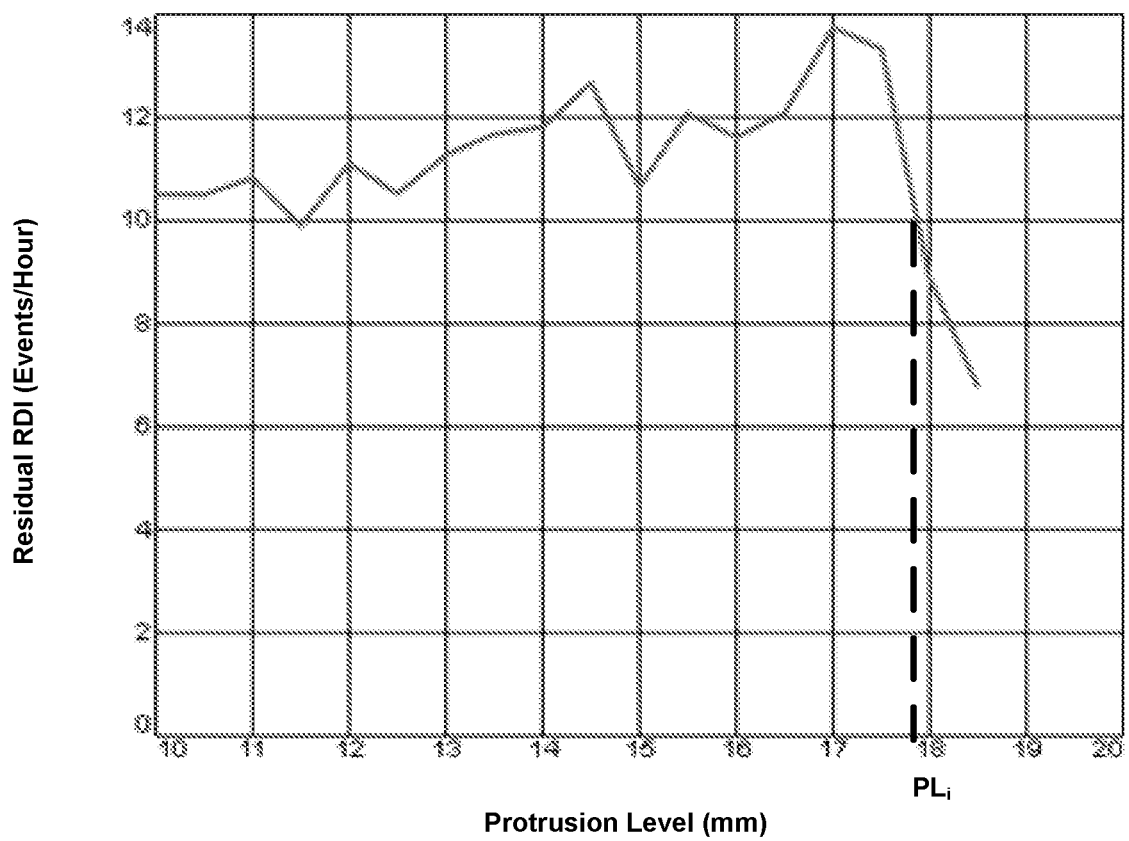
FIG. 6A is a graph illustrating the frequency of respiratory events occurring at or above each of a plurality of protrusion levels.

Optionally, a graphical representation of the frequency of respiratory events at or above each of a plurality of protrusion levels such as the Residual RDI, for example, and/or a graphical representation of the percentage of time at or below each of a plurality of protrusion levels can be generated. Additionally, evaluating an outcome of oral appliance therapy based on a comprehensive data set can be performed using the graphical representation. For example, a determination of whether a subject is a favorable candidate for oral appliance therapy and/or an effective protrusion level can be made using the graphical representation. Referring now to FIG. 6A, a graph illustrating the frequency of respiratory events at or above each of a plurality of protrusion levels is shown. The graph illustrates the Residual RDI (e.g., respiratory events per unit time) versus protrusion level (e.g., mm of protrusion). As shown in FIG. 6A, at approximately $PL_i=17.9$ mm, the Residual RDI is less than 10 respiratory events per hour, which can optionally be the predefined value of events per unit time representing an acceptable frequency of respiratory events, as discussed above. Accordingly, the subject can be considered a favorable candidate for oral appliance therapy because the Residual RDI is less than the predetermined value (e.g., at $PL_i=17.9$ mm). In other words, a protrusion level that reduces occurrence of respiratory events to an acceptable level exists. For example, in FIG. 6A, the effective protrusion level is $PL_i=17.9$ mm. It should be understood that the graph of the Residual RDI versus protrusion level is subject-specific and generated following a titration. Accordingly, the one or more effective protrusion levels are also subject-specific.

Figure 6B:
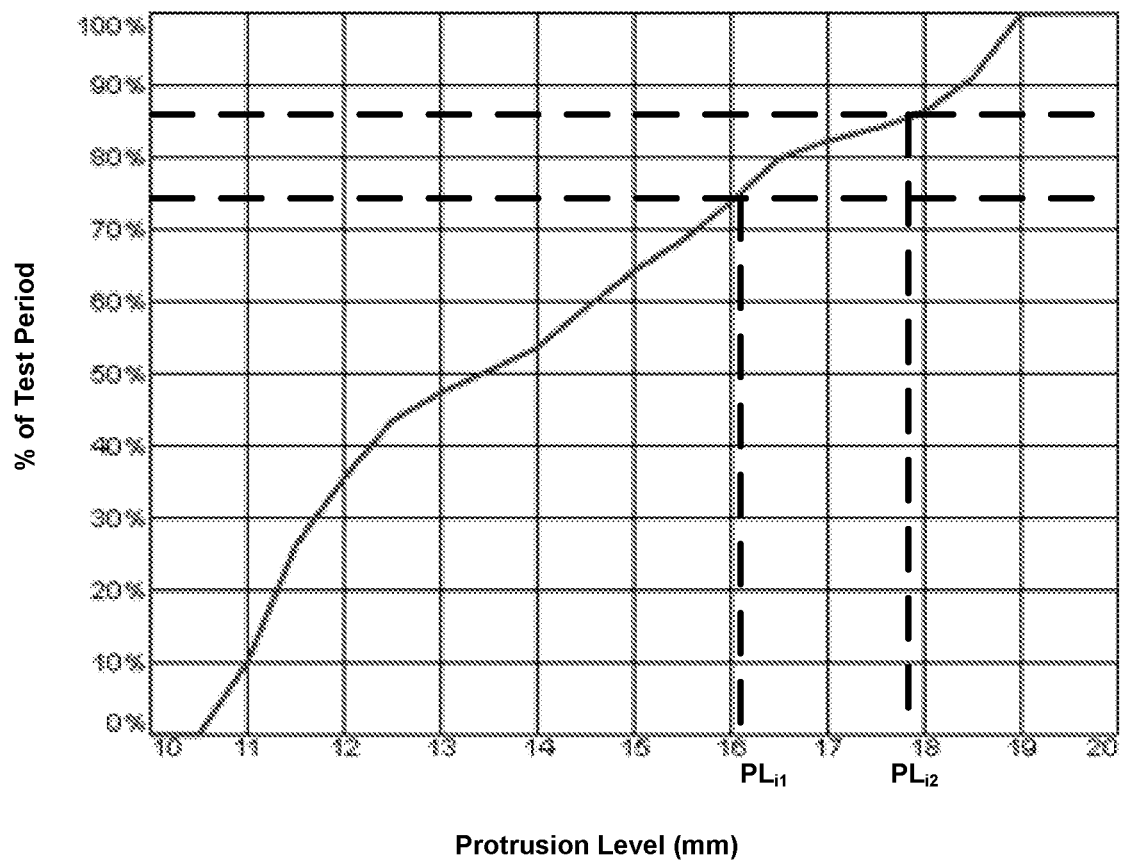
FIG. 6B is a graph illustrating the percentage of time the adjustable mandibular displacement device spends at or below each of a plurality of protrusion levels.

Referring now to FIG. 6B, a graph illustrating the percentage of time at or below each of a plurality of protrusion levels is shown. As discussed above, the subject can be considered a favorable candidate for oral appliance therapy when the frequency of respiratory events (e.g., the Residual RDI) is less than a predefined value (e.g., 10 events per hour, for example) and the percentage of time at or below the given protrusion level is greater than a predetermined percentage of the test period. The predetermined percentage can be a majority of the test period, such as between 75% and 100% of the test period, for example. In FIG. 6B, protrusion levels greater than approximately $PL_{i1}=16.1$ mm represent protrusion levels where the adjustable mandibular displacement device spends greater than 75% of the test period at or below the given protrusion level. Additionally, as shown in FIG. 6B, the adjustable mandibular displacement device spends greater than approximately 87% of the test period at approximately $PL_{i2}=17.9$ mm or less. $PL_{i2}=17.9$ mm also represents the protrusion level where the Residual RDI is less than 10 respiratory events per hour shown in FIG. 6A. Accordingly, the subject can be considered a favorable candidate for oral appliance therapy the Residual RDI is less than the predetermined value (e.g., at $PL_{i2}=17.9$ mm) and the percentage of time at or below $PL_{i2}=17.9$ mm is greater than the predefined percentage of time. In other words, a protrusion level that reduces occurrence of respiratory events to an acceptable level exists. For example, in FIGS. 6A-6B, the effective protrusion level is $PL_{i2}=17.9$ mm. It should be understood that the graph of the percentage of time is subject-specific and generated following a titration. Accordingly, the percentage of time is also subject-specific.

When evaluating an outcome of oral appliance therapy based on a comprehensive data set, a protrusion level of the adjustable mandibular displacement device can be dynamically and automatically controlled during the test period according to any of the methods discussed herein. For example, a protrusion level of the adjustable mandibular displacement device during the test period can be controlled by increasing protrusion level or decreasing protrusion level of the adjustable mandibular displacement device. The protrusion level can be adjusted to reduce or eliminate occurrence of respiratory events to an acceptable level, for example. Alternatively or additionally, a protrusion level of the adjustable mandibular displacement device during the test period can be controlled by adjusting the protrusion level of the adjustable mandibular displacement device based on at least one of frequency or severity of the one or more respiratory events. At least one of a magnitude or rate of adjustment can optionally be related to at least one of frequency or severity of the one or more respiratory events. For example, a greater magnitude and/or rate of adjustment of the protrusion level of the adjustable mandibular displacement device can correspond to a more frequent or severe respiratory event, and a lesser magnitude and/or rate of adjustment of the protrusion level of the adjustable mandibular displacement device can correspond to a less frequent or severe respiratory event. Optionally, a protrusion level of the adjustable mandibular displacement device during the test period can be controlled in response to not detecting a respiratory event during a fixed period of time in order to induce a respiratory event or to induce a change in respiratory airflow. Alternatively or additionally, a protrusion level of the adjustable mandibular displacement device can be controlled during the test period to optimize respiratory airflow.

Figure 5B:
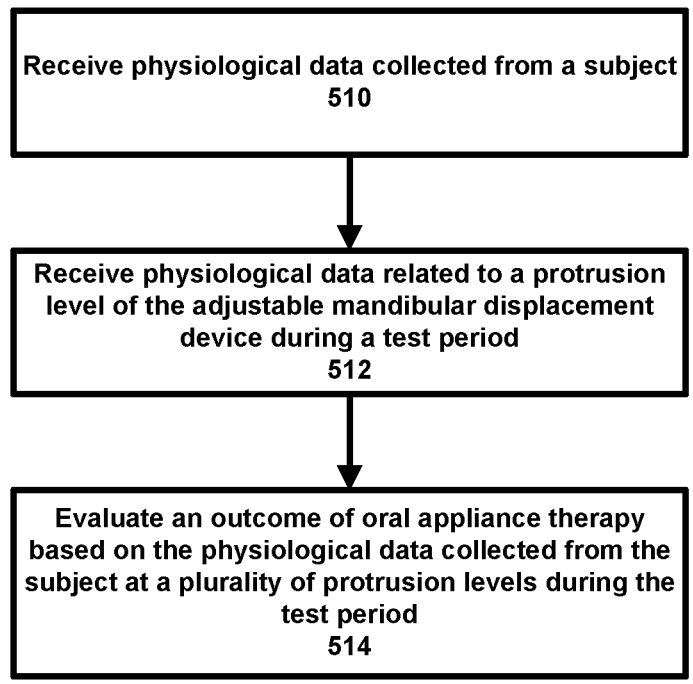
FIG. 5B is a flow diagram illustrating example operations for performing a titration for oral appliance therapy using data collected at a plurality of protrusion levels.

Referring now to FIG. 5B, a flow diagram illustrating example operations 500B for performing a titration for oral appliance therapy using data collected at a plurality of protrusion levels of an adjustable mandibular displacement device. Similarly to above, by evaluating an outcome of oral appliance therapy using data collected at plurality of protrusion levels, the overall response at various protrusion levels during a test period is examined in order to evaluate therapeutic outcome. For example, as discussed below, respiratory events are detected, and in some cases even evoked, and classified. Then, the protrusion level of the titration device is dynamically controlled in response to the respiratory events. The protrusion level can be controlled using a graded dynamic adjustment (e.g., magnitude and rate) according to the classified respiratory events. Therapeutic outcome can then be evaluated based on the overall data set, which includes, but is not limited to, the physiological response of the subject and information regarding the dynamic response of the titration device (e.g., how fast and how far the titration device moves during the test period).

For example, at 510, physiological data (e.g., the physiological information discussed herein) can be received from a subject. Additionally, at 512, data related to a protrusion level of the adjustable mandibular displacement device during the test period can be received. Then, at 514, an outcome of oral appliance therapy can be evaluated based on the physiological data collected from the subject at the plurality of protrusion levels of the adjustable mandibular displacement device during the test period. In the evaluation, the physiological data from the plurality of protrusion levels can be combined (for example, if needed to increase the amount of data to a minimum amount of time, for example greater than 1 hour).

Titrating in a Non-Clinical Setting

Figure 7:
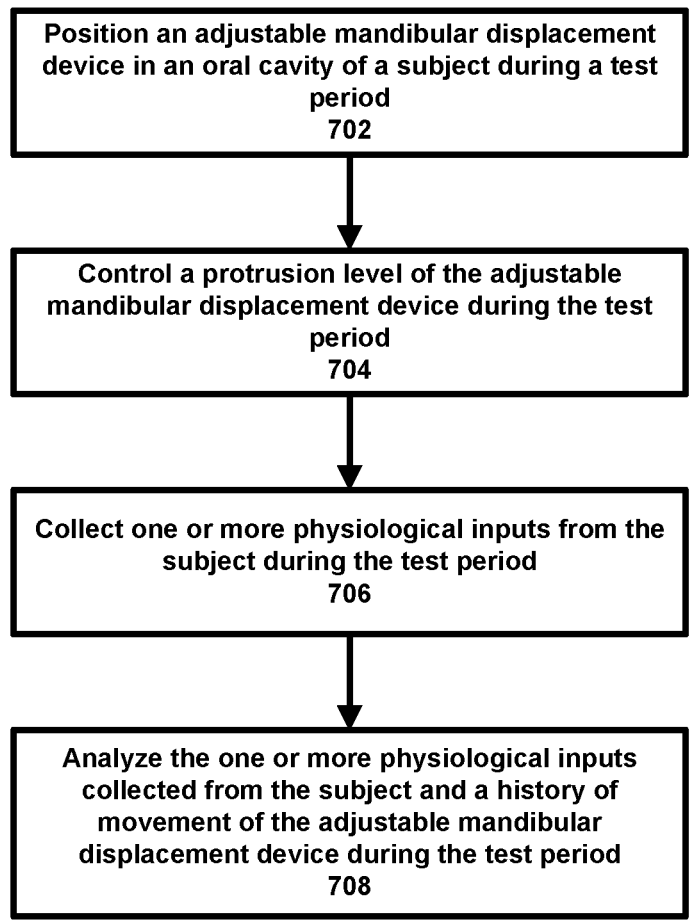
FIG. 7 is a flow diagram illustrating example operations for performing a titration for oral appliance therapy in a non-clinical setting.

Referring now to FIG. 7, a flow diagram illustrating example operations 700 for performing a titration for oral appliance therapy in a non-clinical setting is shown. As discussed herein, a titration in the non-clinical setting can be performed with limited information as compared to traditional sleep testing. In particular, it is possible to perform the titration (e.g., evaluate therapeutic outcome, predict effective protrusion level, etc.) without information collected during a traditional polysomnographic study, for example. The non-clinical setting can be a sleep session occurring outside of a sleep clinic. For example, the non-clinical setting can be a sleep session occurring in the subject's home. Alternatively or additionally, the non-clinical setting can be a sleep session occurring without a polysomnographic technician monitoring the subject and/or without conducting a polysomnographic study. Alternatively or additionally, the non-clinical setting can be a sleep session occurring with a pharmaceutical sleep aid to induce sleep in an office or outpatient setting, including a surgical arena. Optionally, the favorable candidate can be identified regardless of a sleep stage during the test period, a body position during the test period or a worst case scenario (e.g., a period of REM sleep in a supine position).

At 702, an adjustable mandibular displacement device can be positioned in an oral cavity of a subject during a test period. Optionally, as described herein, the conditions of the test period can be influenced by patient inputs (e.g., diagnostic information concerning the subject) determined in a different type of test, or obtained directly from the patient. Optionally, the test period can be set according to conditions determined from variables derived from the analysis of a previous test period. At 704, a protrusion level of the adjustable mandibular displacement device can be controlled during the test period. The protrusion level can be controlled by moving the adjustable mandibular displacement device between at least two protrusion levels, for example. The methods for controlling the adjustable mandibular displacement device can include any of the methods of adjustment discussed herein including, but not limited to, increasing/decreasing protrusion level to reduce/eliminate respiratory events, controlling a protrusion level based on an amount of elapsed time (e.g., holding the protrusion level constant for a fixed period), controlling magnitude or rate of adjustment based on frequency and severity of respiratory events, optimizing airflow, etc. At 706, one or more physiological inputs from the subject during the test period can be collected. In addition, at 708, the one or more physiological inputs collected from the subject and a history of movement of the adjustable mandibular displacement device during the test period can be analyzed. As discussed above, a determination as to whether the subject is a favorable candidate for oral appliance therapy and/or an effective protrusion level of the adjustable mandibular displacement device can be determined by analyzing the one or more physiological inputs collected from the subject and a history of movement of the adjustable mandibular displacement device during the test period. Optionally or additionally, the test analysis can include patient inputs determined by a different type of test, or obtained directly from the patient. Optionally or additionally, the analysis can be influenced by variables obtained and measured during the test or by a different test within the test plan. Optionally or additionally, the analysis can be used to influence the test plan.

In the non-clinical setting, the monitored physiological information can include respiratory airflow and oxygen saturation. Optionally, in the non-clinical setting, the monitored physiological information can only include respiratory airflow and oxygen saturation. Accordingly, the physiological inputs can include respiratory airflow and oxygen saturation and exclude other information collected during a polysomnographic study, for example. Respiratory airflow and oxygen saturation can be received from the subject during the test period, and one or more respiratory events can be detected during the test period using the received respiratory airflow and oxygen saturation. Respiratory event detection is discussed in detail above. For example, a respiratory event can be measured and defined according to predetermined criteria.

In the non-clinical setting, predicting whether the subject is a favorable candidate for oral appliance therapy can further include determining a frequency of respiratory events at or above each protrusion level during the test period. For example, the Residual RDI discussed above can be calculated using Eqn. (1). Alternatively or additionally, predicting whether the subject is a favorable candidate for oral appliance therapy can further include determining a percentage of time at or below each protrusion level during the test period. The percentage of time at or below each protrusion level can be calculated using Eqn. (2), for example. As discussed above, the subject can be a favorable candidate when the frequency of respiratory events is less than a predefined value or the percentage of time is greater than a predefined percentage of the test period. Optionally, the subject can be a favorable candidate when the frequency of respiratory events is less than the predefined value and the percentage of time is greater than the predefined percentage. Additionally, as discussed above, an effective protrusion level for oral appliance therapy can be a smallest protrusion level where the frequency of respiratory events is less than the predefined value and the percentage of time is greater than or equal to the predefined percentage.

Automatic Control of a Titration Device During a Titration

Figure 8:
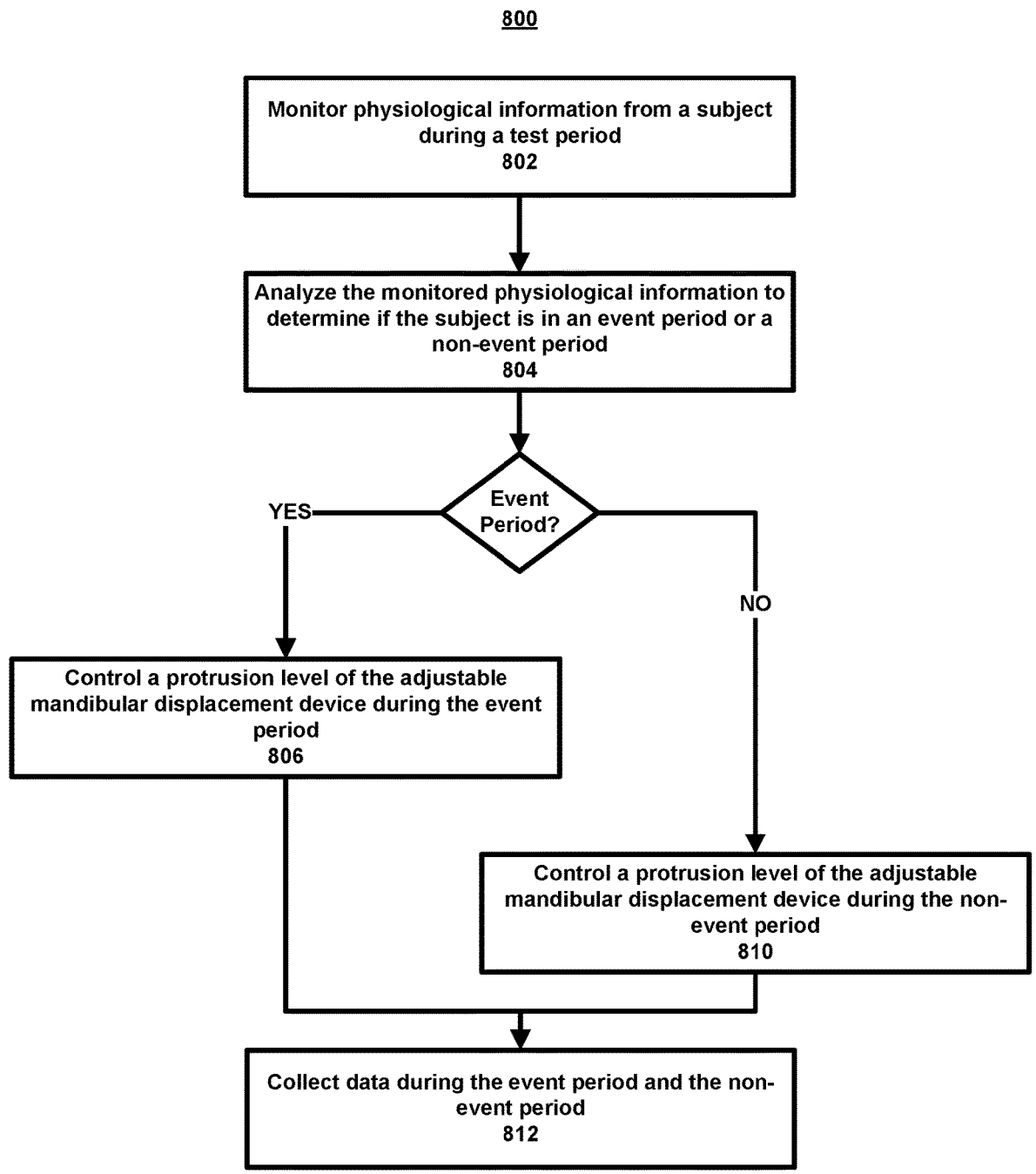
FIG. 8 is a flow diagram illustrating example operations for automatically controlling an adjustable mandibular displacement device while performing a titration for oral appliance therapy.

Referring now to FIG. 8, a flow diagram illustrating example operations 800 for automatically controlling an adjustable mandibular displacement device while titrating for oral appliance therapy is shown. Automatically controlling the adjustable mandibular displacement device can include a plurality of modes (e.g., an event mode and a non-event mode), and adaptive control algorithms can differ in each of the plurality of modes. In the event mode, an object of the adaptive control algorithm can be to adjust the titration device in response to respiratory events. In the non-event mode, an object of the adaptive control algorithm can be to induce respiratory events or a change in respiratory airflow and/or optimize respiratory airflow or to monitor and optimize other physiological inputs such as snoring.

For example, at 802, physiological information from a subject can be monitored during a test period. The test period can include at least one event period and at least one non-event period. At 804, the monitored physiological information can be analyzed to determine if the subject is in the at least one event period or the at least one non-event period. At 806, a protrusion level of the adjustable mandibular displacement device can be controlled during the at least one event period. At 808, a protrusion level of the adjustable mandibular displacement device can be controlled during the at least one non-event period. As discussed above, adaptive control algorithms are different for the event period and the non-event period. At 810, data can be collected during the at least one event period and the at least one non-event period.

An event period includes a portion of the test period where a frequency of the one or more respiratory events is greater than a predetermined threshold. Additionally, a non-event period includes a portion of the test period wherein a frequency of the one or more respiratory events is less than a predetermined threshold. For example, the predetermined threshold can be selected with the objectives discussed above in mind. In the event mode, the object can be to respond to respiratory events. When adjusting protrusion level in response to respiratory events, protrusion level can be increased to a point at which respiratory events are reduced or eliminated to an acceptable level (e.g., the frequency of respiratory event occurrence decreases). After respiratory events are reduced or eliminated below an acceptable level, and fewer respiratory events are occurring such that the protrusion level is not being adjusted as frequently in response to respiratory events, the adjustable mandibular displacement device can be controlled to induce respiratory events or a change in respiratory airflow or to optimize airflow, for example.

Optionally, collecting data can include collecting data regarding a history of movement of the adjustable mandibular displacement device during the at least one event period and the at least one non-event period. Alternatively or additionally, analyzing the monitored physiological information can include detecting one or more respiratory events. Respiratory event detection is discussed in detail above.

Additionally, during the event period, controlling a protrusion level of the adjustable mandibular displacement device can include at least one of increasing the protrusion level or decreasing the protrusion level of the adjustable mandibular displacement device. Optionally, controlling a protrusion level of the adjustable mandibular displacement device during the at least one event period can include adjusting the protrusion level of the adjustable mandibular displacement device based on at least one of frequency or severity of the one or more respiratory events. As discussed above, at least one of a magnitude and rate of adjustment can be related to at least one of frequency or severity of the one or more respiratory events.

Alternatively or additionally, during the non-event period, controlling the protrusion level of the adjustable mandibular displacement device can include adjusting the protrusion level to induce a change in respiratory airflow. For example, the protrusion level can be decreased to induce a respiratory event. In addition, the protrusion level of the adjustable mandibular displacement device can be controlled to optimize respiratory airflow. Methods for optimizing respiratory airflow are discussed in detail above.

Alternatively or additionally, during the non-event period, controlling the protrusion level of the adjustable mandibular displacement device can include adjusting the protrusion level to monitor changes in snoring. For example, the protrusion level can be adjusted to test or optimize the protrusive level such that amount, magnitude or degree of snoring is minimized while maintaining events below a predetermined threshold.

Titrating Based on Attractor Behavior

As discussed herein, attractor behavior occurs at a protrusion level where a small increase in the protrusion level results in an insignificant change in respiratory airflow (e.g., peak ventilation) and a small decrease in the protrusion level results in a signification change in respiratory airflow (e.g., peak ventilation). Attractor behavior can be discovered while controlling the protrusion level to optimize respiratory airflow (e.g., during the search for $P_{opt}/P_{crit}$), which is discussed above. Observance of attractor behavior can occur after the respiratory events have been eliminated, but it is not required. For instance the attractor behavior can be observed at a protrusive level where the respiratory event frequency is not below a predetermined threshold at the time of detection. It should be understood that the mechanics of the pharynx provide this particularly sensitive spot. Additionally, while a more gradual form of attractor behavior is observed during CPAP therapy, attractor behavior during OA therapy is more severe and abrupt. Accordingly, the protrusion level at which attractor behavior occurs can be the effective protrusion level for oral appliance therapy.

Figure 9:
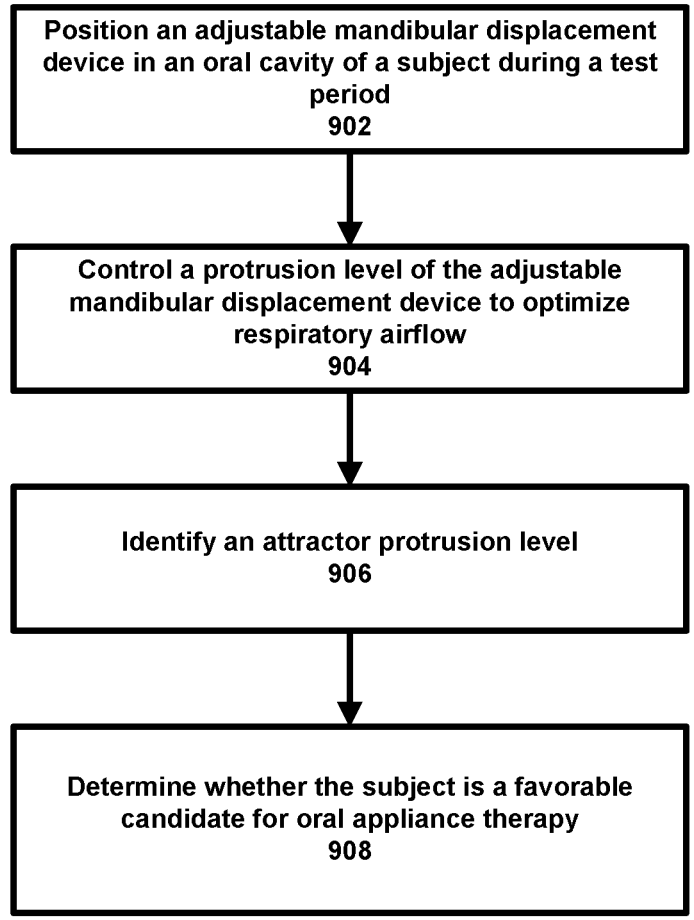
FIG. 9 is a flow diagram illustrating example operations for identifying a candidate for oral appliance therapy based on attractor behavior.

Referring now to FIG. 9, a flow diagram illustrating example operations 900 for identifying a candidate for oral appliance therapy based on attractor behavior is shown. At 902, an adjustable mandibular displacement device can be positioned in an oral cavity of a subject during a test period. At 904, the protrusion level of the adjustable mandibular displacement device can be controlled to optimize respiratory airflow. Methods for optimizing airflow are discussed in detail above. For example, the protrusion level can be controlled in a search for $P_{opt}/P_{crit}$. At 906, an attractor protrusion level can be identified. The attractor protrusion level is a protrusion level where a small increase in the protrusion level results in an insignificant change in respiratory airflow and a small decrease in the protrusion level results in a signification change in respiratory airflow. When identifying attractor behavior, a perturbation (e.g., a small change in protrusion level) is made, and the effect on respiratory airflow is immediately examined (e.g., within a predetermined time from the change in protrusion level) to observe the mechanical effect on the airway. For instance within 5 breaths, or approximately 20 seconds. After this time, chemo reflexes take over and attractor behavior fades. At 908, in response to identifying an attractor protrusion level, a determination can be made that the subject is a favorable candidate for oral appliance therapy. Optionally, an effective protrusion level for oral appliance therapy can be approximately the attractor protrusion level. Additionally, in response to not identifying an attractor protrusion level, a titration can be performed based on a history of movement of the adjustable mandibular displacement device and one or more respiratory events during the test period.

Optionally and additionally, attractor behavior measured in the test can be used for other purposes as described herein. For example, attractor behavior can be used as a variable determined from the analysis of data collected during a test period and can optionally be used to affect the test plan and/or to evaluate the outcome of oral appliance therapy.

Multi-Test-Period Protocol and Analysis

As discussed herein, a multi-test-period protocol includes performing at least two titrations during separate and distinct test periods (e.g., a first test period, a second test period, a third test period, or a fourth test period, etc., for example). It should be understood that four test periods are provided as an example and that this disclosure contemplates a multi-test-period plan including more or less than four test periods. Optionally, the second, third, or fourth, etc. test period can be subsequent in time to the first test period. For example, the first test period can be sleep during a first session, and the second, third, or fourth, etc. test period can be sleep during second, third, or fourth etc. sessions. As described herein, a sleep session can be defined by a measured duration of sleep (e.g., about 4 hours), the receipt of a sufficient amount and/or quality of data (e.g., exploration of the full range of motion of the patient's mandible), a voluntary action of the patient (e.g. the patient wakes up and concludes the study), or combinations thereof. Alternatively or additionally, each subsequent session (e.g., the second, third, or fourth etc. session) is later in time. Alternatively, the first, second, third, or fourth, etc. test periods are not successive in time. Alternatively or additionally, each respective test period can be sleep during a different sleep session. The different sleep sessions can be on the same night. Alternatively, the different sleep sessions can be on different nights Optionally, the first test period can be sleep during a first night, and the second, third, or fourth etc. test period can be sleep during a second, third, or fourth, etc. night, or some combination of full nights and portions of nights. Optionally, the first test period can be sleep during a first portion of the night, and the second test period can be sleep during a second portion of the same night. The test protocol in the first period can be the same or different than the test protocol in the second, third, or fourth, etc. test period. The test protocols (e.g., a dynamic control protocol, a static control protocol, or a refinement protocol as described below) used during each respective test period can be devised according to a multi-test-period plan. Alternatively or additionally, the combination of the multiple tests, and the variables analyzed within each, can be used to evaluate the outcome of oral appliance therapy. Alternatively or additionally, the first test period can include sleep in one of a supine or lateral position, and the second test period can include sleep in the other of the supine or lateral position. Optionally, the second test period can include sleep with a different therapeutic intervention than the first test period. For example, the therapeutic intervention during the first test period and the second test period can be at least one of an oral appliance, a different amount of occlusal separation or an oral appliance used in conjunction with CPAP.

As described above, the techniques described herein can optionally employ 1) a real-time analysis for controlling the adjustable mandibular displacement device and 2) a separate analysis for predicting an outcome for oral appliance therapy. Optionally, the separate analysis can be performed offline, or at the conclusion of the sleep session or sleep study. In other words, the adjustable mandibular displacement device can be controlled in real-time in response to the data being collected (e.g., physiological responses) during a test period. Optionally, adjustable mandibular displacement device control techniques can be selected to collect certain types of information. For example, the dynamic control protocol can be selected to collect data at multiple protrusion levels to identify an optimal protrusion level, while the static control protocol can be selected to confirm the predicted optimal protrusion level. Alternatively, two different control protocols can be selected to collect two different types of data set with different types of variables. It should be understood that different adjustable mandibular displacement device control techniques can be used during different test periods.

Additionally, the outcome of oral appliance therapy (e.g., the final analysis or final evaluation) can be predicted based on the data collected during one or more test periods. The collected data can include but is not limited to one or more of the variables associated with one or more test periods (e.g., as illustrated by FIG. 12). In other words, the collected data can include data collected during a plurality of different test periods, each of which optionally employs a different adjustable mandibular displacement device control technique, and the final analysis can be predicted based on the entire set of collected data. Optionally, this analysis can be performed offline after the conclusion of the one or more test periods. Additionally, as described herein, the final analysis can employ one or more techniques for predicting the outcome of oral appliance therapy.

Figure 10A:
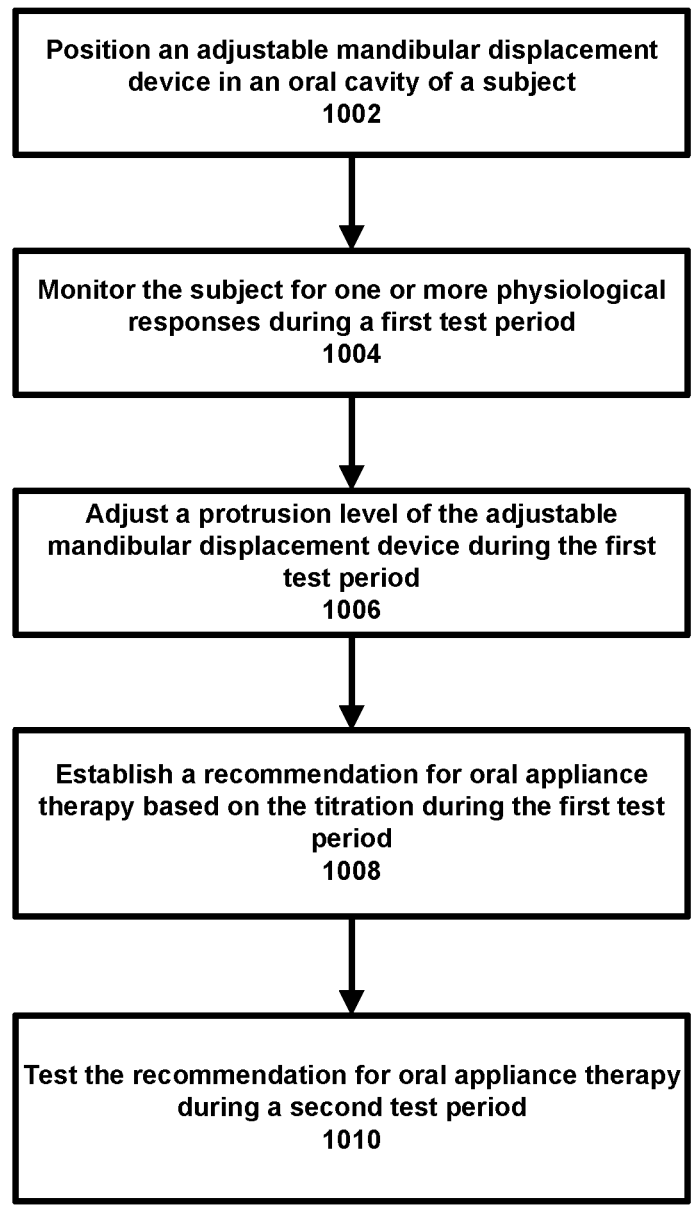
FIGS. 10A-10C are a flow diagrams illustrating example operations for performing a titration for oral appliance therapy using a multi-test-period protocol.

Referring now to FIG. 10A, a flow diagram illustrating example operations 1000A for performing a titration for oral appliance therapy using a multi-test-period protocol is shown. At 1002, an adjustable mandibular displacement device can be positioned in an oral cavity of a subject. At 1004, the subject can be monitored for one or more physiological responses during a first test period. Optionally, a physiological response can be a respiratory event, for example. Detecting respiratory events is discussed in detail above. For example, detecting a respiratory event includes defining and measuring physiological information from a subject against predetermined criteria. At 1006, a protrusion level of the adjustable mandibular displacement device can be adjusted during the first test period. Methods for controlling the adjustable mandibular displacement device are discussed above including, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. At 1008, a recommendation for oral appliance therapy can be established based on the titration of the protrusion level of the adjustable mandibular displacement device during the first test period. The recommendation can be whether the subject is a predicted success (e.g., a favorable candidate for oral appliance therapy), an effective protrusion level or a range of effective protrusion levels, etc. Then, at 1010, the recommendation for oral appliance therapy can be tested and/or refined during a second test period.

Additionally, testing the recommendation for oral appliance therapy can include monitoring the subject for one or more physiological responses during the second test period. The recommendation for oral appliance therapy can be confirmed, refined or rejected based on the one or more physiological responses during the second test period. For example, if the outcomes of the titration during the first and second test periods are consistent, the recommendation can be confirmed. However, if the outcomes of the titration during the first and second test periods are inconsistent, the recommendation can be rejected. If the recommendation is rejected, a third test period may be used to confirm the new recommendation or to provide or refine a target protrusive position if the recommendation was altered from predicted failure to predicted success. It should be understood that the outcomes can be whether the subject is a predicted success (e.g., a favorable candidate for oral appliance therapy), an effective protrusion level or a range of effective protrusion levels, etc.

In addition, establishing a recommendation for oral appliance therapy can include identifying a range of effective protrusion levels for oral appliance therapy. For example, the range of effective protrusion levels can be between x and y mm, for example. Optionally, testing the recommendation for oral appliance therapy can include adjusting the protrusion level of the adjustable mandibular displacement device within the range of effective protrusion levels during the second test period. In other words, during the second test period, the adjustable mandibular displacement device is adjusted within the range of effective protrusion levels (e.g., between x and y mm, for example). Optionally, an effective protrusion level for oral appliance therapy can be identified based on the adjustment of the protrusion level of the adjustable mandibular displacement device during the second test period. Accordingly, a rough estimate or range of effective protrusion levels is identified during the first test period, and the effective protrusion level is refined during the second test period.

Alternatively or additionally, establishing a recommendation for oral appliance therapy can include identifying an effective protrusion level for oral appliance therapy during the first test period. In addition, testing the recommendation for oral appliance therapy can include fixing the adjustable mandibular displacement device at the effective protrusion level during the second test period. When the adjustable mandibular displacement device is fixed, it is not or minimally adjusted during the second test period. Instead, the subject is monitored for physiological responses during the second test period at the recommended effective protrusion level for confirmatory purposes.

Optionally, a measure of predicted therapeutic outcome for oral appliance therapy can be provided. For example, the measure of predicted therapeutic outcome can be at least one of an Apnea-Hypopnea Index (AHI), an Oxygen Desaturation Index (ODI), a Mean $O_2$ Saturation, and Inspiratory Flow Limitation Index or a Respiratory Disturbance Index (RDI).

Figure 10B:
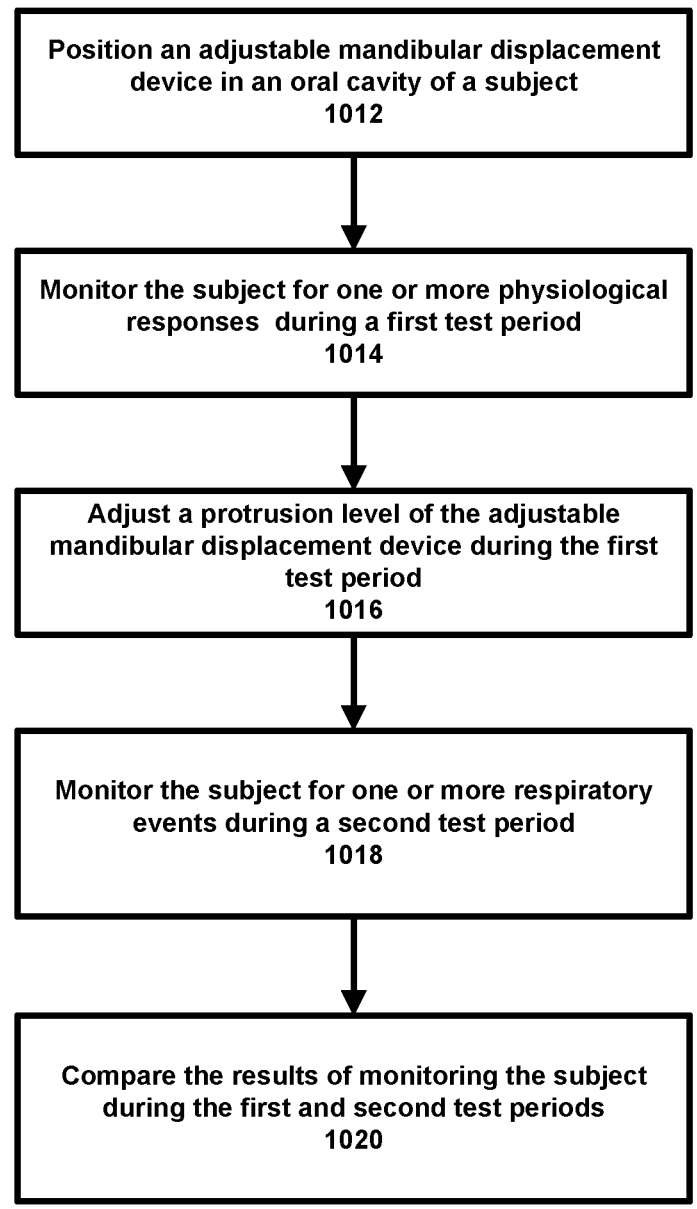

Referring now to FIG. 10B, a flow diagram illustrating example operations 1000B for titrating for oral appliance therapy using a multi-test-period protocol is shown. At 1012, an adjustable mandibular displacement device can be positioned in an oral cavity of a subject. At 1014, the subject can be monitored for one or more physiological responses during a first test period. Optionally, a physiological response can be a respiratory event, for example. Detecting respiratory events is discussed in detail above. For example, detecting a respiratory event includes defining and measuring physiological information from a subject against predetermined criteria. At 1016, a protrusion level of the adjustable mandibular displacement device can be adjusted during the first test period. Methods for controlling the adjustable mandibular displacement device are discussed above including, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. At 1018, the subject can be monitored for one or more physiological responses during a second test period. Then, at 1020, the results of monitoring the subject for one or more physiological responses during the first test period can be compared with results of monitoring the subject for one or more physiological responses during the second test period.

Optionally, the protrusion level of the adjustable mandibular displacement device can be adjusted during the second test period. Methods for controlling the adjustable mandibular displacement device are discussed above including, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. Alternatively or additionally, a recommendation for oral appliance therapy can be established based on the adjustment of the protrusion level of the adjustable mandibular displacement device during the first test period, and the recommendation for oral appliance therapy can be confirmed, refined or rejected based on the based on the adjustment of the protrusion level of the adjustable mandibular displacement device during the second test period.

Figure 10C:
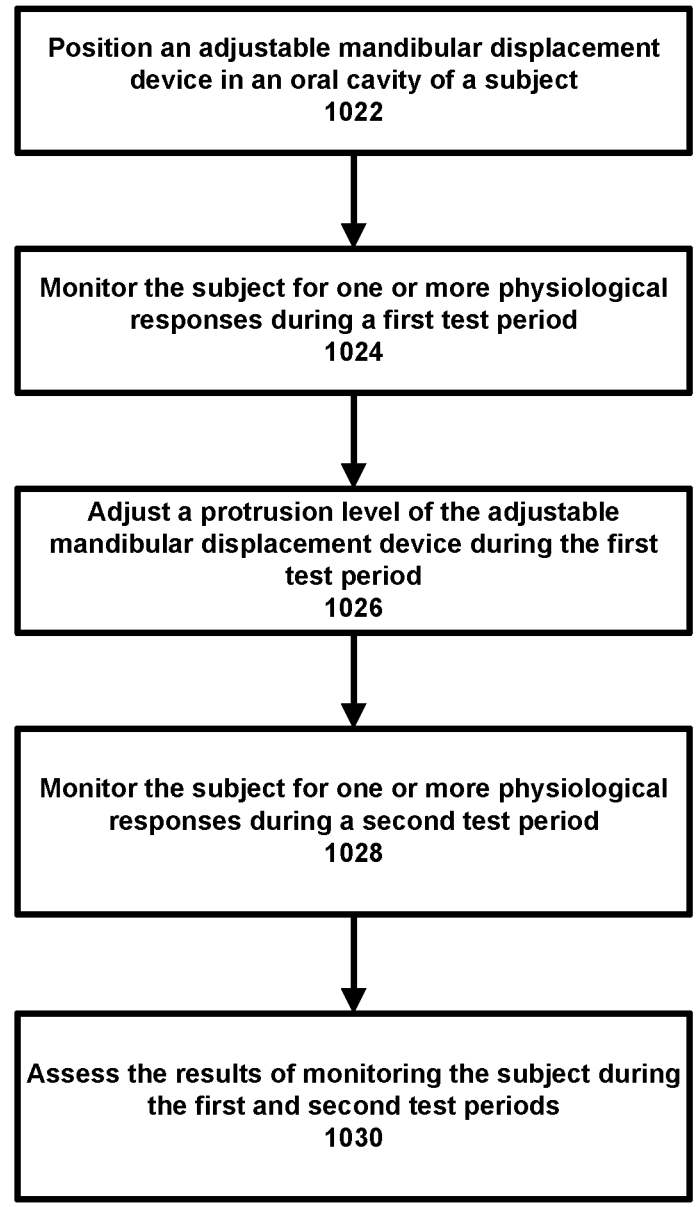

Referring now to FIG. 10C, a flow diagram illustrating example operations 1000C for a multi-test-period protocol for titrating for oral appliance therapy is shown. At 1022, an adjustable mandibular displacement device can be positioned in an oral cavity of a subject. At 1024, the subject can be monitored for one or more physiological responses during a first test period. Optionally, a physiological response can be a respiratory event, for example. Detecting respiratory events is discussed in detail above. For example, detecting a respiratory event includes defining and measuring physiological information from a subject against predetermined criteria. At 1026, a protrusion level of the adjustable mandibular displacement device can be adjusted during the first test period. The protrusion level can be adjusted using any of the adjustable mandibular displacement device control techniques described herein. For example, methods for controlling the adjustable mandibular displacement device are discussed above including, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. At 1028, the subject can be monitored for one or more physiological responses during a second test period. Optionally, as described herein, the adjustable mandibular displacement device control techniques employed during the second test period can differ from those employed during the first test period. For example, the duration of time prior to allowing an adjustment, the use of respiratory airflow adjustment, and/or any other parameter can be different for the adjustable mandibular displacement device control techniques employed during the different test periods. For example, in some implementations, the second test period can be designed to collect more information at a certain protrusion level as compared to the first test period. Optionally, the setting of the certain protrusion level of interest during the second test period (e.g., parameters associated with the second test period) can be based on an analysis of the first test period. Then, at 1020, results of monitoring the subject for one or more physiological responses during the first test period and results of monitoring the subject for one or more physiological responses during the second test period can be assessed.

In some implementations, assessing results of monitoring (e.g., the final analysis or final evaluation) the subject for one or more physiological responses during the first test period and results of monitoring the subject for one or more physiological responses during the second test period can include averaging or combining the results of monitoring the subject for one or more physiological responses during the first test period and the results of monitoring the subject for one or more physiological responses during the second test period. In other implementations, assessing results of monitoring (e.g., the final analysis or final evaluation) can be based on the results of monitoring during both the first and second test periods. Although two test periods are provided as an example, this disclosure contemplates basing the assessment on any number of test periods. This can include analyzing one or more of the variables associated with the first and second test periods. Optionally, the final analysis can be performed offline after conclusion of both the first and second test periods. Optionally, the final analysis can employ a machine learning technique such as a neural network, support vector machine, decision tree, random forest, etc. As described herein, the final analysis can use one or more trained machine learning modules. The method can further include establishing a recommendation for oral appliance therapy based on the assessed results.

Optionally and additionally, a plurality of test periods can be devised according to a test plan. The test plan can optionally be created before (e.g., earlier in time) performing test protocols during one or more of the test periods. Optionally, the test plan is created before performing a protocol during any test period. Optionally, the test plan can be modified or altered while performing test protocols during one or more of the test periods, for example, in response to one or more variables analyzed during a test period. Alternatively or additionally, the test plan can consider the desired outcome of the recommendation for oral appliance therapy. As described herein, the test plan can include the selection of adjustable mandibular displacement control techniques (and optionally one or more parameters associated therewith) based on the desired outcome. Different adjustable mandibular displacement control techniques can be employed during different test period as described herein, for example, to achieve different objectives. Alternatively or additionally, the test plan can include the selection of oral appliance therapy outcome prediction techniques based on the desired outcome. Different oral appliance therapy outcome prediction techniques can be employed, for example, to achieve different objectives. For example, in some implementations, a decision tree can be employed to predict the outcome of oral appliance therapy, while in other implementations, a random forest can be employed to predict the outcome of oral appliance therapy. Optionally, selecting decision tree or random forest analysis can depend on the desired outcome. Optionally, the same type of prediction technique (e.g., random forest) can be used to predict for different desired outcomes but the design of the prediction techniques (e.g., the number of decision trees, weighting, etc.) can be different for the different desired outcomes. As used herein, the desired outcome can be the desired level of accuracy for the recommendation, such as the accuracy of the prediction of whether the subject is a favorable candidate for oral appliance therapy or not, or the accuracy of the predicted effective protrusion level for oral appliance therapy (also referred to herein as the "target protrusive position"). For example, repeating and averaging the results of multiple test periods, or adding an additional test period that confirms or refines the outcomes as described above will result in an increased accuracy, or using the results from two different types of test periods (e.g. one under dynamic and one under static control). Additionally, the desired outcome can include achieving a desired measure of predicted therapeutic outcome for oral appliance therapy (e.g., AHI<10) or achieving a desired measure of predicted therapeutic outcome for oral appliance therapy and a desired percentage reduction (e.g., AHI<10 and a 50% reduction from baseline). Optionally, the desired outcome can include achieving a desired measure of predicted therapeutic outcome for oral appliance therapy with a specific type of event (e.g., AHI or ODI). Further, the desired outcome can include a desired level of optimization of the protrusion level for oral appliance therapy. For example, it may be desired to minimize the protrusion level for oral appliance therapy, or alternatively, it may be acceptable to select any effective protrusion level for oral appliance therapy. Adding an additional test period may minimize the target protrusive position, as described with reference to FIG. 13; however, depending on the test plan, adding a test period may also increase the target protrusive position in order to increase the accuracy. The test plan can optionally consider the maximum number of desired test sessions that can be tolerated by the subject (also referred to herein as the "patient"), afforded by the user, and/or constrained by the features of the mandibular displacement device (e.g., the battery life or other limited-life disposables). Alternatively or additionally, the test plan may optionally consider the anatomy of the subject who may or may not require a minimally protrusive position in order to tolerate oral appliance therapy (e.g., temporomandibular joint (TMJ) concerns).

Optionally, the test plan and/or the analysis of the test periods can consider patient inputs (also referred to herein as "diagnostic information concerning the subject"). In other words, the diagnostic information concerning the subject can optionally influence the test plan, including the number of test periods, protocols to be performed, and/or parameter(s) of the protocols. The patient inputs can optionally be any information about the subject, including but not limited to a baseline measure of respiratory events experienced by the subject, a distribution of respiratory events (e.g., including clustering of respiratory events), a level of oxygen desaturation, the subject's body position during a diagnostic sleep study, a sleep stage during a diagnostic sleep study, the subject's physical characteristics, the subject's medical history, or the subject's symptoms. The patient inputs can optionally be determined by a different test (e.g., a diagnostic test) performed with the mandibular displacement device used for a titration but without positioning the oral appliance in the subject's mouth, as described below. For example, the diagnostic test can be used to determine a subject's frequency of respiratory events without oral appliance therapy or some other diagnostic variable. Alternatively or additionally, the patient inputs can optionally be derived directly from the patient (e.g., through a questionnaire eliciting use of the subject's physical characteristics, medication, medical history, presence of certain symptoms, history of hypertension, history of pulmonary dysfunction, etc.) and/or derived through direct measurement of the subject (e.g., height, weight, neck circumference, body mass index (BMI), etc.). Optionally, the patient inputs can include test period-to-test period (e.g., night-to-night) variability of any patient input measured/analyzed over multiple test periods. Alternatively or additionally, the multi-test-period plan can include an additional test period to increase the accuracy for a certain subjects (e.g., subjects with mild sleep apnea where the accuracy may be hampered by detecting a smaller change, or subjects with severe sleep apnea where the desired accuracy may be increased due to the health implications).

The multi-test-period plan can optionally be altered by the analysis of one or more test periods in the multi-test-period plan. The analysis of a test period can include the collection, measurement and/or analysis of data from the test period, including but not limited to, the physiological information from the subject and/or the history of the protrusion level of the mandibular displacement device. The analysis of the test period can include the determination or identification of at least one variable associated with the data collected during the test period. For example, the variable can include one or more of a predicted outcome of oral appliance therapy, a predicted effective protrusion level for oral appliance therapy, or a predicted optimal protrusion level for oral appliance therapy. In other words, the variable can be the predicted outcome of oral appliance therapy determined during a titration performed during a test period. Alternatively or additionally, the variable can include one or more of a measure of respiratory events such as a count or frequency of respiratory events (e.g., an apnea hypopnea index (AHI), such as $$\frac{\text{\# of apneas and hypopneas}}{\text{period of time}}).$$

Alternatively or additionally, the variable can include other measures associated with the data collected during the test period including but not limited to the variables illustrated in FIG. 12. Optionally, the multi-test-period plan can be altered by a discrepancy in the outcome between two test periods (e.g., a first and second test period), for example, by adding an additional test period (e.g., a third, fourth, etc. test period). For example, as described above, the multi-test-period plan include, or be altered to include, a confirmatory and/or refinement test period.

Alternatively or additionally, one or more parameters for a test period (e.g., for a protocol performed during the test period) can optionally be set in dependence on the identified variable (or variables) associated with other test periods. The other test periods can optionally be performed prior to or before the test period for which the parameter is set. For example, a parameter for a protocol performed during a second, third, fourth, etc. test period can be set in dependence upon the variable (or variables) identified during the first test period, which is optionally performed earlier in time. The parameter can optionally be a beginning protrusion level, a protrusion level adjustment rate, a protrusion level range, a criterion for adjusting the protrusion level (e.g., adjust protrusion level when AHI>10 or any other criterion), a width and/or position of a correlation window (e.g., lag time for detecting respiratory events by matching airflow and oxygen desaturation events as described above), a type of protocol, criteria defining a respiratory event (e.g., the predetermined criteria against which respiratory events are defined and measured as describe above), a sleep study qualifying condition, or a length of time before adjusting protrusion level.

For example, if the outcome from a first test period (e.g., in which a titration protocol is performed during which the subject's mandibular displacement is controlled between a plurality of protrusion levels) predicted the subject to be a candidate for oral appliance therapy, then the parameters for a second test period (e.g., in which a titration protocol is performed during which the subject's mandibular displacement is controlled between a plurality of protrusion levels) may be set to start the movement of the mandibular displacement device at an established target protrusive position from the first test period. Alternatively, if the outcome from a first test period is predicted the subject to not be a candidate for oral appliance therapy, then the second test period may start the mandibular displacement device at a preselected target protrusive position. The preselected target protrusive position can optionally be selected to be a level near the maximum protrusion level to ensure that level of protrusion most likely to demonstrate successful treatment is fully tested. The preselected target protrusion can optionally be 90% of maximum protrusion for the subject, for example. This disclosure contemplates that the preselected protrusion can be more or less than 90% of maximum protrusion. Alternatively, and in particular if the multi-period-test plan requested a minimal protrusive position, the preselected protrusion may be less than 90% of maximum protrusion. Alternatively or additionally, the decision to perform the second test period can be based on the analysis of the first test period. In other words, in some cases, the second test period may not be performed depending on the results of the first test period. Alternatively and additionally, if a third test period is performed according to the multi-period-test plan, the third test period may start at the previously preselected protrusion (e.g., 90% of maximum protrusion) or at a value less than a previously selected protrusion (e.g., <90% of maximum protrusion or 70% of maximum protrusion). Alternatively or additionally, the parameters of the subsequent test period can also be optionally set by the analysis of certain variables of a previous test period in terms of the study qualification conditions such as the length of time needed, the levels of protrusion required, or the movement of the adjustable mandibular displacement device, for example. Alternatively or additionally, the parameters of the subsequent test period can also be optionally set by the analysis of certain variables of a previous test period in terms of variables such as the previously described lag time. For example, as described above, a fixed lag time can be used during a first test period, and then a customized time lag can be used in a second test period.

Figure 10D:
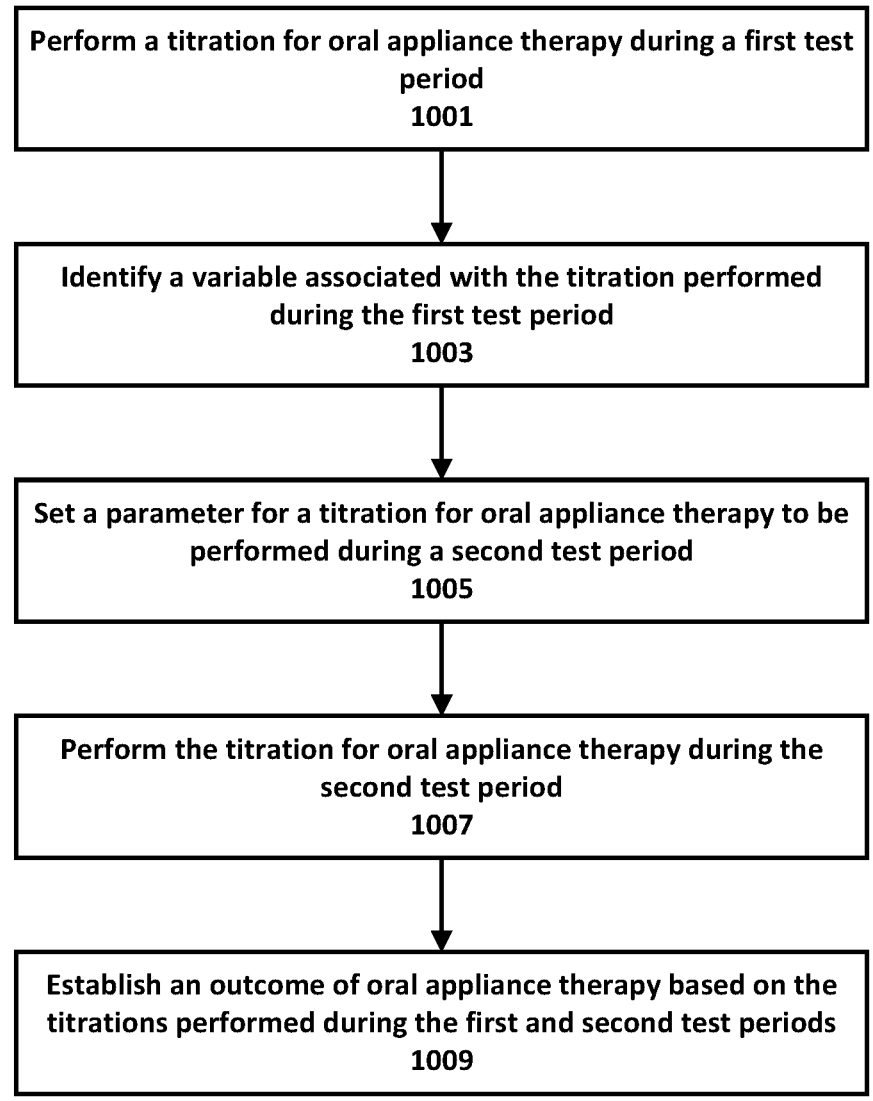
FIG. 10D is a flow diagram illustrating example operations for setting test parameters for a multi-test-period titration for oral appliance therapy.

Referring now to FIG. 10D, a flow diagram illustrating example operations 1000D for setting parameters for a multi-test-period titration for oral appliance therapy is described. Optionally, as described above, the multi-test-period titration can be performed based on a test plan, which has been developed previously. At 1001, a titration for oral appliance therapy is performed during a first test period. At 1003, a variable associated with the titration performed during the first test period is identified. For example, in one implementation described with regard to FIG. 13, the variable is the predicted outcome of oral appliance therapy (e.g., predicted success or failure of oral appliance therapy for the subject). At 1005, a parameter for a titration for oral appliance therapy to be performed during a second test period is set. As described herein, the parameter can be dependent on the variable associated with the titration performed during the first test period. For example, in one implementation described with regard to FIG. 13, the parameter is the beginning protrusion level for a subsequent titration, which depends on whether the titration performed in the previous test period predicts success or failure of oral appliance therapy for the subject. At 1007, the titration for oral appliance therapy is performed during the second test period. At 1009, an outcome of oral appliance therapy can be established based on the titrations performed during the first and second test periods.

Figure 13:
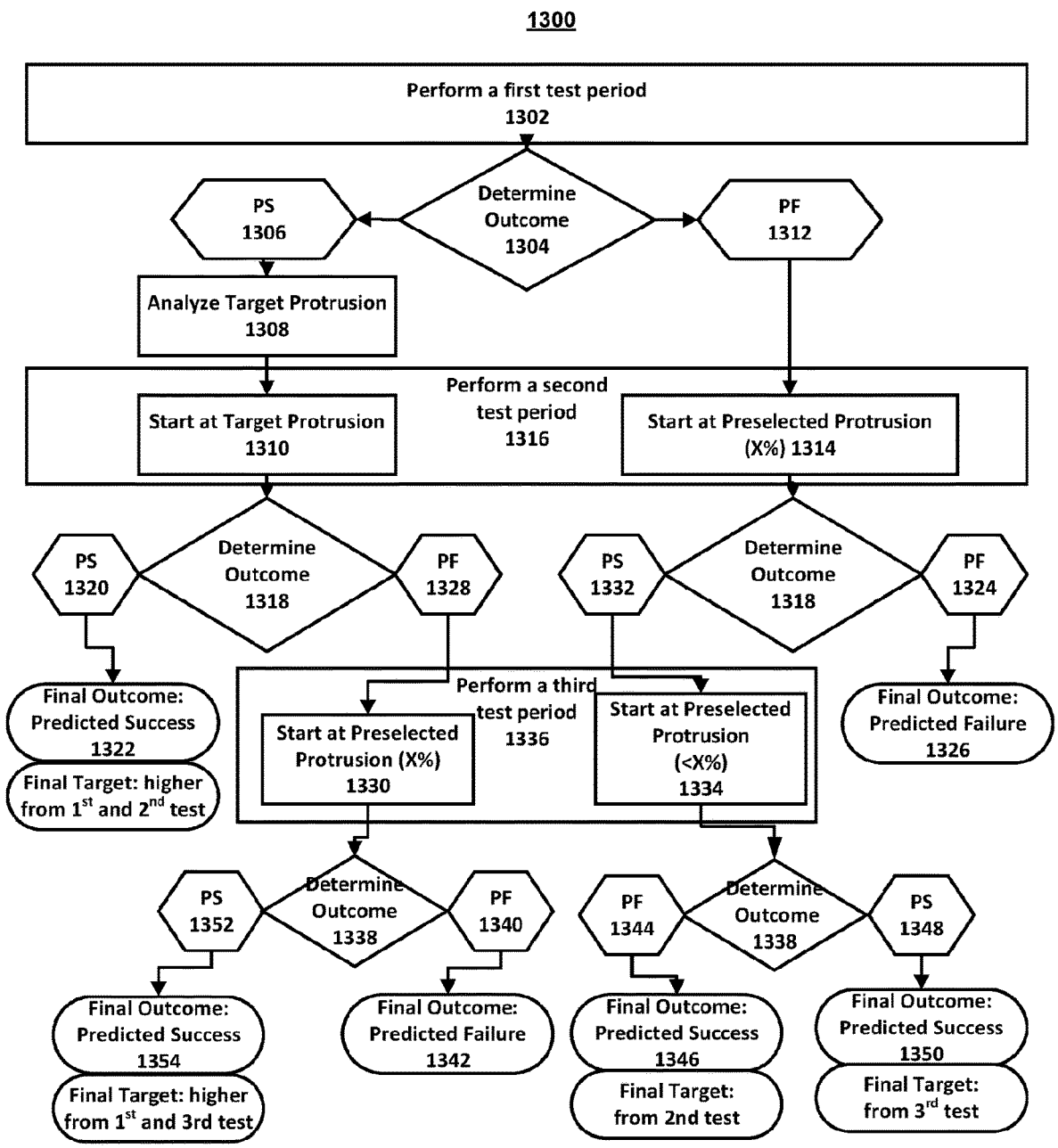
FIG. 13 is a flow diagram illustrating example operations for conducting a multi-test-period titration for oral appliance therapy.

Optionally, the outcome of the oral appliance therapy can be the outcome predicted by one of the test periods (e.g., the first, second, third, fourth, etc. test period). Alternatively or additionally, the outcome of the oral appliance therapy can be the predicted outcome determined by several test periods, for example several effective protrusion levels determined during different test periods, each being suggested based on different treatment criterion (e.g., achieving AHI<10, AHI<5, etc.). The outcome of oral appliance therapy can optionally be a prediction of success or failure of oral appliance therapy, a predicted effective protrusion level for oral appliance therapy, or a predicted optimal protrusion level for oral appliance therapy. For example, the outcome of oral appliance therapy can be the predicted effective protrusion level for oral appliance therapy determined during at least one of the test periods. The established outcome of oral appliance therapy is not required to be an outcome of the test period performed later or last in time. Additionally, the outcome of oral appliance therapy is not required to be an average, confirmation, or refinement of the outcomes established by more than one test period. Instead, the outcome of oral appliance therapy can be based on the results of two or more test periods (e.g., a combination analysis). In this way, the results of multiple test periods can be used to establish the outcome for oral appliance therapy. Optionally, as described herein, the outcome of the oral appliance therapy can be a final analysis which is based on the data collected during multiple test periods. This can include analyzing one or more of the variables associated with the different test periods (e.g., one or more of the variables illustrated by FIG. 12). Optionally, the final analysis can be performed offline after conclusion of the multiple test periods. Optionally, the final analysis can employ a machine learning technique such as a neural network, support vector machine, decision tree, random forest, etc. As described herein, the final analysis can use one or more trained machine learning modules. Alternatively or additionally, the type of final analysis can optionally be selected based on the desired outcome. Different analyses can be performed based on the desired outcome. For example, a first type of final analysis can be performed when the desired outcome is a certain measure of predicted therapeutic outcome for oral appliance therapy (e.g., AHI<10 or ODI<10), while a second type of final analysis can be performed when the desired outcome is a different measure of predicted therapeutic outcome for oral appliance therapy (e.g., AHI<10 and a 50% reduction from baseline). The types of final analyses can include methods for relating variables associated with data collected during the multiple test periods to outcome of oral appliance therapy including but not limited to machine learning techniques such as neural networks, support vector machines, decision trees, random forests, etc. Optionally, information learned during each of the test periods can influence the predicted outcome of oral appliance therapy. For example, as shown in FIG. 13, the outcome of oral appliance therapy is taken from: (i) a prediction of success (or failure) from the analysis of the last test period in time and (ii) a predicted effective protrusion level from the analysis of a test period performed earlier in time. In this example, the result of each test period makes up a portion of the final predicted outcome of oral appliance therapy. As another example, as shown in FIG. 14C, the outcome of oral appliance therapy is based on: (i) a maximum residual AHI from a first test period (performed earlier in time) and (ii) a frequency of events during a last hour of a second test period (performed later in time). In this example, information—an analyzed variable—from each of the test periods influences the final predicted outcome of oral appliance therapy. It should be understood that these are only examples of establishing an outcome of oral appliance therapy based on a combination of test periods. For example, the outcome of oral appliance therapy can be established based on any data collected, measured, and/or analyzed (e.g., a variable as described above) during multiple test periods. For example, data collected, measured, and/or analyzed during a subsequent test period can indicate that the outcome from one or more previously performed test periods is more reliable or more accurate. Alternatively, data collected, measured, and/or analyzed during a previous test period can indicate that the outcome from one or more subsequently performed test periods is more reliable or more accurate. For example, the data collected, measured, and/or analyzed during one of the first or second test period can reveal that the outcome of oral appliance therapy predicted by one of the test periods is more reliable or more accurate than the other test period. In other words, one or more of the variables identified during each test period can guide the protocols performed during subsequent test periods, as well as provide information as to the reliability of the predicted outcome. This disclosure contemplates that the variable(s) upon which the parameter(s) for the protocol performed during a subsequent test period are set can be the same or different than the variable(s) used to establish the outcome of oral appliance therapy. Thus, the more reliable and/or more accurate outcome can be chosen. Optionally, as described above, the outcome of the oral appliance therapy can be the outcome predicted by a combination of the test periods (e.g., averaging or refining).

Optionally, the operations can include receiving diagnostic information concerning the subject (e.g., the patient inputs described above). The diagnostic information can be used to establish the outcome of oral appliance therapy and/or to set the parameter for a test protocol. For example, the diagnostic information can be a measure of respiratory events experienced by the subject in the absence of oral appliance therapy (e.g., a baseline measure of respiratory events from a diagnostic study). Optionally, the diagnostic information can be measured in conjunction with another type of therapy such as CPAP therapy. For example, the baseline measure of respiratory events can be a frequency of respiratory events or an AHI.

Optionally, the operations can further include determining whether to perform a titration for oral appliance therapy during one or more additional test periods based on diagnostic information concerning the subject, a desired outcome of oral appliance therapy, a desired level of accuracy for the outcome of oral appliance therapy, a desired total number of test periods, a sensitivity or tolerance of the subject, or a constraint of an adjustable mandibular displacement device. For example, the operations can optionally include identifying a variable associated with the titration performed during the second test period, and determining whether to perform a titration for oral appliance therapy during a third test period based on the variable associated with the titration performed during the first or second test period. When the titration for oral appliance therapy is performed during the third test period, the operations can optionally include setting a parameter for the titration for oral appliance therapy to be performed during the third test period, and performing the titration for oral appliance therapy during the third test period. Similar to above, the parameter can be dependent on the variable associated with the titration performed during the first or second test period. In addition, the outcome of oral appliance therapy can be established based on the titrations performed during at least two of the first, second, and third test periods.

This disclosure contemplates that example operations described above can be performed using the titration system described with regard to FIGS. 1A-1B, for example. It should be understood that systems other than the titration system described with regard to FIGS. 1A-1B can be used. Techniques for performing titration for oral appliance therapy are described in detail above. For example, a titration during a test period can include positioning an adjustable mandibular displacement device in an oral cavity of a subject, monitoring physiological information from the subject, and adjusting a protrusion level of the adjustable mandibular displacement device.

Figure 10E:
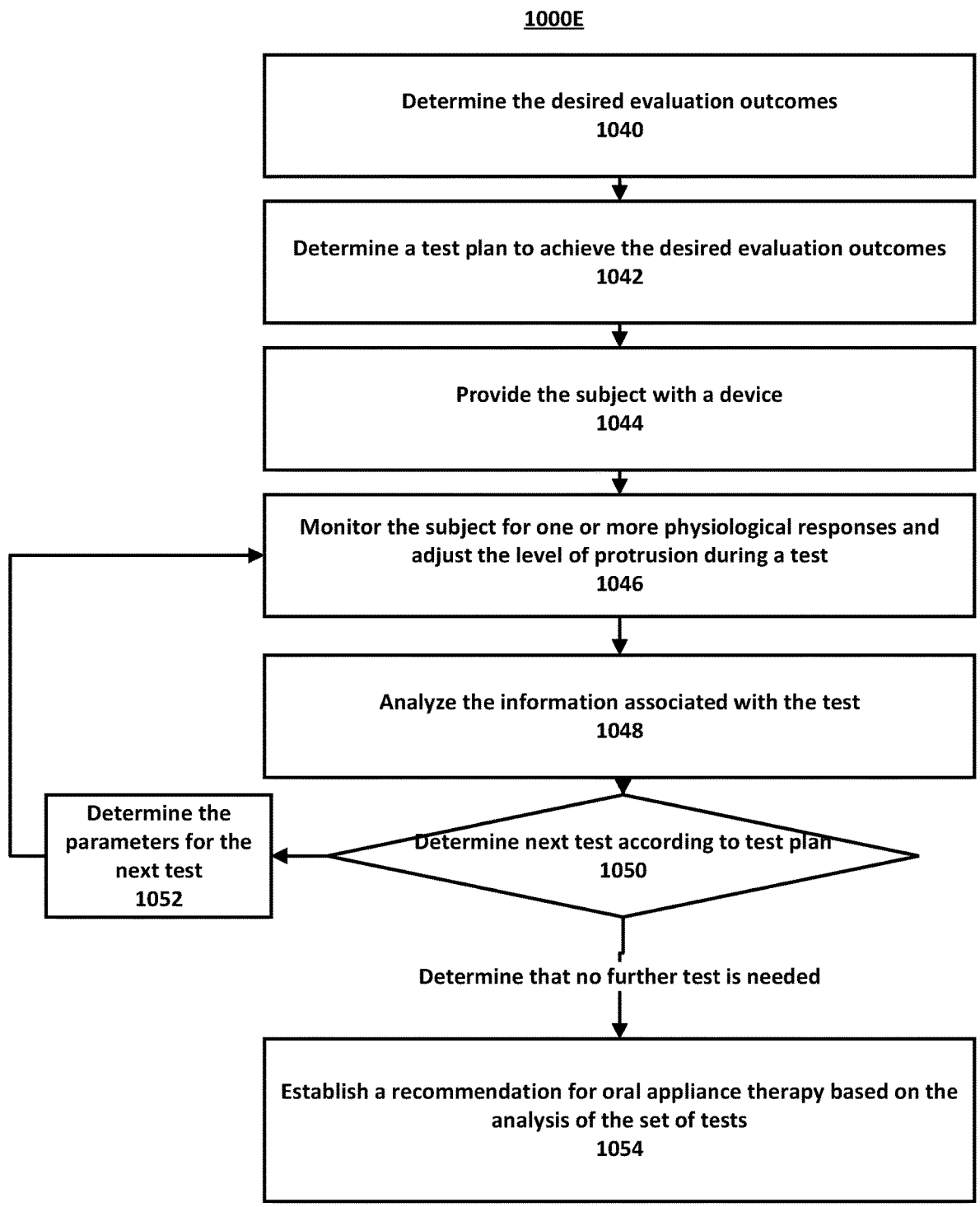
FIG. 10E is a flow diagram illustrating example operations for developing a multi night test plan.

Referring now to FIG. 10E, a flow diagram illustrating example operations 1000E for a multi night test plan is shown. Starting at 1040, the desired evaluation outcomes are assessed and at 1042, these desired evaluation outcomes are used to develop a test plan to achieve the desired outcomes. The desired outcome can include a desired outcome of oral appliance therapy (e.g., a certain measure of predicted therapeutic outcome such as AHI, ODI, % reduction, or combinations thereof), a desired level of accuracy for the outcome of oral appliance therapy, a desired total number of test periods, a sensitivity or tolerance of the subject, or a constraint of an adjustable mandibular displacement device. As described herein, the test plan can include the selection of adjustable mandibular displacement control techniques (and optionally one or more parameters associated therewith) based on the desired outcome. Alternatively or additionally, the test plan can include the selection of oral appliance therapy outcome prediction techniques based on the desired outcome. As described above, this can include devising a test plan where a particular test period is repeated and the results averaged to obtain an increased level of accuracy. Alternatively, it can include devising a test plan that includes a second, third or fourth etc. test period to confirm or refine the desired outcome. Alternatively or additionally, it can include devising a test plan that limits the number of total test periods to a minimum number, or omits a certain test period as it is not required to achieve the desired accuracy. The test plan can alternatively and optionally consider patient inputs (e.g., diagnostic information concerning the subject). Following the development of a test plan, the subject is provided with a device (e.g., the titration system described with respect to FIG. 1B) at 1044 and an adjustable mandibular displacement device can be positioned in an oral cavity of a subject. At 1046, the subject can be monitored for one or more physiological responses during the test period. Optionally, a physiological response can be a respiratory event, for example. Detecting respiratory events is discussed in detail above. For example, detecting a respiratory event includes defining and measuring physiological information from a subject against predetermined criteria. Additionally at 1046, a protrusion level of the adjustable mandibular displacement device can be adjusted during the test period. Methods for controlling the adjustable mandibular displacement device are discussed above including, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. Then, at 1048, the information from the test period is analyzed and one or more variables are calculated.

The information can be the physiological information and can include the comprehensive information, including the dynamic response of the motor driving the mandibular displacement device as described above. As described above, the variable(s) can include, but are not limited to, one or more of a predicted outcome of oral appliance therapy, a predicted effective protrusion level for oral appliance therapy, a predicted optimal protrusion level for oral appliance therapy, a measure of respiratory events such as a count or frequency of respiratory events (e.g., an apnea hypopnea index (AHI), such as $$\left(\frac{\text{\# of apneas and hypopneas}}{\text{period of time}}\right),$$

a measure of respiratory events at or above a specific protrusion level (e.g., Residual RDI as described above), a percentage of time spent at or above a specific protrusion level, a sleep stage, or an occurrence of arousal.

At 1050, the analysis from the test period is used to determine the next test according to the test plan. If at 1050 a next test is determined to be required, at 1052 the variable(s) determined from the analysis can be used to determine one or more parameters for the next test. As described above, the parameter can include, but is not limited to, a beginning protrusion level, a protrusion level adjustment rate, a protrusion level range, a width and/or position of a correlation window (e.g., lag time for detecting respiratory events as described above), a type of protocol, criteria defining a respiratory event (e.g., the predetermined criteria against which respiratory events are defined and measured as describe above), a sleep study qualifying condition, or a length of time before adjusting protrusion level. If alternatively, at 1050 it is determined that no further test periods are required at 1054, a recommendation for oral appliance therapy can be established based on the results of the one or more test periods.

As described above, the recommendation can be a prediction of whether the subject is a favorable candidate for oral appliance therapy. Alternatively or additionally, the recommendation can optionally be an indication of an effective protrusion level of the adjustable mandibular displacement device. An effective protrusion level of the adjustable mandibular displacement device can be a protrusion level that reduces the severity or frequency of respiratory events to an acceptable level. Alternatively or additionally, the recommendation can optionally be an indication of an optimal effective protrusion level of the adjustable mandibular displacement device.

The evaluation can be assessed based on the overall data set from the test period, which includes, but is not limited to, the physiological response of the subject and information regarding the dynamic response of the mandibular displacement device (e.g., how fast and how far the device moves during the test period) as previously described. As described above, the assessment can also include identification or determination of one or more variable associated with the test period.

The one or more variables can also affect the multi-period-test plan as described above. Optionally, the variables can also affect the conditions for the next test, for example, the variables can be used to set parameters for the protocol performed during a subsequent test period as described above. Optionally, the variables from the analysis of a test period can also be used in the final analysis of the full set of test periods in order to establish a recommendation for oral appliance therapy. The final analysis to establish a recommendation for oral appliance therapy can optionally and additionally consider patient inputs (e.g., diagnostic information concerning the subject), determined directly from the patient prior to the start of the test, or additionally or alternatively by a first type of test with the same device (e.g., a diagnostic test).

Figure 10F:
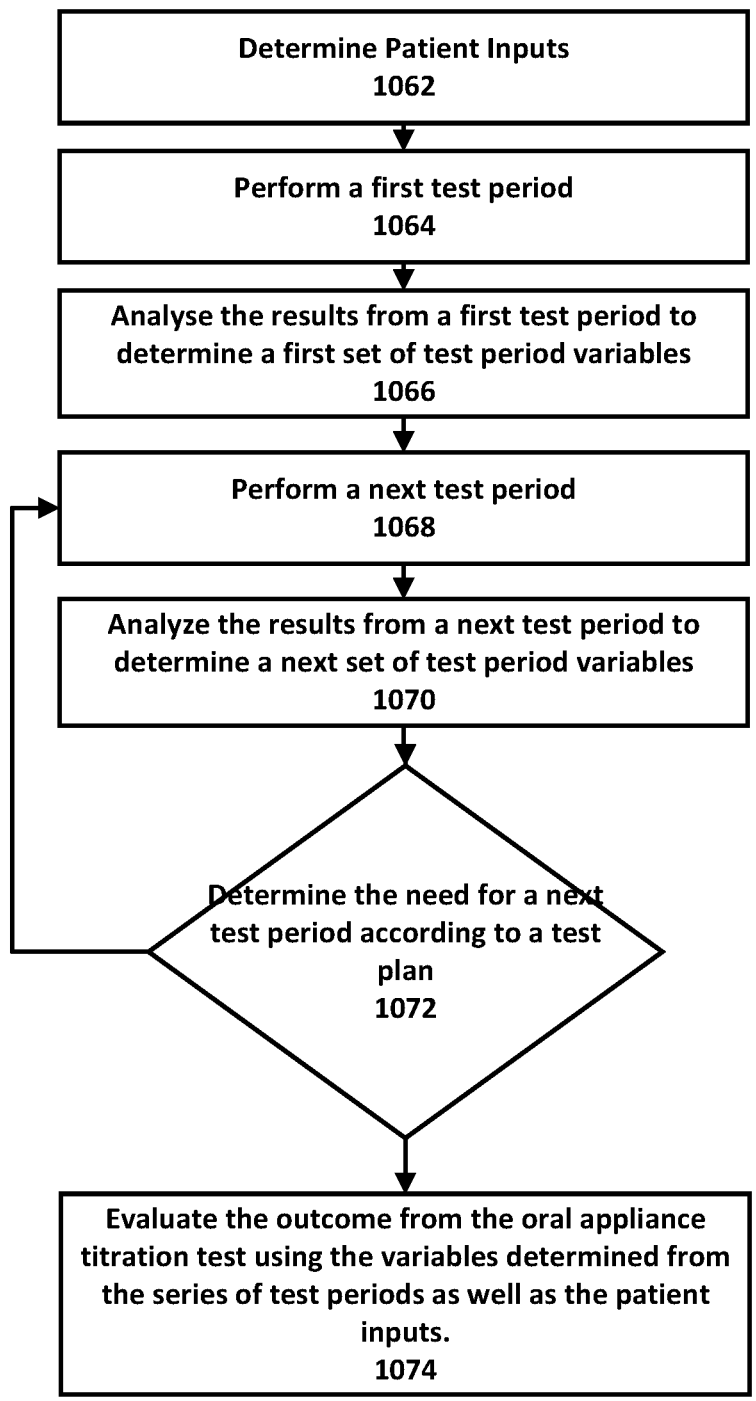
FIG. 10F is a flow diagram illustrating example operations for analysis of a multi-test-period protocol.

Referring now to FIG. 10F, a flow diagram illustrating example operations 1000F for analysis of a multi-test-period protocol is shown. At 1062, the patient inputs (e.g., diagnostic information concerning the subject) are optionally determined and reserved for subsequent analysis. The patient inputs can alternatively be collected at any time during the multi-test-period protocol prior to the final analysis. At 1064, a first test period is performed. The first test period can include steps previously described including providing an adjustable mandibular displacement device, monitoring physiological information from the subject, and adjusting the mandibular displacement device in response to the physiological information. At 1066, the results from the first test period are analyzed to determine a first set of test variables. The test variables can optionally include the test period outcome such as the prediction of whether the subject is a favorable candidate for oral appliance therapy, a first indication of an effective protrusion level of the adjustable mandibular displacement device (target protrusion) that reduces the severity or frequency of respiratory events to an acceptable level. Alternatively or additionally, the test period variables can include one or more of the variables associated with a test period as described above. At 1068, a next test period is performed. The test period includes steps previously described including providing an adjustable mandibular displacement device, monitoring physiological information from the subject, and adjusting the mandibular displacement device in response to the physiological information. At 1070, the results from the next test period are analyzed to determine a next set of test variables. The test variables include the test period outcome such as the prediction of whether the subject is a favorable candidate for oral appliance therapy, a first indication of an effective protrusion level of the adjustable mandibular displacement device (target protrusion) that reduces the severity or frequency of respiratory events to an acceptable level. Alternatively or additionally, the test period variables can include one or more of the variables associated with a test period as described above. At 1072, the need for additional tests are determined according to a test plan as previously described. At 1074, at the conclusion of the test plan, the variables from one or more of the test periods are used to establish a recommendation for oral appliance therapy. The final analysis to establish a recommendation for oral appliance therapy can optionally and additionally include patient inputs (e.g., diagnostic information concerning the subject), determined directly from the patient prior to the start of the test, or additionally or alternatively by a first type of test with the same device (e.g., a diagnostic test). Optionally, the type of final analysis can be selected based on the desired criteria for the recommendation for oral appliance therapy. For example, each of the following criteria for the recommendation for oral appliance therapy: an AHI<10, an AHI<10 with a 50% reduction from a diagnostic study, or the type of respiratory events used to calculate the RDI or AHI (e.g., 3% oxygen desaturation vs 4% oxygen desaturation, or desaturation events only etc.), can be associated with the selection of a different type of final analysis.

Figure 10G:
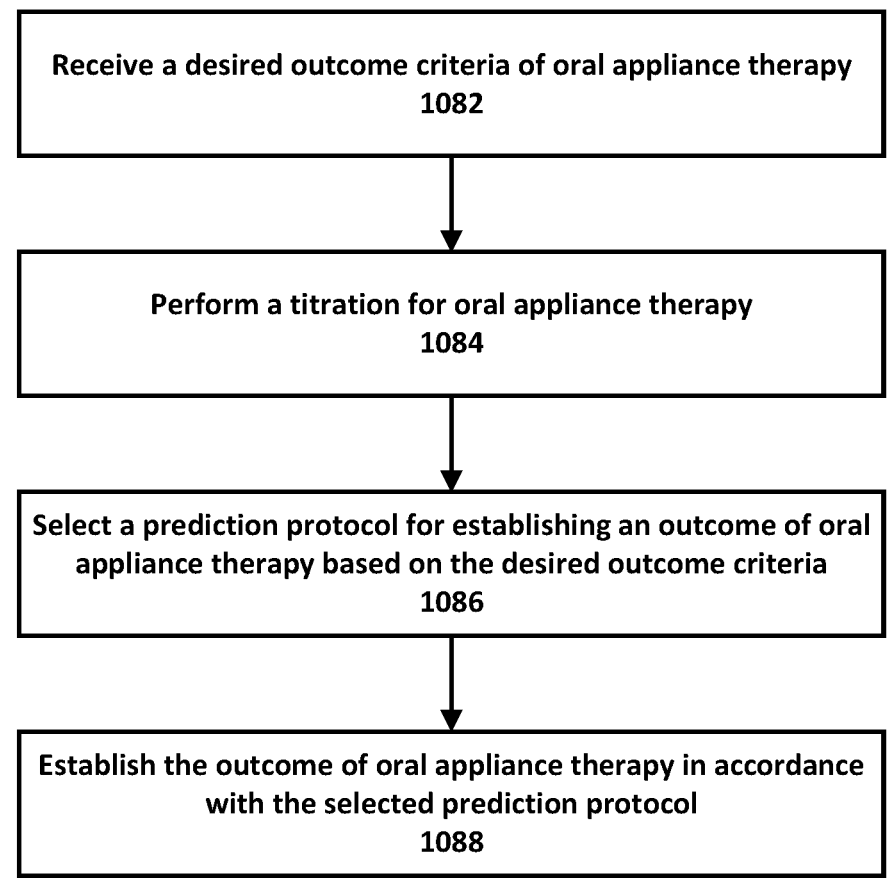
FIG. 10G is a flow diagram illustrating example operations for selecting oral appliance therapy outcome prediction protocols.

Referring now to FIG. 10G, a flow diagram illustrating example operations 1080 for selecting oral appliance therapy outcome prediction protocols is shown. At 1082, a desired outcome criteria of oral appliance therapy is received. The desired outcome criteria can optionally be selected by a user (e.g., the subject, a sleep technician, medical professional, and/or other person interested in the results of oral appliance therapy). The desired outcome criteria can include a desired outcome of oral appliance therapy, a desired level of accuracy for the outcome of oral appliance therapy, a desired total number of test periods, a sensitivity or tolerance of the subject, or a constraint of an adjustable mandibular displacement device. For example, the desired outcome criteria can be a measure of predicted therapeutic outcome such as AHI, ODI, % reduction, or combinations thereof. At 1084, a titration for oral appliance therapy is performed. As described herein, methods for controlling a mandibular displacement device during a titration for oral appliance therapy include, but are not limited to, increasing/decreasing protrusion level to reduce/eliminate respiratory events, controlling a protrusion level based on an amount of elapsed time (e.g., holding the protrusion level constant for a fixed period), controlling magnitude or rate of adjustment based on frequency and severity of respiratory events, optimizing airflow, etc. As described herein, during multi-test period protocols, the methods for controlling a mandibular displacement device can be different during different test periods.

At 1086, a prediction protocol for establishing an outcome of oral appliance therapy is selected based on the desired outcome criteria. Prediction protocols can include any method for relating variables associated with data collected during the one or more test periods to outcome of oral appliance therapy. Different types of prediction protocols include, but are not limited to, machine learning techniques such as neural networks, support vector machines, decision trees, random forests, etc. For example, a random forest of 150 decision trees (e.g., a first type of prediction protocol) can be used when the desired outcome criteria is a first measure of predicted therapeutic outcome for oral appliance therapy such as ODI of 4% with success criteria of less than 10 events/hour and 50% reduction from baseline, and a random forest of 100 decision trees (e.g., a second type of prediction protocol) can be used when the desired outcome criteria is a second measure of predicted therapeutic outcome for oral appliance therapy such as ODI of 4% with success criteria of only less than 10 events/hour. It should be understood that the prediction protocols and measures of predicted therapeutic outcome are provided only as examples and that others can be used in accordance with the techniques described herein. The example above is presented only to demonstrate the use of different prediction protocols in dependence on different desired outcome criteria.

At 1088, the outcome of oral appliance therapy is established in accordance with the selected prediction protocol. Additionally, as described herein, the prediction protocol can be used to analyze one or more of the variables associated with the data collected during one or more test periods (e.g., the variables illustrated by FIG. 12). In other words, the prediction protocol can be used to perform a final analysis on a complete data set collected during the one or more test periods. Optionally, the final analysis can be performed offline after conclusion of the one or more test periods.

Optionally, in some implementations, a test protocol (e.g., a method for controlling a mandibular displacement device) can be selected based on the desired outcome criteria. The titration for oral appliance therapy can be performed in accordance with the selected test protocol. It should be understood that the test protocol can be selected in addition to, or alternatively to, the prediction protocol. The desired outcome criteria of oral appliance therapy at 1082 can be received either before or after the completion of the titration for oral appliance therapy at 1084. For example, if the desired outcome criteria selection affects only an offline final analysis prediction protocol and not the test protocol, the desired outcome criteria can be received after completion of the titration for oral appliance therapy. If on the other hand, the desired outcome criteria selection affects both an offline final analysis prediction protocol and the test protocol, the desired outcome criteria can be received before performance of the titration for oral appliance therapy.

Referring now to FIG. 13, example operations 1300 for conducting a multi-test-period titration for oral appliance therapy is described. As described above, the multi-test-period titration can optionally be performed based on a test plan, which is developed earlier in time based on a number of factors including, but not limited to, the desired outcome, desired accuracy level, patient inputs, and/or known limitations. In particular, in FIG. 13, the outcome of the oral appliance titration is evaluated based on the analysis of one or more variables from within different test periods. The variables from within a test period are used to determine the parameters for a next test period, and the final evaluation comprises an analysis of the variables from various (e.g., one or more) test periods. The final evaluation include analyzing one or more of the variables associated with the various test periods (e.g., one or more of the variables illustrated by FIG. 12). Optionally, the final analysis can be performed offline after conclusion of the various test periods. Optionally, the final analysis can employ a machine learning technique such as a neural network, support vector machine, decision tree, random forest, etc. As described herein, the final analysis can use one or more trained machine learning modules. Alternatively or additionally, the type of final analysis can optionally be selected based on the desired outcome, and different types of final analyses can be performed based on the desired outcome. For example, a first type of final analysis can be performed when the desired outcome is a certain measure of predicted therapeutic outcome for oral appliance therapy (e.g., AHI<10 or ODI<10), while a second type of final analysis can be performed when the desired outcome is a different measure of predicted therapeutic outcome for oral appliance therapy (e.g., AHI<10 and a 50% reduction from baseline). The types of final analyses can include methods for relating variables associated with data collected during the multiple test periods to outcome of oral appliance therapy including but not limited to machine learning techniques such as neural networks, support vector machines, decision trees, random forests, etc. After determining the desired evaluation outcomes, for example as described with reference to FIG. 10E steps 1040 (including the desired outcome, desired accuracy, number of test periods, patient or device limitations, etc.), and devising a test plan, for example as described with reference to FIG. 10E step 1042, a first test period is performed at 1302. At 1304, the information from the test period is analyzed and the variables are assessed. In FIG. 13, one of the assessed variables is the predicted outcome for oral appliance therapy as assessed during the test period. If the outcome is assessed as a predicted success (PS) (as at 1306), the information from the test period is analyzed to determine a predicted effective target protrusion level for oral appliance therapy (at 1308). At 1310, this predicted effective target protrusion level is used as a parameter for the protocol performed in the next test period, specifically as the starting target protrusion level of the mandibular displacement device for the test. In contrast, if at 1312, the predicted outcome for oral appliance therapy is a predicted failure (PF), the starting protrusion level of the mandibular displacement device during the next test period (e.g., the parameter for the second test period) is set at a preselected protrusion level (at 1314). The preselected protrusion level is determined to be a level that provides the best chance at identifying an effective protrusion level for oral appliance therapy. Given that the subject is PF for oral appliance therapy at this stage, e.g., a value near maximum protrusion level for the subject is suggested. For example, the preselected protrusion level may be 90% of the subject's maximum range of protrusion. It should be understood that the preselected protrusion level can be more or less than 90% of the maximum. FIG. 13 steps 1302 through 1314 illustrate an example where the adjustable mandibular displacement device control technique (and in particular parameters thereof) are selected based on a variable associated with the first test period. In other words, the starting protrusion level for the second test period (e.g., the parameter for the second test period, which is a parameter for the adjustable mandibular displacement device control technique employed during the second test period) is selected in dependence on the variable (e.g., predicted outcome for oral appliance therapy) associated with the first test period.

At 1316, in accordance with the test plan, a second test period is performed. Following the completion of the second test period, at 1318, the information from the test period is analyzed and the variables are assessed. In FIG. 13, one of the assessed variables is the predicted outcome for oral appliance therapy as assessed during the second test period. If the outcome is assessed as a predicted success (PS) (at 1320), the information from the second test period is further analyzed to determine a predicted effective target protrusion level. At 1322, the final evaluation is performed and the subject is predicted to be a success based on the second test period (1316) confirming the result of the first test period (1302). Additionally, the effective target protrusion level is selected as the higher level determined by the first or second test period. Similarly, if as at 1324, the outcome is a predicted failure (PF), the final evaluation is performed at 1326, and the subject is predicted to be a failure based on the second test period (1316) confirming the result of the first test period (1302).

Back to the analysis of the second test period at 1318, if at 1328, the outcome is assessed as a predicted failure (PF), the outcome of the first test period (1302) has not been confirmed by the second test period (1316). In accordance with the test plan, a third test period may be performed to complete the evaluation. In FIG. 13, the test protocol of the second test period is repeated at 1336, and based on the outcome of the first and second test periods (e.g., the variable associated with the test periods) at 1306 (PS) and 1328 (PF), the test parameters for the protocol performed during the third test period are selected at 1330. Specifically, the starting or beginning level for the mandibular displacement device during the third test period is chosen as a preselected level of protrusion as opposed to an effective protrusion level assessed from the last test period (e.g., the first test period) at 1330. The preselected level of protrusion can be selected to ensure the best opportunity to identify an effective protrusion level given that the subject is PF for oral appliance therapy based on the second test period (e.g., 90% or near maximum protrusion level for the subject). Alternatively, if as in 1332, the outcome of the first test period (1302) has not been confirmed by the second test period (1316), the test protocol of the second test period is repeated at 1336 as a third test period. The starting position for the mandibular displacement device for the third test period (e.g., the parameter for the third test period) is chosen as a preselected protrusion less than the previously selected protrusion level. For example, if at 1314 90% maximum protrusion level for the subject was used as the beginning protrusion level for the mandibular displacement device during the second test period, at 1334 70% of the maximum protrusion level of the subject can be used as the beginning protrusion level for the mandibular displacement device during the third test period given that outcomes of the first and second test periods were contradictory, with the later test period indicating PS (at 1332). It should be understood that a starting protrusion level more or less than 70% of the maximum protrusion level for the subject can be used. At 1336, a third test period is performed with the parameters (e.g., the beginning protrusion level) set based on the variables identified from previous test periods (e.g., the first and second test period).

Following the third test period, in this example, the final evaluation is performed. First, the outcome from the third test period is assessed at 1338. At 1340, where a predicted failure (PF) is assessed based on the third test period, the final evaluation is a predicted failure (at 1342) based on the PF outcomes for the second and third test periods. In contrast if PF is assessed at 1344, the final outcome is a predicted success (PS), at 1346 despite this negative prediction at 1344. In this scenario, the outcome from the second test period, though not confirmed by the third test period, is taken to be the final outcome. The test periods revealed that oral appliance therapy at 90% of the maximum protrusion level for the subject is PS (e.g., at 1332) but oral appliance therapy at 70% of the maximum protrusion level for the subject is PF (e.g., at 1344). Thus, the oral appliance therapy at 90% of the maximum protrusion level for the subject is the final target protrusion level for oral appliance therapy. Alternatively, at 1348, if the outcome is a predicted success (PS), the final outcome (at 1350) is a predicted success (PS) based on the outcomes determined by the second and third test periods, and the target protrusion level for the mandibular displacement device is taken from the third test period, for example, because the lower level of protrusion for oral appliance therapy (e.g., 70% v. 90% of maximum) is PF. And finally, if at 1352, the outcome is a predicted success (PS), the final outcome at 1354 is also a predicted success (PS), and the target protrusion level is taken as the higher of the levels from the first and third test periods. In this way, the greatest amount of accuracy is achieved, with the minimal amount of protrusive level, in the fewest amount of test periods.

Figure 14A:
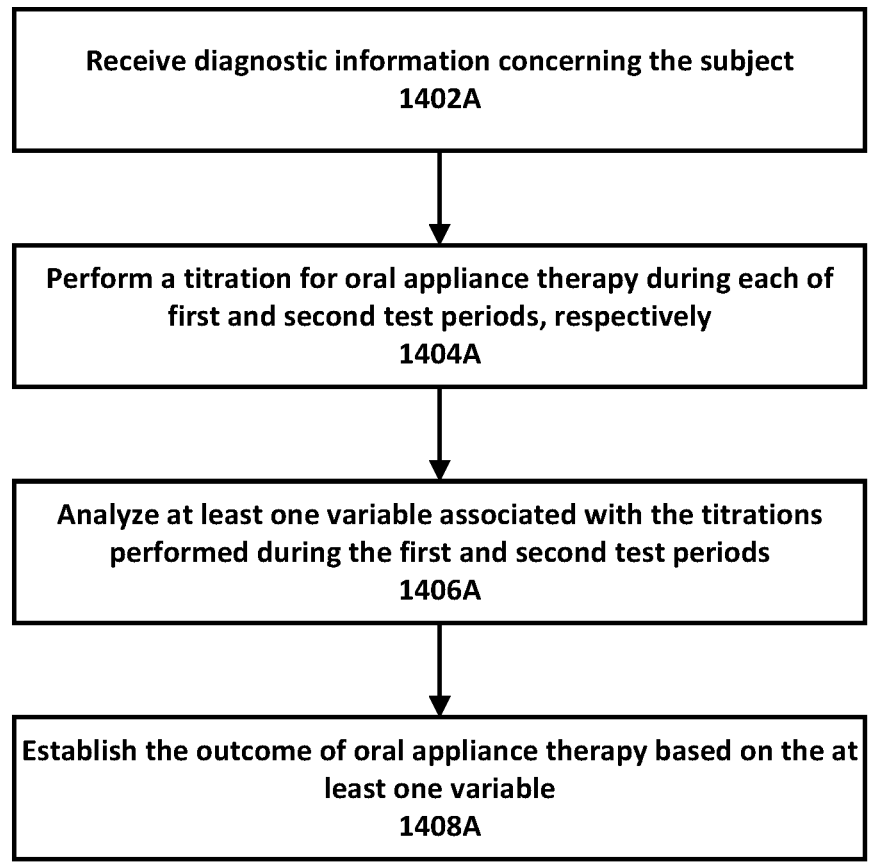
FIG. 14A is a flow diagram illustrating example operations for evaluating an outcome of oral appliance therapy in a subject using a multi-test-period titration.

Referring now to FIG. 14A, example operations 1400A for evaluating an outcome of oral appliance therapy in a subject using a multi-test-period titration is described. At 1402A, diagnostic information concerning the subject is received. At 1404A, a titration for oral appliance therapy during each of first and second test periods, respectively, is performed. At 1406A, at least one variable associated with the titrations performed during the first and second test periods is analyzed. In addition, the diagnostic information can influence selection of the at least one variable. At 1408A, the outcome of oral appliance therapy is established based on the at least one variable.

Optionally, the diagnostic information can be any information about the subject, including but not limited to a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms. For example, the diagnostic information can be obtained before (e.g., as a result of a diagnostic study). In one implementation described below with regard to FIG. 14B, the diagnostic information is a baseline apnea-hypopnea index (AHI) experienced by the subject in the absence of oral appliance therapy. The at least one variable can a first variable when the diagnostic information is greater than a threshold value, and the at least one variable is a second variable (e.g., different than the first variable) when the diagnostic information is less than a threshold value. As described above in step 1408A in FIG. 14A, the at least one variable influences the establishment of the outcome of oral appliance therapy. In other words, the prediction of whether the subject is a successful candidate for oral appliance therapy, the effective protrusion level for oral appliance therapy, the optimal protrusion level for oral appliance therapy, etc., can be determined by analyzing different variables, which depend on the diagnostic information concerning the subject (e.g., the subject's baseline AHI). The threshold value described above can optionally be between 15 and 40 respiratory events per hour. Optionally, the threshold value can be approximately 20 respiratory events per hour, for example, approximately 16 respiratory events per hour.

This disclosure contemplates that example operations described above can be performed using the titration system described with regard to FIGS. 1A-1B, for example. It should be understood that systems other than the titration system described with regard to FIGS. 1A-1B can be used. Techniques for performing titration for oral appliance therapy are described in detail above. For example, a titration during a test period can include positioning an adjustable mandibular displacement device in an oral cavity of a subject, monitoring physiological information from the subject, and adjusting a protrusion level of the adjustable mandibular displacement device.

Figure 14B:
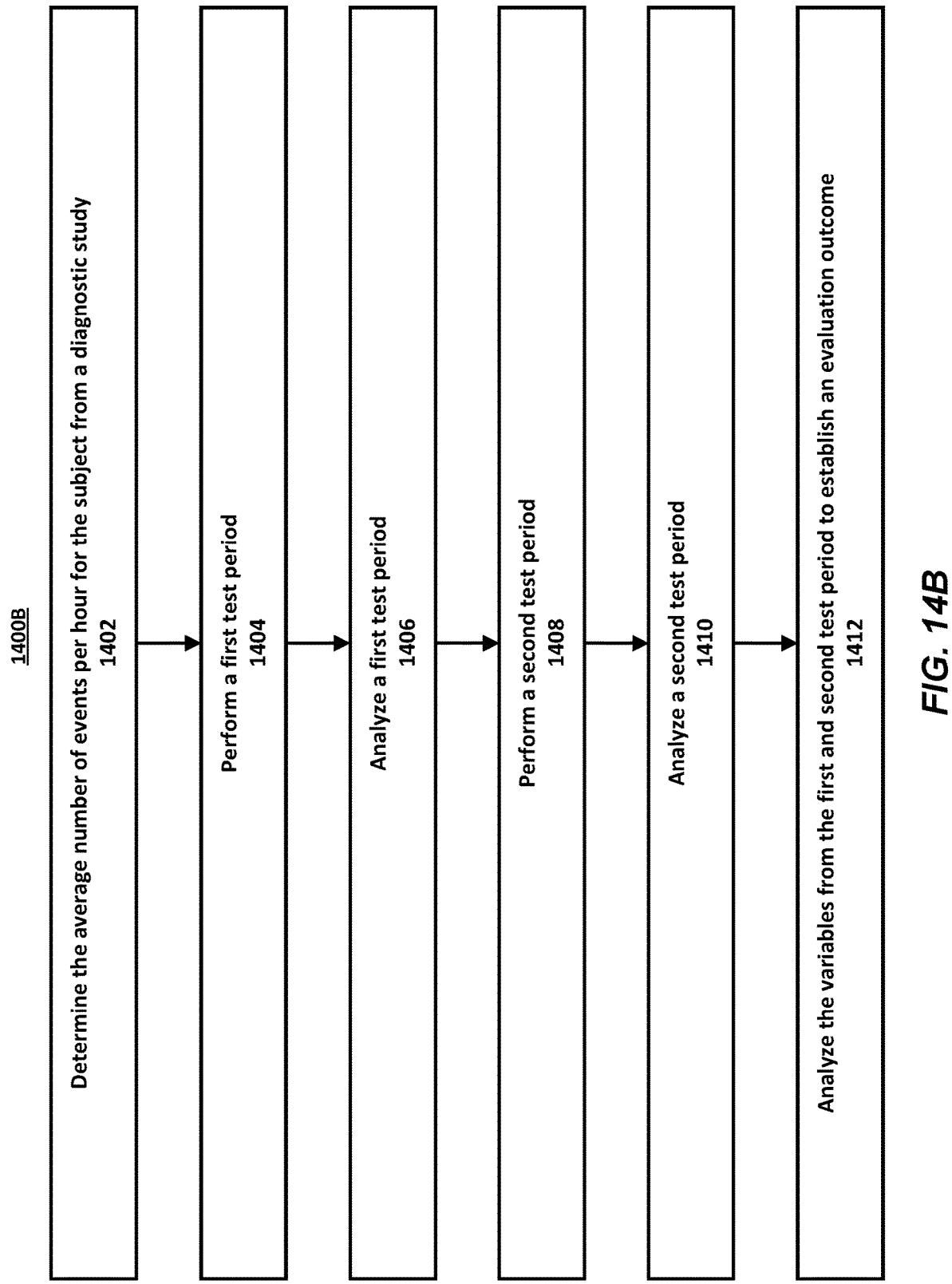
FIG. 14B is another flow diagram illustrating example operations for evaluating an outcome of oral appliance therapy in a subject using a multi-test-period titration.
Figure 14C:
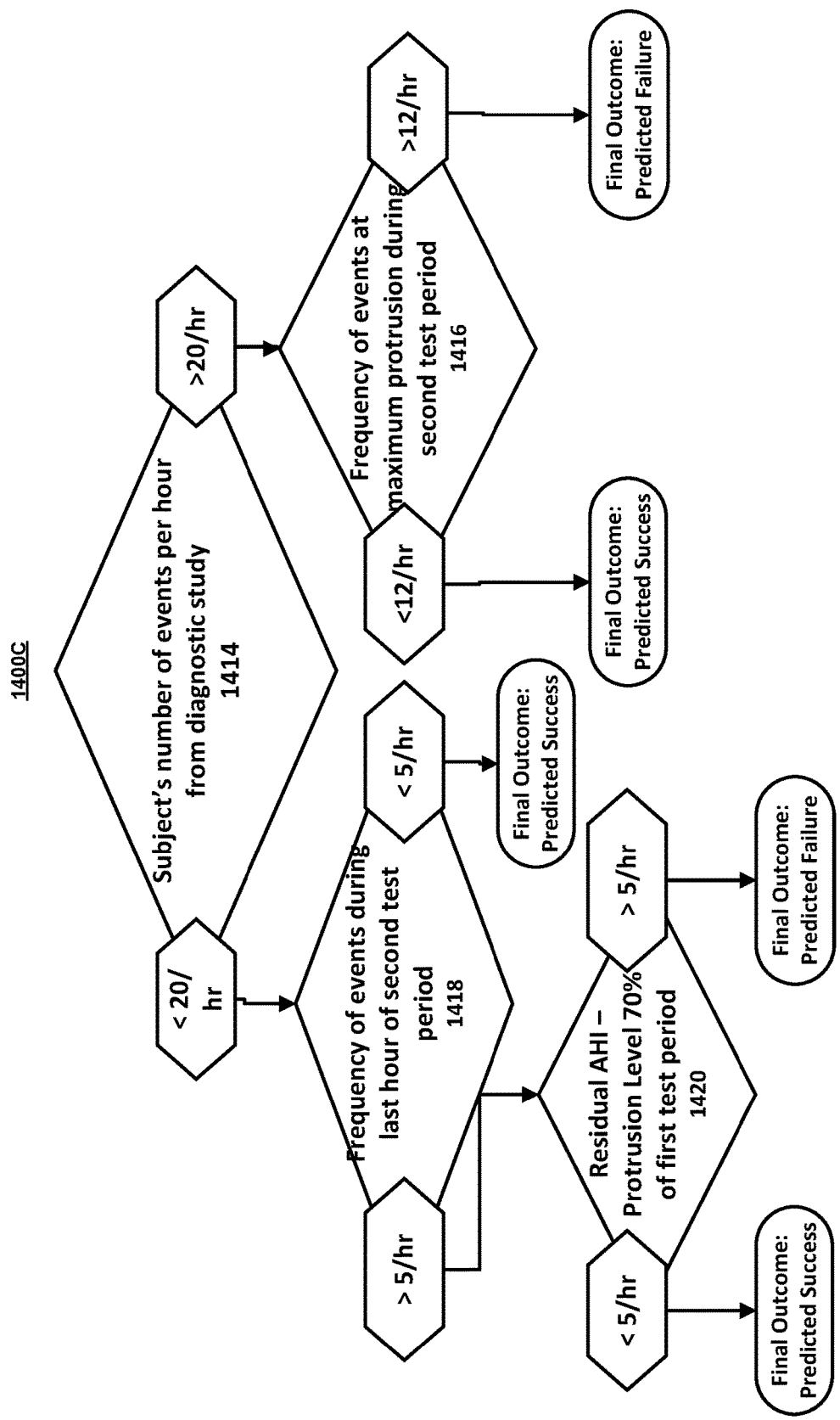
FIG. 14C is a flow diagram illustrating example operations for analyzing the patient input and one or more variables from the first and second test periods at step 1412 of FIG. 14B.

Referring now to FIG. 14B, example operations 1400B for evaluating an outcome of oral appliance therapy in a subject using a multi-test-period titration is described, where the final evaluation is determined based on an analysis of one or more variables from more than one test period and the patient inputs (e.g., diagnostic information from the subject). In the example, the patient inputs are determined outside of the titration test protocol, for example, during a diagnostic test protocol. At 1402, the patient inputs (e.g., diagnostic information from the subject) are determined. For example, the diagnostic information can be the average number of events per hour that were measured when the patient was not using oral appliance therapy (e.g., baseline Apnea-Hypopnea Index). At 1404, a first test period is performed (e.g., a titration for oral appliance therapy protocol), followed by the analysis of the first test period at 1406. At 1408, a second test period is performed (e.g., a titration for oral appliance therapy protocol), followed by the analysis of the second test period at 1410. It should be understood that the first, second, or additional test periods can be planned out in advance with all the possibilities as described above. Then, at 1412, the patient inputs at 1402 (e.g., the baseline AHI), the one or more variables from the first test period analysis at 1406, and the one or more variables from the second test period analysis at 1410 can all be used to establish an outcome for oral appliance therapy.

Referring now to FIG. 14C, example operations 1400C for analyzing the patient input and one or more variables from the first and second test periods at step 1412 of FIG. 14B are described. For example, at 1414, the diagnostic information from the subject (e.g., the baseline AHI) is analyzed. If the patient's AHI measured in advance of the oral appliance titration study is greater than 20 events per hour, the frequency of respiratory events at maximum protrusion during the second test period (e.g., the at least one variable associated with the second test period) can be evaluated at 1416. It should be understood that the threshold value against which the diagnostic information is compared (e.g., 20 events per hour) is provided only as an example and that the threshold value can be more or less than 20 events per hours, for example, between 15 and 40 events per hour or optionally approximately 16 events per hour as described above. If the frequency of respiratory events at 1414 is greater than 12 events per hour, the final outcome for oral appliance therapy was predicted to be a failure. If the frequency of respiratory events at 1414 is less than 12 events per hour, the final outcome for oral appliance therapy was predicted to be a success. It should be understood that the variable associated with the second test period (e.g. the frequency of respiratory events at maximum protrusion during the second test period) and the threshold of 12 events per hour are provided only as example. This disclosure contemplates that the variable can be any variable associated with a test period as described above and that the threshold can have other values.

Alternatively, at 1414, if the patient's AHI measured in advance of the oral appliance titration study was less than 20 events per hour, the frequency of respiratory events during the last hour of the second test period (e.g., the at least one variable associated with the second test period) can be evaluated at 1418. If the frequency of respiratory events at 1418 is less than 5 events per hour, the final outcome for oral appliance therapy was predicted to be was a predicted success. Similar to above, it should be understood that the variable associated with the second test period (e.g. the frequency of respiratory events during the last hour of the second test period) and the threshold of 5 events per hour are provided only as example. This disclosure contemplates that the variable can be any variable associated with a test period as described above and that the threshold can have other values.

If the frequency of respiratory events at 1418 is greater than 5 events per hour, the residual AHI at a protrusion level during the first test period at, or below, which the mandibular displacement device spends 70% of the time can be evaluated at 1420 before establishing the predicted outcome of oral appliance therapy. This protrusion level is referred to as "Residual AHI—Protrusion Level 70%" in FIG. 14C. As used herein, the residual AHI is, $$\frac{\text{\# Apneas and hypopneas at or greater than protrusion level}(i)}{\text{Length of time spent at or greater than protrusion level}(i)},$$

where "i" is a given level of protrusion. A frequency of greater than 5 events per hour resulted in final evaluation outcome of a predicted failure for oral appliance therapy, while a frequency of less than 5 events per hour resulted in a final evaluation outcome of a predicted success for oral appliance therapy. Similar to above, it should be understood that the variable associated with the first test period (e.g. the maximum residual AHI during the first test period) and the threshold of 5 events per hour are provided only as example. This disclosure contemplates that the variable can be any variable associated with a test period as described above and that the threshold can have other values. In this example, the analysis plan (e.g., the specific diagnostic information and variables analyzed from the first and second test periods) was established through a retrospective analysis of patient data.

Example Test Protocols

Example test protocols to be used during the test periods described herein are provided below. These protocols are provided as examples only and not intended to be an exhaustive list. It should be understood that control of the mandibular displacement device (e.g., the mandibular displacement device described in FIGS. 1A-1B) during each of the protocols described below is intended to achieve a different objective. Additionally, the final evaluation of outcome (e.g., the prediction) can be a combination analysis performed on variables collected using each of the test protocols.

Dynamic Control Protocol:

During a first portion of the protocol, the mandibular displacement device is controlled quickly and aggressively to eliminate respiratory events. During a second portion of the protocol, the physiological system is optionally perturbed by arbitrary protrusion or retrusion of the mandible and ventilatory response to this perturbation is evaluated. This protocol allows for determination of an optimal protrusion beyond which further protrusion does not generate any increase in ventilation, and a critical protrusion which is equivalent to a minimal protrusion capable of eliminating all respiratory events at a particular phase of the subject's sleep. At no point is the mandibular displacement device controlled to displace the subject's mandible beyond upper and lower limits tolerated by the subject.

Static Control Protocol:

The static control protocol allows a greater number of data points to be collected at certain protrusion levels. The protocol can be used to confirm that the prediction regarding patient's response to OA therapy and/or the predicted effective protrusion level are correct and to allow for optimization or "tune-up" of the target value. The static control protocol can optionally include controlling a protrusion level based on an amount of elapsed time. For example, the protrusion level can be held constant for a fixed period such as a length of time before an REM period is expected (e.g., about 2 hours) to allow collection of data during such fixed period of time. The confirmation protocol employs a different strategy, where predicted target protrusion (e.g., the effective protrusion level for oral appliance therapy) is a starting point (e.g., as determined during a dynamic control protocol), and intervention occurs only if cumulative residual apnea-hypopnea index (AHI) is greater than a predefined threshold. Otherwise, perturbations are performed and results are logged, but the protrusion stays constant at the target value. At no point is the mandibular displacement device controlled to displace the subject's mandible beyond upper and lower limits tolerated by the subject.

Refinement Control Protocol:

The target refinement protocol is intended to test a subject at a protrusion range lower than the target value at which they are a confirmed success. In some scenarios, the lower range of protrusions, e.g., 70-90% of maximum, may not be fully explored during evaluation and confirmation protocols described above and the target value (e.g., the effective protrusion level for oral appliance therapy) is chosen above 90% of maximum protrusion. The target refinement protocol can explore possibility of lowering predicted protrusion value below 90%. The general control of the mandibular displacement device is very similar to the confirmation protocol, except that when the cumulative residual AHI is evaluated, only events with an oxygen desaturation greater than a threshold (e.g., 4% or more) will be considered. The starting protrusion level is 70% and the upper limit is set at 90% of maximum protrusion value for the subject. At no point is the mandibular displacement device controlled to displace the subject's mandible beyond upper and lower limits tolerated by the subject.

Multi-Purpose Test Protocol

As discussed herein, a multi-purpose test protocol provides a different type of outcomes in addition to the recommendation for oral appliance therapy. Optionally, the different outcome may be used to establish patient inputs (e.g., diagnostic information from the subject) to the oral appliance titration test as described above, or may be separately used in the care of the patient. For example, in addition to a recommendation for oral appliance therapy the test protocol may provide a diagnosis for sleep disordered breathing. The diagnosis may be one of obstructive sleep apnea, central sleep apnea, or inspiratory flow limitation, high upper airway resistance, snoring or other. Optionally or alternatively, the different outcome may be a screening test that provides a measure of sleep disordered breathing (e.g., number of events, presence of snoring, incidence of central sleep apnea, presence of high upper airway resistance, etc.) without providing a full diagnosis. The screening can optionally be used to recommend that the patient proceed with the oral appliance titration test, or may provide the subject with the recommendation to pursue additional or alternative care for a possible condition.

The multi-purpose test protocol can be carried out by completing a plurality of different tests. The tests can be performed in succession from one test to the next in a single session, or alternatively in separate sessions. The tests can be performed in a single night, or may be performed on separate nights. Optionally, as described below, the tests can be performed using the same device, which can be configured to automatically execute the different tests without intervention by a sleep professional. For example, the device can be configured to perform a diagnostic study and optionally provide instructions to the subject for configuring the device for the same. Then, based on the outcome of the diagnostic study, the device can be configured to perform a titration study and optionally provide instructions to the subject for configuring the device for the same.

The outcome to proceed with the different test may be determined based on the outcome of the first test. For example, a first test that is a diagnostic test for sleep disordered breathing may be used to determine that the subject should proceed with an oral appliance titration test if the subject has a condition that could be treated by oral appliance therapy. The decision may be based on the subject having a certain threshold of the condition (for example, a certain number of respiratory events per hour) that meets a clinical disease threshold (for example >5 events per hour, >10 events per hour, >15 events per hour) or disease definition (for example AHI measured using a 3% desaturation index vs a 4% desaturation index, with or without airflow). Additionally, the decision may be based on the subject meeting certain conditions for the test. For example, the first type of test may measure the presence and number of central sleep apnea events. It may be decided to proceed with the oral appliance titration test based on the number of central sleep apnea events being below a certain threshold (for example less than 50% of the events being central). In a second example, the first type of test may measure the ratio of types of respiratory events (e.g. Ratio of apneas to hypopneas, ratio of obstructive events to central events.) In a third example, the first type of test may measure the body position during sleep and determine the frequency of respiratory events associated with each position. The decision to proceed with oral appliance therapy may be based on whether the frequency and/or severity of events is greater in one position than in the other. For example, the decision to proceed can be based on whether the frequency is greater in the supine position rather than the lateral position. Optionally, certain measures or variables from the first test (for example a diagnostic test) may be used to determine the test parameters, the test plan, and/or the analysis methods used in the oral appliance titration test. For example, the frequency of respiratory events in the diagnostic test can be used to determine the method used in the analysis of one or more of the test periods for the oral appliance titration test as described with reference to FIGS. 14A-C.

The decision to proceed from the first type of test (e.g., the diagnostic test) to the second type of test (e.g., the titration test) can be done automatically. For example, the device may automatically analyze the data from the first type of test (e.g., diagnostic test) and configure the device with the settings necessary to start the second type of test (e.g., oral appliance titration test). This can optionally be performed without intervention by a sleep professional. For example, the device may set the protocol to control the movement of the mandibular displacement device for the titration test. Optionally, the device can provide instruction to the patient to proceed with a next test that requires that the patient to place the oral appliance titration trays of the mandibular displacement device in the mouth during the test. The device can optionally request that settings be provided, for example, patient limits of protrusion or a starting position for the test. The device can optionally request these settings from the patient directly or from a trained operator. As described in detail above, the device can be configured to analyze data from the test period(s) and identify variable(s) and/or set parameter(s) for protocols, e.g., establish settings for the protocols. Optionally, the device can be configured to connect to a communication network in order to receive these settings from an operator remotely and/or a remote server. It should be understood that the device can include the computing device described with regard to FIG. 11, which includes components for communicating over a communication network. Optionally, the outcome from the first type of test (e.g., a diagnostic test) can be confirmed by a trained operator or professional (e.g., sleep physician, technician, dentist, etc.). This disclosure contemplates that the operator or professional can receive the data associated with the test periods over a communication network to which the device is connected as described above such that the operator or professional can review the data remotely, providing instructions back to the device over the communication network.

Optionally, in the first test (e.g., the diagnostic test), the patient does not use, or is not provided with, a mandibular displacement device including titration dental trays (e.g., the adjustable mandibular displacement device 10 described in FIGS. 1A-1B). Optionally, instructions are provided to the subject, for example using the device, to not place the mandibular displacement device in the mouth. Optionally, instructions are provided to the user, for example using the device, to configure one or more sensors (e.g., the monitoring unit 30 described in FIG. 1B) to measure the desired physiological information from the subject. In other words, the first test can include only of measurement of physiological signals from the patient (e.g., any of one or more of the physiological signals described herein such as airflow, oxygen saturation, EEG, etc.). In the second type of test (e.g., the oral appliance titration test), the subject uses, or is provided with, an adjustable mandibular displacement device (e.g., the adjustable mandibular displacement device 10 described in FIGS. 1A-1B). Optionally, instructions are provided to the subject, for example using the device, to not place the mandibular displacement device in the mouth. Optionally, instructions are provided to the user, for example using the device, to configure one or more sensors (e.g., the monitoring unit 30 described in FIG. 1B) to measure the desired physiological information from the subject. Optionally, the protrusion level of the adjustable mandibular displacement device can be adjusted during the second test period. Methods for controlling the adjustable mandibular displacement device are described herein, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. Alternatively or additionally, a recommendation for oral appliance therapy can be established based on the adjustment of the protrusion level of the adjustable mandibular displacement device during the oral appliance titration test period.

Figure 15A:
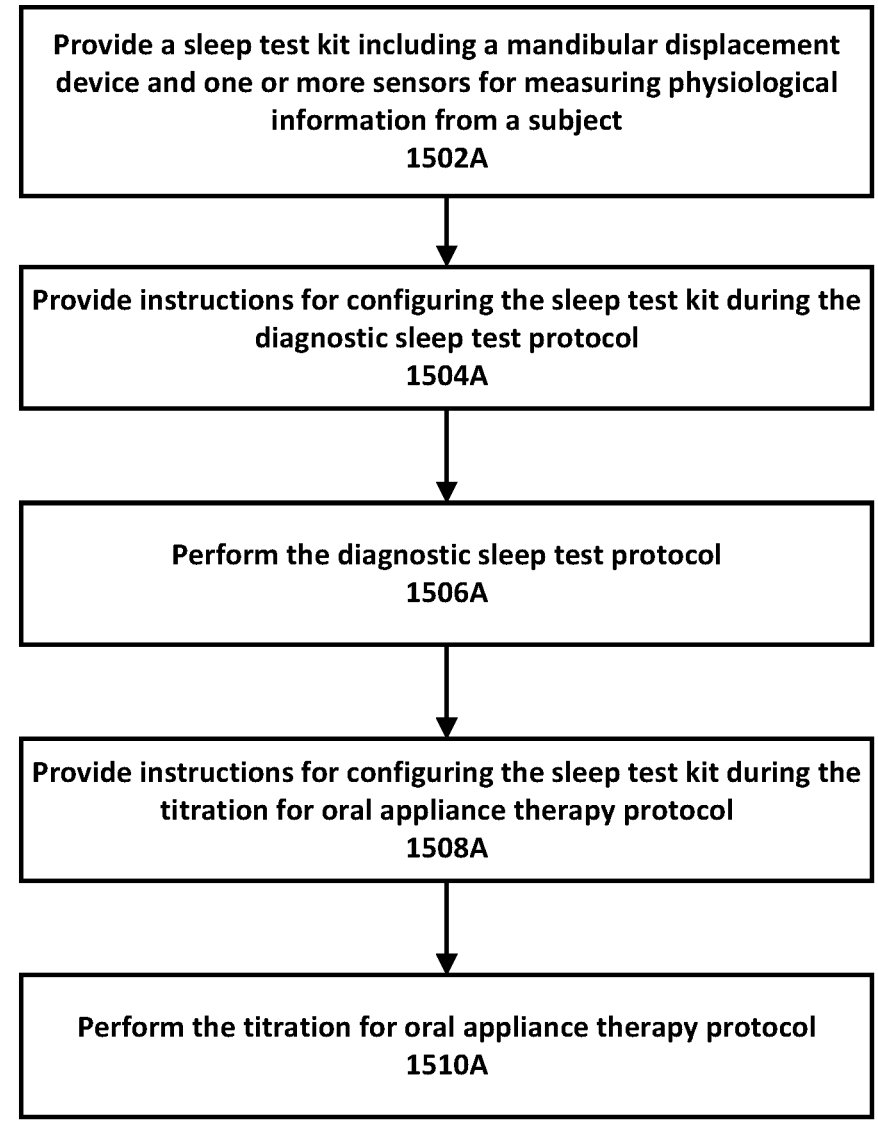
FIG. 15A is a flow diagram illustrating example operations for performing a multi-purpose sleep test protocol.

Referring now to FIG. 15A, example operations 1500A for performing a multi-purpose sleep test protocol is also described herein. At 1502A, a sleep test kit including a mandibular displacement device and one or more sensors for measuring physiological information from a subject (e.g., the titration system described in FIGS. 1A-1B) can be provided to the subject. The sleep test kit can be configured to perform a diagnostic sleep test protocol and a titration for oral appliance therapy protocol. At 1504A, instructions for configuring the sleep test kit during the diagnostic sleep test protocol can be provided to the subject. As described above, these instruction can optionally include not placing the mandibular displacement device in the mouth and/or how to use/configure one or more of the sensors for collecting the desired physiological information required by the diagnostic sleep test protocol. Optionally, these instructions can optionally be provided to the subject using the sleep test kit. For example, these instruction can be provided using a display device (e.g., visually) or speaker (e.g., audibly) of the mandibular displacement device. At 1506A, the diagnostic sleep test protocol can be performed, for example, automatically by the sleep test kit. At 1508A, instructions to the subject for configuring the sleep test kit during the titration for oral appliance therapy protocol. As described above, these instruction can optionally include placing the mandibular displacement device in the mouth and/or how to use/configure one or more of the sensors for collecting the desired physiological information required by the titration for oral appliance therapy test protocol. Optionally, these instructions can optionally be provided to the subject using the sleep test kit. For example, these instruction can be provided using a display device (e.g., visually) or speaker (e.g., audibly) of the mandibular displacement device. At 1510A, the titration for oral appliance therapy protocol is performed, for example, automatically by the sleep test kit. Additionally, the titration for oral appliance therapy protocol can be performed in dependence on an outcome of the diagnostic sleep test protocol as described above. For example, the variable analyzed, parameters of the protocols, number of test periods performed, etc. can be determined by the sleep test kit automatically.

Optionally, the diagnostic sleep test protocol and the titration for oral appliance therapy protocol can be performed automatically in succession. Alternatively or additionally, the diagnostic sleep test protocol and the titration for oral appliance therapy protocol can optionally be performed in a non-clinical setting as described above, for example, in the subject's home. Alternatively or additionally, the diagnostic sleep test protocol and the titration for oral appliance therapy protocol can be performed during a single sleep session. Alternatively, the diagnostic sleep test protocol and the titration for oral appliance therapy protocol can be performed during different sleep sessions. The different sleep sessions can be on the same night. The different sleep sessions can be on different nights.

Alternatively or additionally, the outcome of the diagnostic sleep test protocol can optionally be a measure of respiratory events. For example, the measure of respiratory events can be a number, duration, frequency, severity, or ratio of apneas or hypopneas.

Alternatively or additionally, diagnostic information concerning the subject can be received and used as part of either the diagnostic or titration for oral appliance therapy protocol. Optionally, the diagnostic information can be any information about the subject, including but not limited to a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms.

This disclosure contemplates that example operations described above can be performed using the titration system described with regard to FIGS. 1A-1B, for example. It should be understood that systems other than the titration system described with regard to FIGS. 1A-1B can be used. Techniques for performing a diagnostic sleep test protocol can include monitoring physiological information from the subject, and analyzing the physiological information to diagnose the subject with a sleep disordered breathing condition. The sleep disordered breathing condition can be obstructive sleep apnea (OSA), central sleep apnea (CSA), inspiratory flow limitation (IFL), high upper airway resistance (HUAR), upper airway resistance syndrome (UARS), or snoring. Techniques for performing a titration for oral appliance therapy protocol are described in detail above. For example, a titration during a test period can include positioning an adjustable mandibular displacement device in an oral cavity of a subject, monitoring physiological information from the subject, and adjusting a protrusion level of the adjustable mandibular displacement device. The outcome of oral appliance therapy can be a prediction of success or failure of oral appliance therapy, a predicted effective protrusion level for oral appliance therapy, or a predicted optimal protrusion level for oral appliance therapy.

Figure 15B:
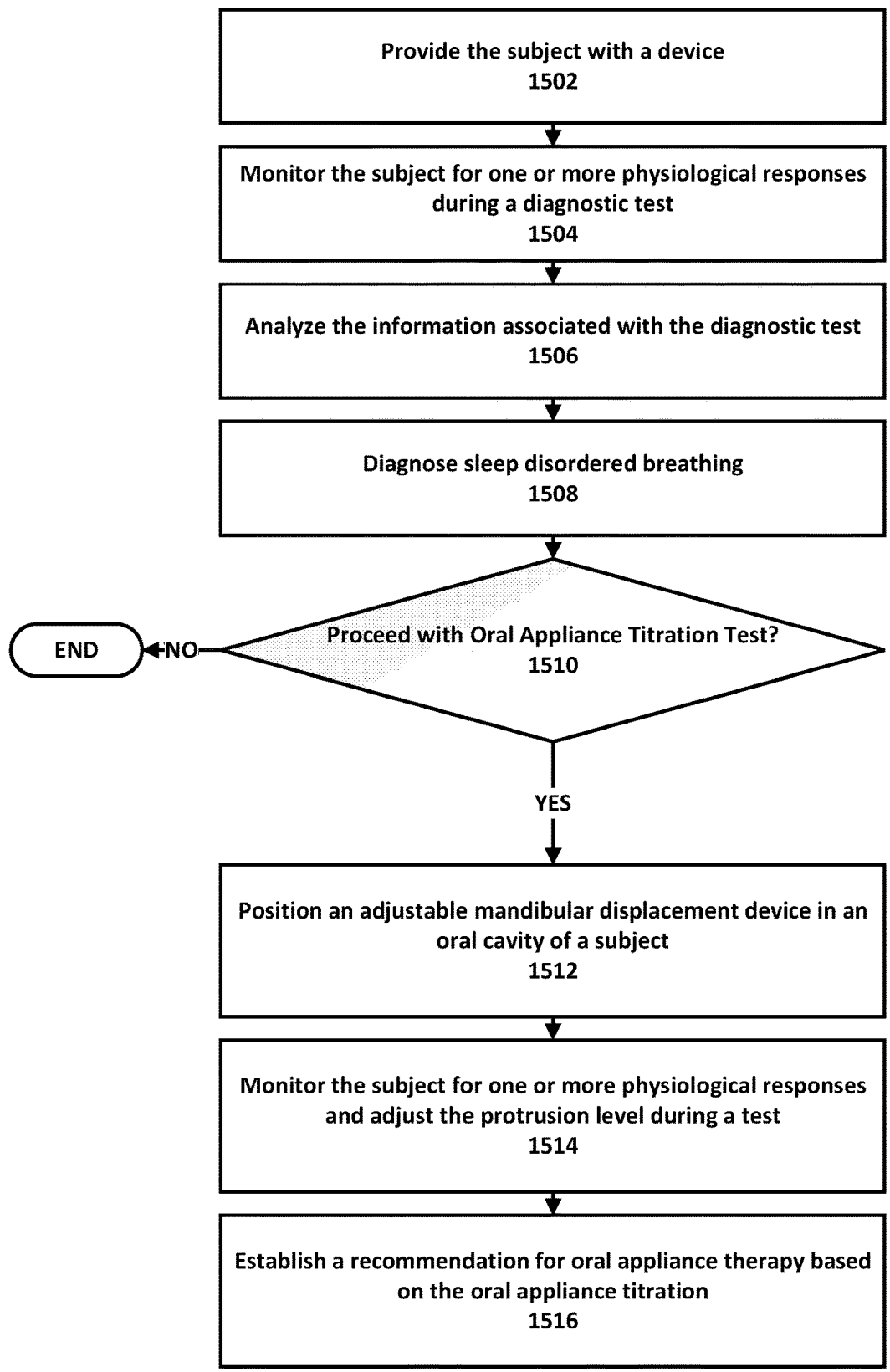
FIG. 15B is another flow diagram illustrating example operations for performing a multi-purpose sleep test protocol.

Referring now to FIG. 15B, example operations 1500B for performing a multi-purpose sleep test protocol is also described herein. At 1502, the subject is provided with a device such as the titration system described in FIGS. 1A-1B. At 1504, the subject can be monitored for one or more physiological responses during a first test type. The monitoring for this test type does not require real time monitoring, and instead the signals can be collected and recorded throughout the night. Optionally, a physiological response can be a respiratory event, for example. Detecting respiratory events is discussed in detail above. For example, detecting a respiratory event includes defining and measuring physiological information from a subject against predetermined criteria. At 1506, the physiologic response during the first test type can be analyzed. Optionally, at 1508, the analysis can be used to diagnose sleep disordered breathing, which can include but is not limited to obstructive sleep apnea (OSA), central sleep apnea (CSA), inspiratory flow limitation (IFL), high upper airway resistance (HUAR), upper airway resistance syndrome (UARS), or snoring. At 1510, the analysis and/or diagnosis from the first test type can be used to determine if the subject should proceed with a second test type, an oral appliance titration test. The decision to proceed may be based on the criteria described above (including a clinical diagnosis, requirement that certain conditions may be met, and/or the presence of certain conditions without a clinical diagnosis). Optionally, as described above, certain measures such as the patient inputs (e.g., diagnostic information from the subject) ascertained using the first type of test (e.g., the diagnostic test) can be used to set the conditions or parameter(s) for the oral appliance titration test. For example, the number of respiratory events per hour measured in the diagnostic test (e.g., the baseline AHI for the subject) can be used to guide the type of analysis performed in the oral appliance titration test as described with reference to FIGS. 14A-14C.

Depending the decision at 1510, an adjustable mandibular displacement device can be positioned in an oral cavity of a subject at 1512. At 1514, the subject can be monitored for one or more physiological responses during an oral appliance test period. Optionally, a physiological response can be a respiratory event, for example. Detecting respiratory events is discussed in detail above. For example, detecting a respiratory event includes defining and measuring physiological information from a subject against predetermined criteria. Additionally at 1514, a protrusion level of the adjustable mandibular displacement device can be adjusted during the first test period. Methods for controlling the adjustable mandibular displacement device are discussed above including, but not limited to, increasing/decreasing a protrusion level, controlling a protrusion level based on an amount of elapsed time (e.g., holding the protrusion level constant for a fixed period), controlling a protrusion level based on frequency or severity of respiratory events, optimizing respiratory airflow, etc. As described above, the subject can be monitored for one or more physiological responses during additional test periods according to the test plan. Then, at 1516, a recommendation for oral appliance therapy can be based on the results of the one or more test periods of the oral appliance titration test. Optionally, the recommendation for oral appliance therapy from the oral appliance titration test may rely on the information from the first test type. For example, whether the frequency or occurrence of respiratory events with oral appliance therapy is expected to change from the measure from the first test type (e.g., a 50% reduction from the baseline AHI).

Study Qualification

As discussed herein, a study qualification step can optionally be used to determine whether certain conditions of a test period have been met prior to recommending that the test plan continue with a subsequent test period. Optionally, if the conditions have not been met, the device (e.g., the mandibular displacement device described in FIGS. 1A-1B) can repeat a test period in order to obtain the required minimal conditions. Optionally, the test plan can be revised to accommodate the repeated test. For example, the test plan may be increased by an additional test period to accommodate the repeated test, or alternatively, the test plan can be revised to remove a previously planned test to keep the total number of test periods at the desired number. As described above, revising the test plan can affect the accuracy of the oral appliance recommendation, or can sacrifice the minimal protrusive target position determined from the oral appliance titration, or cause some other change to the final outcome.

The study qualification conditions can require that a minimal amount of study time has been achieved. For example, a minimum of 4 hours. It should be understood that the 4 hour minimum is provided only as an example and that the minimum can be more or less than 4 hours, such as a minimum between 3 and 5 hours, for example. The minimum study time can be continuous time (e.g., not interrupted by pauses by the subject, or occurrence of alarms indicating a missing physiological input or other interruptions). The minimum study time can alternatively be composed of fragmented portions collected between interruptions, including portions collected during multiple sleep sessions. Optionally, the non-continuous periods of sleep can be sleep during a plurality of test periods of the sleep study. Depending on the patient inputs (e.g., diagnostic information from the subject), the study qualification conditions can optionally require certain body positions during sleep such as sleep in the supine or lateral position and/or sleep of a certain stage such as REM or non-REM sleep. These patient inputs can be determined during a first test type (e.g., a diagnostic test) or a previous oral appliance titration test period. For example, the study qualification may require that the subject slept a certain portion of the night in a body position similar to that which was previously measured (e.g., >50% of the night supine, or >90% of the night supine, or <10% of the night supine). The study qualification conditions can optionally verify that certain failure conditions does not exist. For example, it may be required to demonstrate that the titration trays were in position for the entire duration of the oral appliance titration test, or some portion of the oral appliance titration test.

Figure 16A:
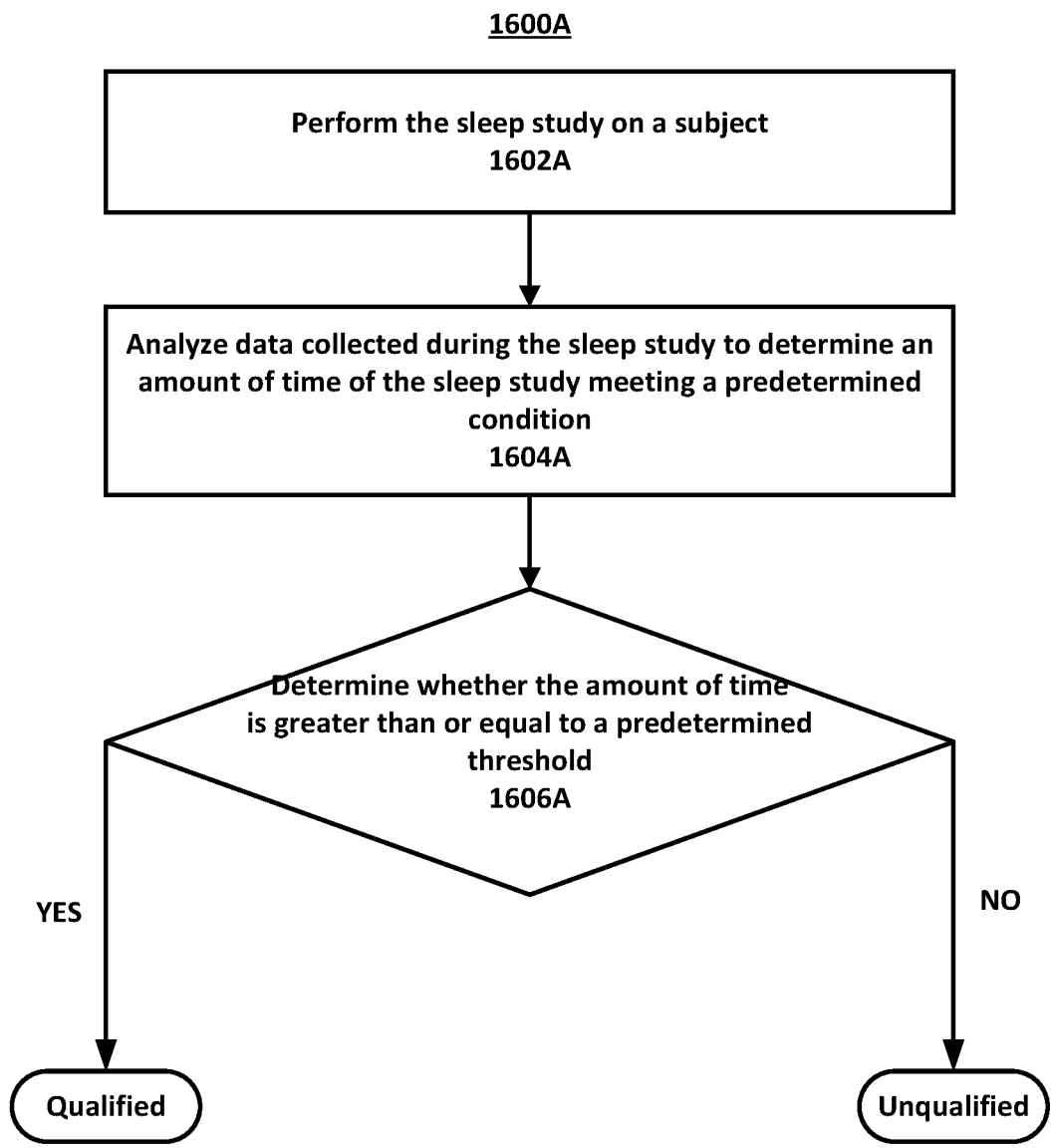
FIG. 16A is a flow diagram illustrating example operations for qualifying conditions of a sleep study.

Referring now to FIG. 16A, example operations 1600A for qualifying conditions of a sleep study are described. At 1602A, the sleep study is performed on a subject. The sleep study can include one or more test periods where a test protocol is performed as described above. At 1604A, data collected during the sleep study is analyzed to determine an amount of time of the sleep study meeting a predetermined condition. Then, at 1606A, a determination as to whether the amount of time is greater than or equal to a predetermined threshold can be made in order to qualify the sleep study. The predetermined threshold can optionally 4 hours as described above.

Optionally, if the amount of time is greater than or equal to the predetermined threshold, the sleep study is concluded. Alternatively, if the amount of time is less than the predetermined threshold, the sleep study continues, including performing another test period of the sleep study. Optionally, the another test period of the sleep study can be a repeat of a previous test period or a test period under conditions tailored to meeting the predetermined condition.

Alternatively or additionally, the predetermined condition can be sleep in a particular position, for example, sleep in a supine position or a lateral position. Optionally, the predetermined condition can be REM or non-REM sleep in the particular position.

Alternatively or additionally, the predetermined condition can be sleep with a mandibular displacement device fixed to the subject's teeth. Optionally, the operations can include sensing when the mandibular displacement device is fixed to the subject's teeth. In this case, the mandibular displacement device (e.g., the mandibular displacement device described in FIGS. 1A-1B) can include one or more force sensors for detecting force applied to the subject's teeth. Alternatively or additionally, it is possible to measure the energy supplied to the mandibular displacement device, which can provide an indication of the force applied to the subject's teeth.

Alternatively or additionally, the method can include providing an alarm (e.g., audible, tactile, and/or visual alarm) to the subject when the subject is not sleeping in the particular position or with the mandibular displacement device fixed to the subject's teeth. The mandibular displacement device (e.g., the mandibular displacement device described in FIGS. 1A-1B) can provide the alarm through a display device, speaker or other output unit. Alternatively or additionally, a notation can be provided in a data file associated with the subject, for example, using a computing device (e.g., computing device 50 of FIG. 1). The notation in the data file provides information about the conditions of the titration. The notation in the data file can be accessed during the final analysis or final evaluation and/or by a sleep technician.

This disclosure contemplates that example operations described above can be performed using the titration system described with regard to FIGS. 1A-1B, for example. It should be understood that systems other than the titration system described with regard to FIGS. 1A-1B can be used. Techniques for performing a diagnostic sleep test protocol can include monitoring physiological information from the subject, and analyzing the physiological information to diagnose the subject with a sleep disordered breathing condition. Techniques for performing a titration for oral appliance therapy protocol are described in detail above. For example, a titration during a test period can include positioning an adjustable mandibular displacement device in an oral cavity of a subject, monitoring physiological information from the subject, and adjusting a protrusion level of the adjustable mandibular displacement device.

Figure 16B:
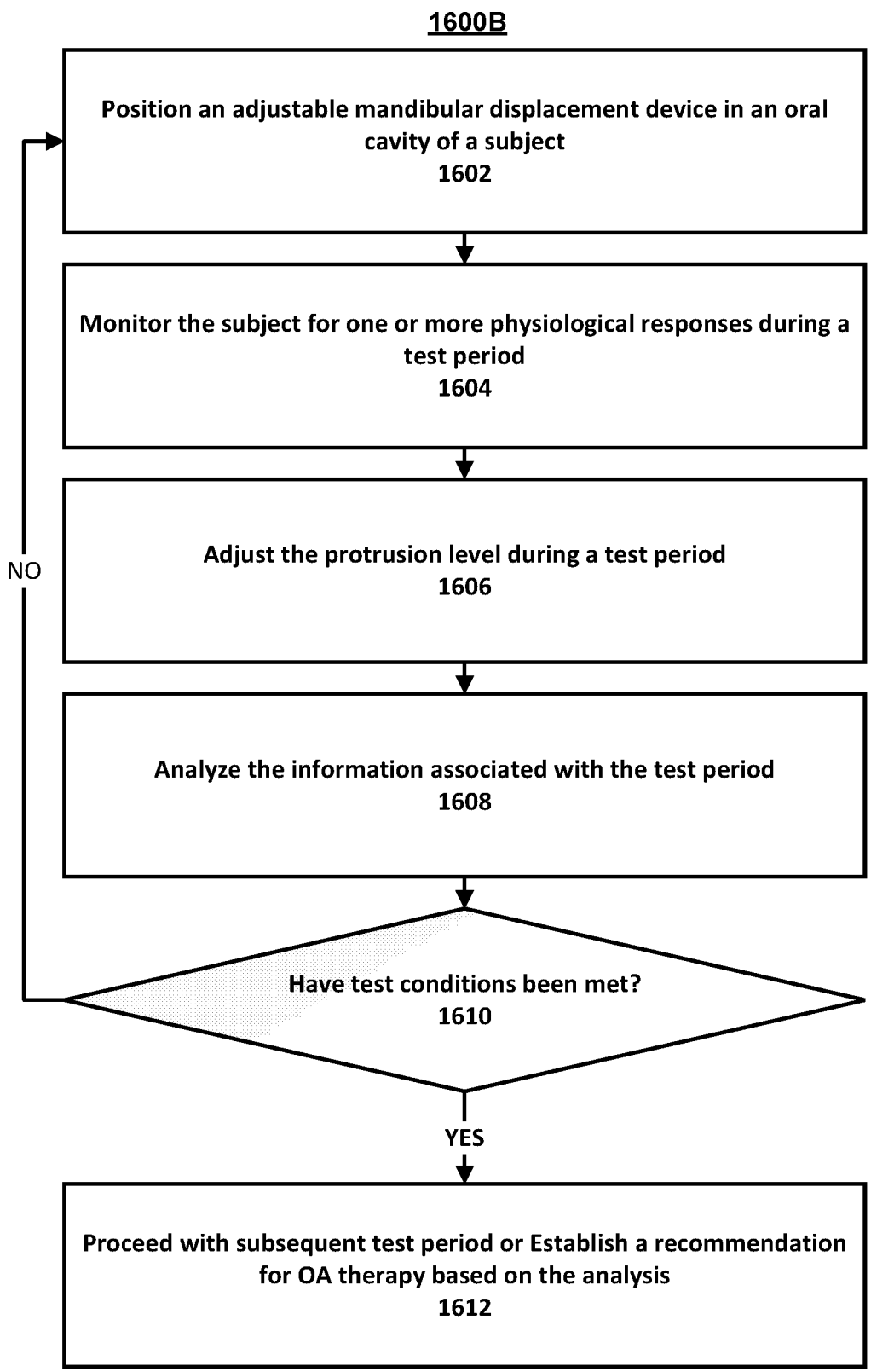
FIG. 16B is another flow diagram illustrating example operations for a study qualification.

Referring now to FIG. 16B, a flow diagram illustrating example operations 1600B for a study qualification is described. At 1602, an adjustable mandibular displacement device can be positioned in an oral cavity of a subject. At 1604, the subject can be monitored for one or more physiological responses during an oral appliance test period. Optionally, a physiological response can be a respiratory event, for example. Detecting respiratory events is discussed in detail above. For example, detecting a respiratory event includes defining and measuring physiological information from a subject against predetermined criteria. Additionally at 1606, a protrusion level of the adjustable mandibular displacement device can be adjusted during the test period. Methods for controlling the adjustable mandibular displacement device are discussed above including, but not limited to, increasing/decreasing a protrusion level, controlling a protrusion level based on frequency or severity of respiratory events, controlling a protrusion level based on an amount of elapsed time, optimizing respiratory airflow, etc. As described above, the subject can be monitored for one or more physiological responses during additional test periods according to the test plan. Then, at 1608, the data from the test period can be analyzed. The analysis can include measurements required to determine the satisfaction of the study qualification conditions, examples of which include minimum amount of study time, body position during sleep, presence of oral appliance titration trays firmly fixed to the subject's teeth. Then at 1610, the measures can be evaluated to determine if they meet the study qualification conditions. If they have been found to not meet the minimal conditions the decision can be made to repeat the test period, beginning again with 1602. Alternatively, the decision can be made to modify the test plan in accordance with the desired outcome conditions (e.g., accuracy of the outcome prediction, minimization of the target protrusive position, etc.) as described above. If at 1610, the measures were found to meet the study qualification conditions, the test plan can proceed as intended the test can proceed with the next test period, or a recommendation for oral appliance therapy can be based on the results of the one or more test periods of the oral appliance titration test.

Example Computing Device

It should be appreciated that the logical operations described herein with respect to the various figures may be implemented (1) as a sequence of computer implemented acts or program modules (i.e., software) miming on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 11:
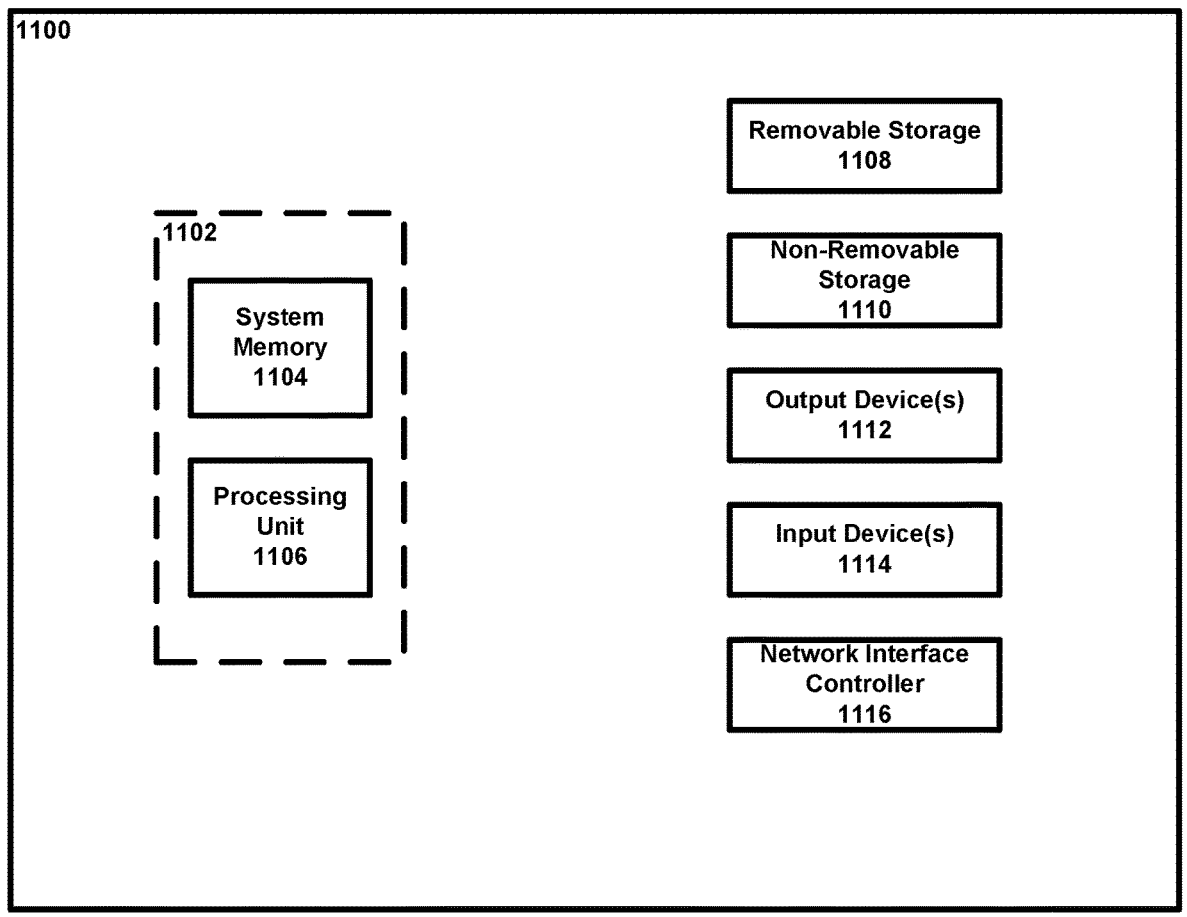
FIG. 11 is a block diagram of an example computing device.

When the logical operations described herein are implemented in software, the process may execute on any type of computing architecture or platform. For example, referring to FIG. 11, an example computing device upon which embodiments of the invention may be implemented is illustrated. For example, the mandibular displacement device controller 40 and/or the computing device 50 discussed with regard to FIG. 1 can be implemented as computing device 1100. The computing device 1100 may include a bus or other communication mechanism for communicating information among various components of the computing device 1100. In its most basic configuration, computing device 1100 typically includes at least one processing unit 1106 and system memory 1104. Depending on the exact configuration and type of computing device, system memory 1104 may be volatile (such as random access memory (RAM)), non-volatile (such as read-only memory (ROM), flash memory, etc.), or some combination of the two. This most basic configuration is illustrated in FIG. 11 by dashed line 1102. The processing unit 1106 may be a standard programmable processor that performs arithmetic and logic operations necessary for operation of the computing device 1100.

Computing device 1100 may have additional features/functionality. For example, computing device 1100 may include additional storage such as removable storage 1108 and non-removable storage 1110 including, but not limited to, magnetic or optical disks or tapes. Computing device 1100 may also contain network connection(s) 1116 that allow the device to communicate with other devices. Computing device 1100 may also have input device(s) 1114 such as a keyboard, mouse, touch screen, etc. Output device(s) 1112 such as a display, speakers, printer, etc. may also be included. The additional devices may be connected to the bus in order to facilitate communication of data among the components of the computing device 1100. All these devices are well known in the art and need not be discussed at length here.

The processing unit 1106 may be configured to execute program code encoded in tangible, computer-readable media. Computer-readable media refers to any media that is capable of providing data that causes the computing device 1100 (i.e., a machine) to operate in a particular fashion. Various computer-readable media may be utilized to provide instructions to the processing unit 1106 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1106 may execute program code stored in the system memory 1104. For example, the bus may carry data to the system memory 1104, from which the processing unit 1106 receives and executes instructions. The data received by the system memory 1104 may optionally be stored on the removable storage 1108 or the non-removable storage 1110 before or after execution by the processing unit 1106.

Computing device 1100 typically includes a variety of computer-readable media. Computer-readable media can be any available media that can be accessed by device 1100 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 1104, removable storage 1108, and non-removable storage 1110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1100. Any such computer storage media may be part of computing device 1100.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Example 1

A study to test the efficacy of an automated titration study was performed in the sleep clinic under the supervision of a technician.

Fourteen subjects were recruited and subjected to an overnight titration test at a sleep centre with the automated RCMP device. Each subject had previously received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays.

On the night of the automated titration study, a trained polysomnography technician entered the same values of retrusion and protrusion into the RCMP titration software. The titration trays were attached to the mandibular positioner and the position of the trays was adjusted by the manually adjustable knob to near full retrusion. The trays were then inserted into the subject's mouth and used for the duration of the titration study. Once the patient was asleep, the RCMP device was controlled with a decision making algorithm (e.g., in accordance with the implementations for conducting a titration for oral appliance therapy discussed above). The algorithm continuously receives feedback information (e.g., SaO2—oxygen saturation and naris specific air flow), automatically detects and classifies apneas and hypopneas, and makes moment-to-moment decisions regarding mandibular positioning.

The collected data was analyzed to identify if the residual RDI was below a threshold value of 10 events per hour at a protrusive level where the mandibular positioner spent at least 85% of the night at or above this level. Based on this analysis the subjects were predicted to be either a successful or unsuccessful candidate for oral appliance therapy, and a target protrusive position was determined.

The same fourteen patients had been previously studied with the manual RCMP. From the manual RCMP study, the subjects had been previously fitted with a permanent mandibular repositioning appliance (MRA) and tested in a post-treatment, respiratory evaluation during sleep using the same portable monitor used for baseline studies for two nights in the home with the mandibular repositioning appliance (MRA).

The prediction of success and the target protrusive distance from the automated titration study was compared with the therapeutic outcome of the patient as measured in the manual RCMP protocol. For those subjects predicted to be a success, the predicted target protrusive position was compared with the target protrusive position determined in the manual RCMP protocol.

All seven subjects predicted to be a success with the automated titration protocol were found to be a success with the permanent MRA. Five of the seven subjects predicted to be a failure with the automated titration protocol were correctly predicted (i.e., they did not achieve a therapeutic outcome with the permanent MRA) while two subjects that had been predicted to be a failure were incorrectly predicted (i.e., they did achieve a therapeutic outcome with the permanent MRA). Sensitivity was calculated as 78% and specificity was calculated as 100%.

Example 2

A study to test the efficacy of an automated titration study was performed unattended, in the home environment.

One hundred and fifty one subjects were recruited and subjected to a multi-night, in home titration test with the automated RCMP device. Each subject had previously received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays.

On the first night of the automated titration study, a clinical coordinator visited the home of the subject to set up the equipment and entered the values of retrusion and protrusion into the RCMP titration software. The titration trays were attached to the mandibular positioner and the position of the trays was adjusted by the manually adjustable knob to near full retrusion. The subject was shown how to place the trays in their mouth and how to wear the finger oximeter and the nasal cannulae. They were provided with a brief tutorial on how to run the software. Before going to sleep, the subject placed the trays into their mouth for the duration of the titration study. Once the patient was asleep, the RCMP device was controlled with a decision making algorithm (e.g., in accordance with the techniques for conducting a titration for oral appliance therapy discussed above). The algorithm continuously receives feedback information (e.g., SaO2—oxygen saturation and naris specific air flow), automatically detects and classifies apneas and hypopneas, and makes moment-to-moment decisions regarding mandibular positioning.

When the night study concluded, the data was automatically uploaded to a central server and accessed by a trained technician who analyzed the data to identify if the residual RDI was below a threshold value of 10 events per hour at a protrusive level where the mandibular positioner spent at least 85% of the night at or above this level. Based on this analysis the subjects were predicted to be either a successful or unsuccessful candidate for oral appliance therapy, and a target protrusive position was determined. If insufficient data was obtained (e.g., less than 4 hours), the night was repeated.

On the second night of the automated titration study, the clinical coordinator returned and set the device to run a confirmation protocol to test the evaluation from the first night. The protocol was set to hold the adjustable appliance at the determined target protrusive position, and would automatically adjust only if respiratory events above a certain threshold were detected. If the subject was predicted to be unsuccessful for oral appliance therapy, the protrusive position was held at a high protrusive position to verify the prediction. When the second night study concluded, the data was automatically uploaded to a central server and accessed by a trained technician who analyzed the data.

If the outcome from the first and second night conflicted, a third night was used to either refine the target protrusive distance or to establish a final prediction. Specifically, if the first night predicted the subject to be successful with oral appliance therapy, and the second night did not confirm the prediction, a third night was performed to repeat the second night protocol. If the success was confirmed, the target protrusive distance was selected as the higher from the first and third night. In contrast, if a subject predicted to be a failure with oral appliance therapy in the first night, and in the second night was found to be successful, it was the protocol from the first night that was repeated in order to refine and minimize the target. In some cases, an additional night was collected with the appliance set at an increased separation of the occlusal planes (7 mm instead of 3 mm) and the outcome was compared against the evaluation of outcome from the first night of study, to compare both the prediction and the target protrusive distance.

The subject returned to the dentist to be fitted with a permanent mandibular repositioning appliance (MRA) and tested in a post-treatment, respiratory evaluation during sleep using the same portable monitor used for baseline studies for two nights in the home with the mandibular repositioning appliance (MRA).

Of the 85 subjects that were predicted to be a success with oral appliance therapy, 79 achieved a therapeutic AHI of less than 10 per hour and a greater than 50% reduction from baseline. Of the 46 subjects that were predicted to be a failure with oral appliance therapy, 29 were correctly predicted (i.e., they did not achieve a therapeutic outcome with the permanent MRA) while 17 subjects that had been predicted to be a failure were incorrectly predicted (i.e., they did achieve a therapeutic outcome with the permanent MRA). Sensitivity was calculated as 82% and specificity was calculated as 83%. The target protrusive position was correctly predicted in 72 of 79 of the subjects that were predicted to be a success and achieved a corresponding therapeutic outcome. The third night of study was required in 18% of cases to resolve a conflict between the first and second night of study. In the cases where the third night of study was used to refine the target, the protrusive position was lowered by 2.5 to 4.0 mm by performing the third night.

Example 3

A study to test the efficacy of an automated titration study was performed unattended, in the home environment.

In the study described above (Example 2) the collected data was analyzed for occurrences of the attractor behavior. In subjects predicted to be successful with oral appliance therapy were found to have a greater number of instances of attractor behavior than subjects predicted to be unsuccessful with oral appliance therapy. For example, greater than five per hour instead of less than three per hour.

Example 4

A study to demonstrate an automated titration study for high upper airway resistance was performed in sleep clinic under the supervision of a technician.

One subject was recruited and subjected to an overnight titration test at a sleep centre with the automated RCMP device that had been specially modified to include accelerometers to measure body position and a microphone to detect acoustic energy. The subject had previously received a two night baseline, pre-treatment, respiratory evaluation in the home using a portable sleep monitor and had been evaluated by the dental co-investigator and fitted with upper and lower dental titration trays filled with the impression material. The dentist measured the maximum retrusion and protrusion values from the scale on the titration trays.

On the night of the automated titration study, a trained polysomnography technician entered the same values of retrusion and protrusion into the RCMP titration software. The titration trays were attached to the mandibular positioner and were then inserted into the subject's mouth and used for the duration of the titration study. Once the patient was asleep, the RCMP device was controlled with a decision making algorithm (e.g., in accordance with the techniques for conducting a titration for oral appliance therapy discussed above). The algorithm continuously receives feedback information (e.g., SaO2, sound, and naris specific airflow), and uses a trained neural network (e.g., the classifying system) to evaluate, in real time, if each recorded breath is flow limited. The outcome from this evaluation is then used to make moment-to-moment decisions regarding mandibular positioning including a series of protrusive searches in response to higher incidence of inspiratory flow limited breaths.

The collected data was analyzed to determine at what levels protrusive searches were successful at eliminating or minimizing the prevalence of inspiratory flow limited breaths. These were then combined to give an estimate for the optimal protrusive position to treat High Upper Airway Resistance.

Example 5

The study on 151 patients (Example 2) found that the device was able to positively identify candidates with a 93% accuracy (PPV), and sensitivity/specificity of 82% and 83% respectively. The overall error rate was 19% and the negative predictive accuracy was only 63%. The final data set was analyzed retrospectively in order to attempt to improve on these outcomes.

The data for the retrospective analysis was obtained from a clinical trial (n>150) aimed at testing the predictive accuracy of the titration method employing a computer controlled mandibular positioner (CCMP) in the home environment on newly recruited patients whose therapeutic efficacy with oral appliance therapy (OAT) was unknown. The methods were performed as described above.

The retrospective analysis was performed on 131 patients for whom the full data set was available (mean AHI=25.3±13.3 hr 5 hr$^{-1}$; mean BMI=30.1±5.0 kg/m$^2$) at the time.

The goals of the retrospective analysis was to design, if possible, a set of predictive rules allowing for minimization of the overall error rate, increase in sensitivity/specificity and positive/negative predictive values.

The analysis started with construction of 195 variables containing all critical information gathered during 2-3 nights of the titration process. The values of these variables were tabularized for 131 participants for whom we already had final therapeutic outcome. A machine learning technique was employed in order to find an optimal predictive model and to minimize the number of necessary variables. A retrospective classification tree model with imposed trunk branch criterion of 16.0-20.0 hr$^{-1}$ for baseline AHI and additional two branching points involving three additional variables reduced the overall error rate to 11% and provided values for sensitivity/specificity and P/NPV of 0.91/0.81 and 0.92/0.79. This represents an improvement over the previous results using a prospective data analysis. Thus, the retrospective model can to predict outcome of oral appliance therapy for other OSA patients outside of this population with same precision and accuracy.

The retrospective analysis made use of same physiological signals which were collected in the trial, for example, oxygen saturation and respiratory flow signal recorded individually for each nostril. A signal from a three-axial accelerometer was also recorded in order to determine head position. Fundamental signal processing leading to determination of the beginning and the end of inspiration for each individual breath, real time detection and classification of respiratory events, calculation of the magnitude and timing of the interventions were the same as in Example 2. Each of the 195 variables was examined and its temporal trajectory through the night and/or its graphical representation as a function of the mandibular protrusion was scrutinized. This examination facilitates focus on a specific aspect of information carried out by the variable which may be not captured or adequately amplified by the way the variable is used/interpreted presently. For example, when examining the plot of the residual AHI as a function of mandibular protrusion, it was noted that focus was only on the points where the value of this function dips below 10 events per hour. A new derivative variable reflecting the value of an absolute minimum of this function was derived. The meaning of this new variable is fundamentally different from the meaning of the original variable. Another example would be the value of AHI calculated for the length of the confirmation night. One may calculate this value: (i) for the whole length of the night starting with the moment when the mandible was protruded to a predefined target, (ii) for the length of time at the highest protrusion, (iii) for the last two hours of the study, or (iv) for the one hour at the highest protrusion. All four variables (i)-(iv) are highly correlated but at the same time each one magnifies different aspects of the study. Several new variables were also introduced such as a total number of attractors per hour, number of base attractors per hour, etc. As described above, FIG. 12 includes a table illustrating some of the variables.

The objective of the retrospective analysis is to create a universal predictive model capable of binary classification of each individual OSA patient, investigated according to original protocol, as potential responder (success) or non-responder (failure) to oral appliance therapy with high precision and accuracy.

A combined feature selection approach (e.g. filter, wrapper, or embedded method) approach to select an optimal sub-set of variables from 195 potential input variables was employed to find a specific model structure/technique best suited to depict experimental data. To find the best machine learning technique for our problem, three approaches were probed: artificial neural network (NN), support vector machine (SVM), and decision tree (DT). The simplest model was considered for each technique and no tuning was done at this stage. The respective overall error rate of these three model structures/techniques for the first 110 subjects was used to compare performance and was found to be as follows: NN 16.4%; SVM 20.0%; DT 13.6%. Accordingly, the Decision Tree approach was selected and focus was turned to tuning the technique.

Figure 17A:
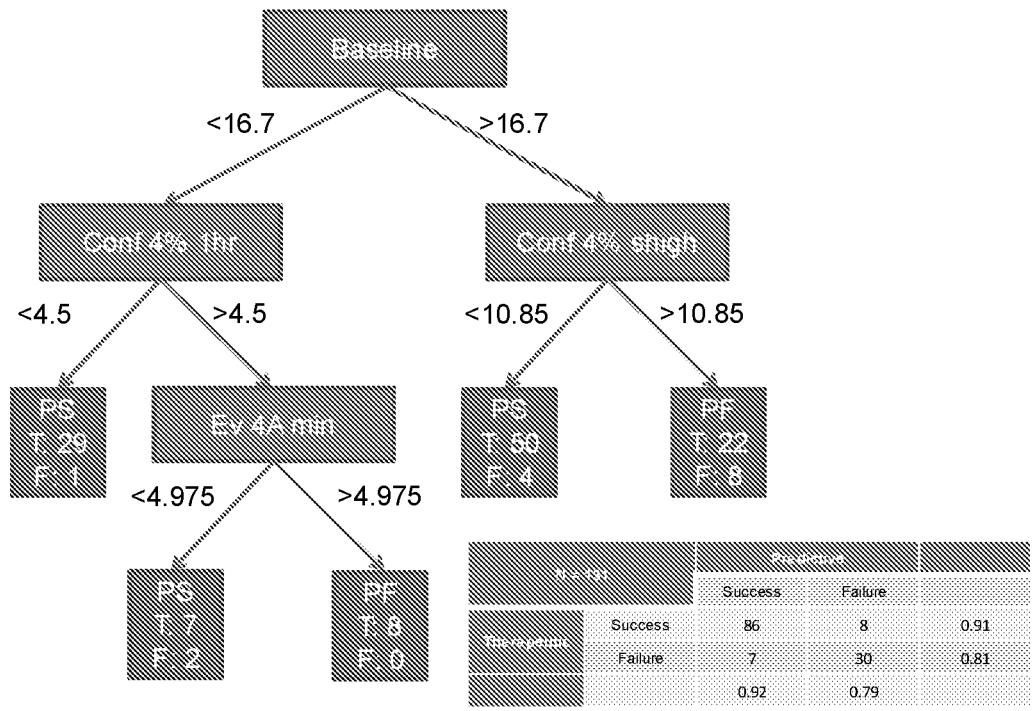
FIG. 17A is an example decision tree structure with the baseline AHI as the main trunk variable.

In an iterative approach, different setting, e.g., purity function, split criterion, etc., were tested to improve the accuracy of model's prediction. A sample DT structure constructed using two split criterion and limitations on population of each leaf to prevent over-fitting found the model to be able to correctly classify 116 out of 131 subjects (i.e., an overall error rate of 11.45%). FIG. 14C illustrates the case when the feature of baseline AHI (e.g., diagnostic information from the subject) was used as the main trunk of the tree. This was analogous to the prospective rule for success: (i) residual AHI below 10 or (ii) 50% reduction from the baseline AHI, whichever is smaller. This success rule dictates a split at baseline AHI of approximately 20: for baseline AHI above 20, success means final AHI below 10; and for below 20 success means final AHI less than 50% of the baseline AHI. A decision tree with a main trunk split at approximately 20 events per hour is shown in FIG. 17A.

Figure 17C:
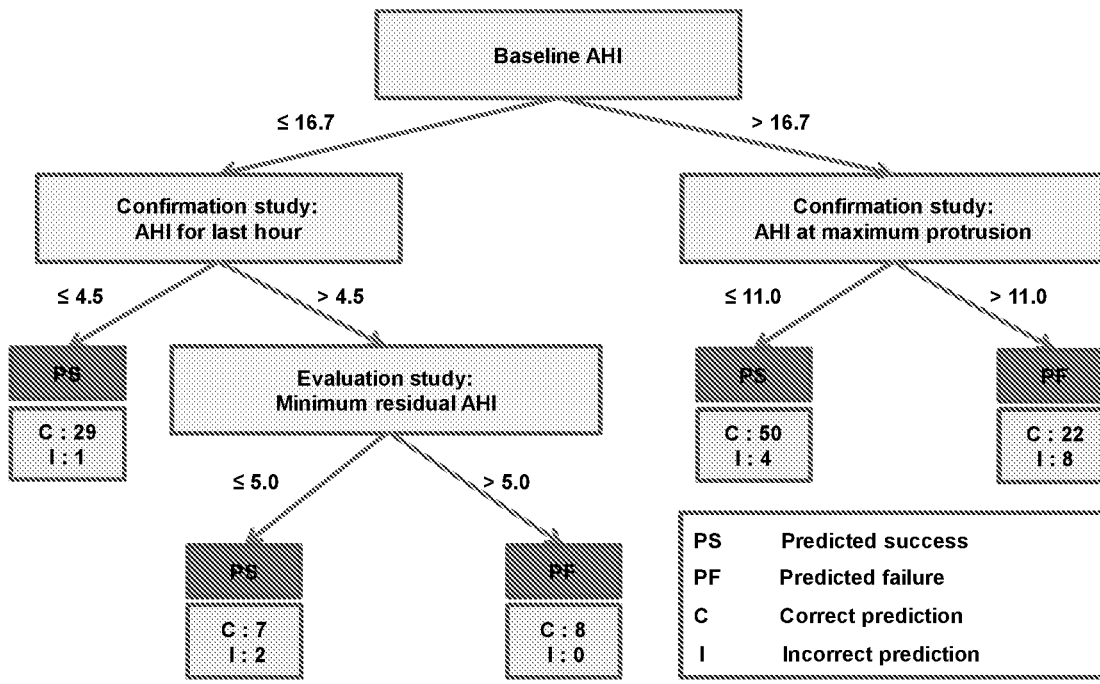
FIG. 17C is an example decision tree structure with the baseline AHI of 16.7 as the main trunk variable.
Figure 17B:
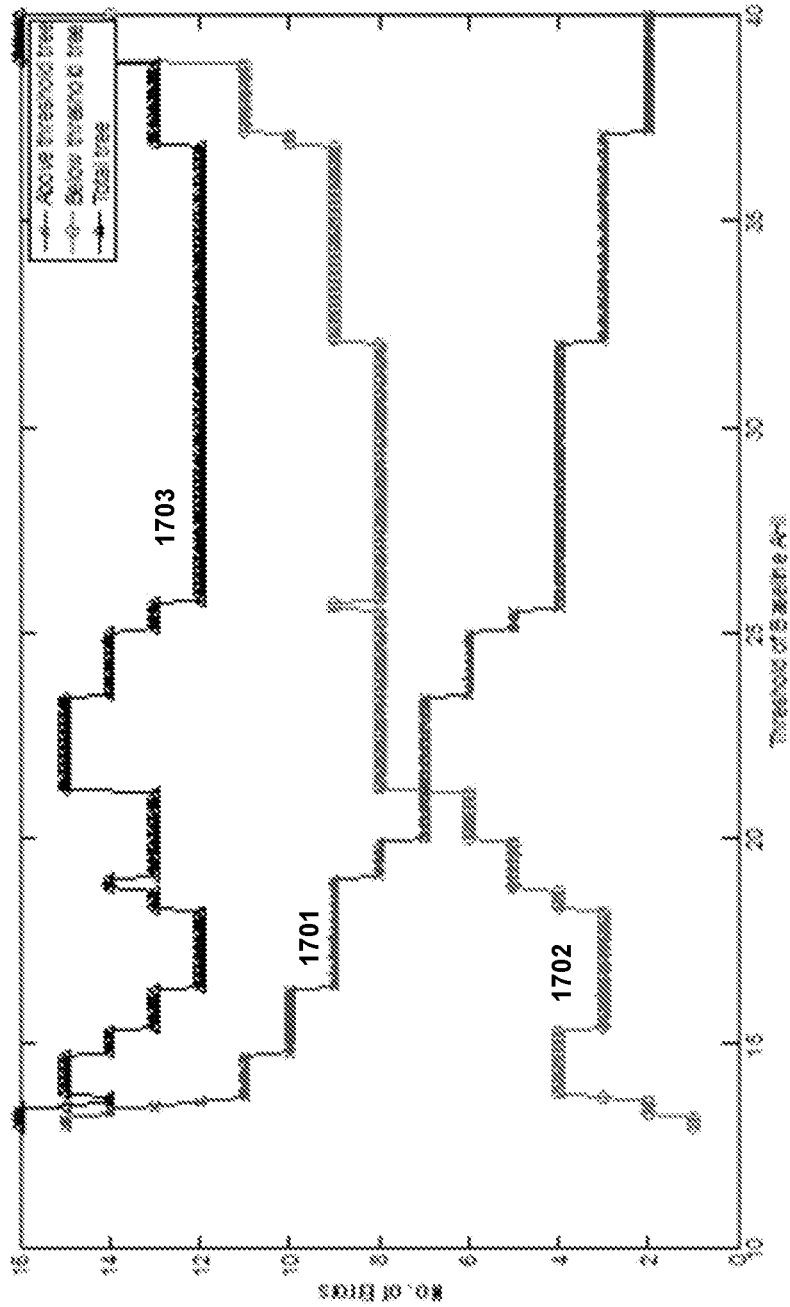
FIG. 17B is a graph illustrating predicted error vs. baseline AHI split condition (with line 1701 showing above threshold tree, line 1702 showing below threshold tree, and line 1703 showing total tree)

To improve the accuracy of this split threshold approach a sensitivity analysis was done. FIG. 17B illustrates the number of predicted errors for different split threshold of baseline AHI variable, ranging from 13 to 40. According to FIG. 17C, 16.7 is the optimum threshold value. FIG. 17C shows the DT structure based on this threshold value along with the binary classification results.

Presented above DT model with imposed trunk branch criterion of 16.7 hr$^{-1}$ for baseline AHI and additional two branching points involving three additional variables—e.g., minimum value of residual AHI from the evaluation night (e.g., the first test period in FIG. 17C), AHI for the last hour of the confirmation night (e.g., the second test period in FIG. 17C), and AHI at maximum protrusion from the confirmation night (e.g., the second test period in FIG. 17C)—reduced the overall error rate to 11% and provided values for sensitivity/specificity and P/NPV of 0.91/0.81 and 0.92/0.79. This represents an improvement over the previous results from the prospective data analysis (Example 2).

A prospective study to test the efficacy of the DT approach using an automated titration study was performed unattended, in the home environment.

Twelve subjects were recruited and subjected to a multi-night, in home titration test with the automated RCMP device. The study design was similar to the one in Example 2. In brief, each subject had previously received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays.

Once the patient was asleep, the RCMP device was controlled with a decision making algorithm (e.g., in accordance with the techniques for conducting a titration for oral appliance therapy discussed above) over a 2 to 3 night period, consisting of at least two different types of sessions. The algorithm continuously received feedback information (e.g., SaO2—oxygen saturation and naris specific air flow), automatically detected and classified apneas and hypopneas, and made moment-to-moment decisions regarding mandibular positioning. The device calculated the data set from each night to set the parameters for the following night's session. If the data was insufficient, the device repeated the same session. When the study was concluded, the data from the multiple nights was analysed to predict whether the patient was deemed to be either a successful or unsuccessful candidate for oral appliance therapy, and a target protrusive position was determined.

The subject returned to the dentist to be fitted with a permanent mandibular repositioning appliance (MRA) and tested in a post-treatment, respiratory evaluation during sleep using the same portable monitor used for baseline studies for two nights in the home with the mandibular repositioning appliance (MRA).

Of the 7 subjects that were predicted to be a success with oral appliance therapy, 7 achieved a therapeutic AHI of less than 10 per hour and a greater than 50% reduction from baseline. Of the 5 subjects that were predicted to be a failure with oral appliance therapy, 4 were correctly predicted (i.e., they did not achieve a therapeutic outcome with the permanent MRA) while 1 subjects that had been predicted to be a failure were incorrectly predicted (i.e., they did achieve a therapeutic outcome with the permanent MRA). Sensitivity was calculated as 88% and specificity was calculated as 100%. This study prospectively confirmed the improvement of the DT approach over the one detailed in Example 2.

Example 6

The same data set from (Example 2) that was retrospectively analyzed in Example 5 was analyzed using a random forest (RF) technique. The retrospective analysis was performed on 131 patients for whom the full data set was available (mean AHI=25.3±13.3 hr5 hr$^{-1}$; mean BMI=30.1±5.0 kg/m$^2$).

The analysis started with the extraction of 266 variables containing all critical information gathered during 2-3 nights of the titration process. The variables were many of the same variables that were used in Example 5 and shown in FIG. 12. The features include different measures of respiratory disturbance events at various protrusion levels and times. Another set of variables are extracted from baseline studies, demographics, questioners, and dental measurements. An ensemble machine learning technique was employed in order to find an optimal predictive model that is known to be robust against overfitting to the training set, on the contrary to a single decision tree. A random forest method where successive trees do not depend on earlier trees—each is independently constructed using a bootstrap sample of the data set and a simple majority vote is taken for prediction, was employed. The model was trained using the full data set, using class names of +1 and −1, and equal weighting for both classes. The number of decision trees was identified using the prediction error versus the number of trees, where a sufficient number is where the error rate does not substantially change. The data set was trained from varying types of success criteria (RDI<10 events per hour; RDI<10 events per hour and a 50% reduction from baseline) and different types of RDI (e.g. AHI 4%, AHI 3%, ODI 4%). To find an optimum set of randomly selected variables (NVar) and fraction of in bag observations (FBoot), different values of each were set using a random forest of 500 trees for both success criteria. Based on the output error rates in a 10-fold cross validation (CV), values of Nvar and Fboot were selected for each of the criteria. Using these inputs, the number of trees for each criterion were individually set based on a convergence of the error rate. For example, setting Nvar=10 and FBoot=0.3, in the case of an ODI 4% with a success criteria of less than 10 events per hour and a 50% reduction from baseline, the error rate converged at 150 trees. With a success criterion of only less than 10 events per hour, the error rate converged at 100 trees. After setting the number of trees, 10-fold CV was used to estimate the rate of prediction accuracy in the population. The results of 3 attempts of CV found the predictive accuracy to be consistent at 82% and 85% for the first and second measures, respectively, on the trained data set.

The objective of this retrospective analysis is to create a universal predictive model capable of binary classification of each individual OSA patient as potential responder (success) or non-responder (failure) to oral appliance therapy according to a user selected criteria of respiratory event type and success criteria with high precision and accuracy.

A prospective study to test the efficacy of the RF approach using an automated titration study was performed unattended, in the home environment.

A total of 50 subjects were recruited and subjected to a multi-night, in home titration test with the automated RCMP device. The study design was similar to the one in Example 2. In brief, each subject had previously received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays.

Once the patient was asleep, the RCMP device was controlled with a decision making algorithm (e.g., in accordance with the techniques for conducting a titration for oral appliance therapy discussed above) over a 2 to 3 night period, consisting of at least two different types of sessions. The algorithm continuously received feedback information (e.g., SaO2—oxygen saturation and naris specific air flow), automatically detected and classified apneas and hypopneas, and made moment-to-moment decisions regarding mandibular positioning. The device calculated the data set from each night to set the parameters for the following night's session. If the data was insufficient, the device repeated the same session. When the study was concluded, the data from the multiple nights was analysed to predict whether the patient was deemed to be either a successful or unsuccessful candidate for oral appliance therapy, and a target protrusive position was determined.

The subject returned to the dentist to be fitted with a permanent mandibular repositioning appliance (MRA) and tested in a post-treatment, respiratory evaluation during sleep using the same portable monitor used for baseline studies for two nights in the home with the mandibular repositioning appliance (MRA).

Of the 27 subjects that were predicted to be a success with oral appliance therapy by random forest method, 26 achieved a therapeutic AHI of less than 10 per hour and a greater than 50% reduction from baseline. Of the 21 subjects that were predicted to be a failure with oral appliance therapy, 15 were correctly predicted (i.e., they did not achieve a therapeutic outcome with the permanent MRA) while 6 subjects that had been predicted to be a failure were incorrectly predicted (i.e., they did achieve a therapeutic outcome with the permanent MRA). Sensitivity was calculated as 81% and specificity was calculated as 94%. Using a different random forest method tuned for a prediction of outcome of only less than 10 (without the reduction of 50% from baseline) sensitivity and specificity were 85% and 93% respectively. This prospective study confirmed the implementation of a random forest method for a binary classification of each individual OSA patient as potential responder (success) or non-responder (failure) to oral appliance therapy according to a user selected criteria of respiratory event type and success criteria with high precision and accuracy.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system for setting one or more parameters for a multi-test-period titration for oral appliance therapy, comprising:
   a mandibular displacement device configured to be positioned in an oral cavity of a subject;
   a monitoring unit configured to sense one or more physiological inputs from the subject; and
   a control unit comprising a processing unit and a memory operatively coupled to the processing unit, the memory having computer-executable instructions stored thereon that, when executed by the processing unit, cause the system to:
      perform a titration for oral appliance therapy during a first test period;
      identify a variable associated with the titration performed during the first test period;
      set a parameter for a titration for oral appliance therapy to be performed during a second test period, wherein the parameter is dependent on the variable associated with the titration performed during the first test period;
      perform the titration for oral appliance therapy during the second test period; and
      establish an outcome of oral appliance therapy based on the titrations performed during the first and second test periods.

2. The system of claim 1, wherein the memory has further computer-executable instructions stored thereon that, when executed by the processing unit, cause the system to:
   receive a desired outcome criteria of oral appliance therapy; and
   select a prediction protocol for establishing the outcome of oral appliance therapy based on the desired outcome criteria.

3. The system of claim 1, wherein the memory has further computer-executable instructions stored thereon that, when executed by the processing unit, cause the system to receive diagnostic information concerning the subject, wherein the diagnostic information is used to establish the outcome of oral appliance therapy or to set the parameter for a titration.

4. The system of claim 3, wherein the diagnostic information comprises at least one of a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms.

5. The system of claim 1, wherein the variable is at least one of a predicted outcome of oral appliance therapy, a predicted effective protrusion level for oral appliance therapy, a predicted optimal protrusion level for oral appliance therapy, a measure of respiratory events, a measure of respiratory events at or above a specific protrusion level, a percentage of time spent at or above a specific protrusion level, a sleep stage, or an occurrence of arousal.

6. The system of claim 1, wherein the parameter is at least one of a beginning protrusion level, a protrusion level adjustment rate, a protrusion level range, a criterion for adjusting protrusion level, a width and position of a correlation window, a type of protocol, criteria defining a respiratory event, a sleep study qualifying condition, or a length of time before adjusting protrusion level.

7. The system of claim 1, wherein the outcome of oral appliance therapy comprises at least one of a prediction of success or failure of oral appliance therapy, a predicted effective protrusion level for oral appliance therapy, or a predicted optimal protrusion level for oral appliance therapy.

8. The system of claim 1, wherein the memory has further computer-executable instructions stored thereon that, when executed by the processing unit, cause the system to determine whether to perform a titration for oral appliance therapy during one or more additional test periods based on at least one of diagnostic information concerning the subject, a desired outcome of oral appliance therapy, a desired level of accuracy for the outcome of oral appliance therapy, a desired total number of test periods, a sensitivity or tolerance of the subject, or a constraint of an adjustable mandibular displacement device.

9. The system of claim 1, wherein each respective test period comprises sleep during a different sleep session.

10. The system of claim 9, wherein the different sleep sessions are on the same night.

11. The system of claim 9, wherein the different sleep sessions are on different nights.

12. The system of claim 1, wherein the outcome of oral appliance therapy is established using a machine learning module.

13. The system of claim 1, wherein the titrations during the first and second test periods are performed in accordance with a test plan for the multi-test-period titration.

14. The system of claim 13, wherein the memory has further computer-executable instructions stored thereon that, when executed by the processing unit, cause the system to receive the test plan before performing the titrations during the first and second test periods.

15. A system for evaluating an outcome of oral appliance therapy in a subject using a multi-test-period titration, comprising:
   a mandibular displacement device configured to be positioned in an oral cavity of the subject;
   a monitoring unit configured to sense one or more physiological inputs from the subject; and
   a control unit comprising a processing unit and a memory operatively coupled to the processing unit, the memory having computer-executable instructions stored thereon that, when executed by the processing unit, cause the system to:

receive diagnostic information concerning the subject;

perform a titration for oral appliance therapy during each of first and second test periods, respectively;

select at least one variable, wherein the diagnostic information influences selection of the at least one variable;

analyze the at least one variable associated with the titrations performed during the first and second test periods; and establish the outcome of oral appliance therapy based on the at least one variable.

16. The system of claim 15, wherein the diagnostic information comprises at least one of a baseline measure of respiratory events experienced by the subject, a distribution of respiratory events, a level of desaturation, the subject's body position during a diagnostic sleep study, a sleep stage during a diagnostic sleep study, the subject's physical characteristics, the subject's medical history, or the subject's symptoms.

17. The system of claim 16, wherein the baseline measure of respiratory events comprises a frequency of respiratory events.

18. The system of claim 17, wherein the baseline measure of respiratory events is a frequency of respiratory events experienced by the subject in the absence of oral appliance therapy.

19. The system of claim 15, wherein the at least one variable is a measure of respiratory events.

20. The system of claim 19, wherein the at least one variable is a frequency of respiratory events occurring during the titration performed during the first or second test period.

21. The system of claim 19, wherein the outcome of oral appliance therapy is established based on a value of the at least one variable.

22. The system of claim 15, wherein the outcome of oral appliance therapy comprises at least one of a prediction of success or failure of oral appliance therapy, a predicted effective protrusion level for oral appliance therapy, or a predicted optimal protrusion level for oral appliance therapy.

23. The system of claim 15, wherein each respective test period comprises sleep during a different sleep session.

24. The system of claim 23, wherein the different sleep sessions are on the same night.

25. The system of claim 23, wherein the different sleep sessions are on different nights.

26. The system of claim 15, wherein the memory has further computer-executable instructions stored thereon that, when executed by the processing unit, cause the system to:

analyze one or more additional variables, wherein each of the one or more additional variables is associated with the titration performed during the first test period or the titration performed during the second test period; and establish the outcome of oral appliance therapy based on the at least one variable and the one or more additional variables.

* * * * *